(12) United States Patent
Landry et al.

(10) Patent No.: US 7,959,677 B2
(45) Date of Patent: Jun. 14, 2011

(54) ARTIFICIAL FUNCTIONAL SPINAL UNIT SYSTEM AND METHOD FOR USE

(75) Inventors: Michael E. Landry, Austin, TX (US); Erik J. Wagner, Austin, TX (US); Michael S. Schular, Pittsburgh, PA (US); Jeffrey C. Wang, Sherman Oaks, CA (US)

(73) Assignee: Flexuspine, Inc., Pittsburg, PA (US)

( * ) Notice: Subject to any disclaimer, the term of this patent is extended or adjusted under 35 U.S.C. 154(b) by 472 days.

(21) Appl. No.: 11/655,790

(22) Filed: Jan. 19, 2007

(65) Prior Publication Data
US 2008/0234764 A1    Sep. 25, 2008

(51) Int. Cl.
*A61F 2/44*    (2006.01)
(52) U.S. Cl. ..................................... 623/17.11
(58) Field of Classification Search .......... 606/247–249; 623/17.11–17.16
See application file for complete search history.

(56) References Cited

U.S. PATENT DOCUMENTS

| | | | |
|---|---|---|---|
| 3,848,601 A * | 11/1974 | Ma et al. ............... | 606/86 A |
| 3,867,728 A | 2/1975 | Substad et al. | |
| 4,309,777 A | 1/1982 | Patil | |
| 4,349,921 A | 9/1982 | Kuntz | |
| 4,611,581 A | 9/1986 | Steffee | |
| 4,657,550 A | 4/1987 | Daher | |
| 4,696,290 A | 9/1987 | Steffee | |
| 4,743,260 A | 5/1988 | Burton | |
| 4,759,766 A | 7/1988 | Buettner-Janz et al. | |
| 4,759,769 A | 7/1988 | Hedman et al. | |
| 4,772,287 A | 9/1988 | Ray et al. | |
| 4,854,311 A | 8/1989 | Steffee | |
| 4,863,476 A | 9/1989 | Shepperd | |
| 4,863,477 A | 9/1989 | Monson | |
| 4,907,577 A * | 3/1990 | Wu ............................ | 606/87 |
| 4,911,718 A | 3/1990 | Lee et al. | |

(Continued)

FOREIGN PATENT DOCUMENTS

FR    2716616    9/1995

(Continued)

OTHER PUBLICATIONS

U. S. Patent and Trademark Office "Communication" for U.S. Appl. No. 11/371,181, mailed Jun. 9, 2008; available in PAIR.

(Continued)

*Primary Examiner* — Eduardo C Robert
*Assistant Examiner* — Jerry Cumberledge
(74) *Attorney, Agent, or Firm* — Meyertons, Hood, Kivlin, Kowert & Goetzel, P.C.; Eric B. Meyertons

(57) ABSTRACT

Insertion methods for placing dynamic interbody devices between a first vertebra and a second vertebra using a posterior approach are provided. In an embodiment, the insertion method may be based on the first vertebra. A bridge assembly may be attached to tap shafts positioned in the first vertebra. The bridge assembly may establish an insertion angle of implants into a disc space between the vertebrae. In an embodiment, the insertion method may be based on the position of expandable trials positioned between the vertebrae. The trials may be positioned and a bridge assembly may be coupled to the expandable trials and taps positioned in the first vertebra. One or more posterior stabilization systems may be coupled to the vertebrae after insertion of the dynamic interbody devices between the vertebrae.

21 Claims, 22 Drawing Sheets

U.S. PATENT DOCUMENTS

| | | | |
|---|---|---|---|
| 4,932,975 A | 6/1990 | Main et al. | |
| 4,946,378 A | 8/1990 | Hirayama et al. | |
| 4,946,458 A | 8/1990 | Harms et al. | |
| 5,042,982 A | 8/1991 | Harms et al. | |
| 5,047,055 A | 9/1991 | Bao et al. | |
| 5,059,194 A * | 10/1991 | Michelson | 606/90 |
| 5,071,437 A | 12/1991 | Steffee | |
| 5,092,867 A | 3/1992 | Harms et al. | |
| 5,108,438 A | 4/1992 | Stone | |
| 5,123,926 A | 6/1992 | Pisharodi | |
| 5,171,278 A | 12/1992 | Pisharodi | |
| 5,171,281 A | 12/1992 | Parsons et al. | |
| 5,180,393 A | 1/1993 | Commarmond | |
| 5,192,326 A | 3/1993 | Bao et al. | |
| 5,196,013 A | 3/1993 | Harms et al. | |
| 5,207,678 A | 5/1993 | Harms et al. | |
| 5,246,458 A | 9/1993 | Graham | |
| 5,258,031 A | 11/1993 | Salib et al. | |
| 5,261,909 A | 11/1993 | Sutterlin et al. | |
| 5,306,307 A | 4/1994 | Senter et al. | |
| 5,306,309 A | 4/1994 | Wagner et al. | |
| 5,314,477 A | 5/1994 | Marnay | |
| 5,320,644 A | 6/1994 | Baumgartner | |
| 5,336,223 A | 8/1994 | Rogers | |
| 5,370,697 A | 12/1994 | Baumgartner | |
| 5,375,823 A | 12/1994 | Navas | |
| 5,397,364 A | 3/1995 | Kozak et al. | |
| 5,401,269 A | 3/1995 | Buettner-Janz et al. | |
| 5,403,315 A | 4/1995 | Ashman | |
| 5,415,661 A | 5/1995 | Holmes | |
| 5,423,816 A | 6/1995 | Lin | |
| 5,425,773 A | 6/1995 | Boyd et al. | |
| 5,443,467 A | 8/1995 | Biedermann et al. | |
| 5,458,642 A | 10/1995 | Beer et al. | |
| 5,458,643 A | 10/1995 | Oka et al. | |
| 5,496,321 A | 3/1996 | Puno et al. | |
| 5,498,263 A | 3/1996 | DiNello et al. | |
| 5,514,132 A | 5/1996 | Csernatony et al. | |
| 5,514,180 A | 5/1996 | Heggeness et al. | |
| 5,522,899 A | 6/1996 | Michelson | |
| 5,534,028 A | 7/1996 | Bao et al. | |
| 5,534,029 A | 7/1996 | Shima | |
| 5,534,030 A | 7/1996 | Navarro et al. | |
| 5,545,165 A | 8/1996 | Biedermann et al. | |
| 5,556,431 A | 9/1996 | Buettner-Janz | |
| 5,562,663 A | 10/1996 | Wisnewski et al. | |
| 5,562,737 A | 10/1996 | Graf | |
| 5,562,738 A | 10/1996 | Boyd et al. | |
| 5,571,109 A | 11/1996 | Bertagnoli | |
| 5,645,599 A | 7/1997 | Samani | |
| 5,653,763 A | 8/1997 | Errico et al. | |
| 5,665,122 A | 9/1997 | Kambin | |
| 5,672,176 A | 9/1997 | Biedermann et al. | |
| 5,674,294 A | 10/1997 | Bainville et al. | |
| 5,674,296 A | 10/1997 | Bryan et al. | |
| 5,676,701 A | 10/1997 | Yuan et al. | |
| 5,676,702 A | 10/1997 | Ratron | |
| 5,683,391 A | 11/1997 | Boyd | |
| 5,683,464 A | 11/1997 | Wagner et al. | |
| 5,683,465 A | 11/1997 | Shinn et al. | |
| 5,702,450 A | 12/1997 | Bisserie | |
| 5,725,527 A | 3/1998 | Biedermann et al. | |
| 5,733,284 A | 3/1998 | Martin | |
| 5,741,253 A * | 4/1998 | Michelson | 606/86 A |
| 5,755,797 A | 5/1998 | Baumgartner | |
| 5,776,199 A | 7/1998 | Michelson | |
| 5,782,832 A | 7/1998 | Larsen et al. | |
| 5,785,647 A | 7/1998 | Tompkins et al. | |
| 5,797,909 A | 8/1998 | Michelson | |
| 5,800,549 A | 9/1998 | Bao et al. | |
| 5,800,550 A | 9/1998 | Sertich | |
| 5,810,819 A | 9/1998 | Errico et al. | |
| 5,824,093 A | 10/1998 | Ray et al. | |
| 5,824,094 A | 10/1998 | Serhan et al. | |
| 5,827,328 A | 10/1998 | Buttermann | |
| 5,861,041 A | 1/1999 | Tienboon | |
| 5,863,293 A | 1/1999 | Richelsoph | |
| 5,865,846 A | 2/1999 | Bryan et al. | |
| 5,865,848 A | 2/1999 | Baker | |
| 5,888,220 A | 3/1999 | Felt et al. | |
| 5,888,226 A | 3/1999 | Rogozinski | |
| 5,893,889 A | 4/1999 | Harrington | |
| 5,895,427 A | 4/1999 | Kuslich et al. | |
| 5,895,428 A | 4/1999 | Berry | |
| 5,899,941 A | 5/1999 | Nishijima et al. | |
| 5,928,243 A | 7/1999 | Guyer | |
| 5,935,133 A | 8/1999 | Wagner et al. | |
| 5,938,663 A | 8/1999 | Petreto | |
| 5,951,555 A | 9/1999 | Rehak et al. | |
| 5,961,518 A | 10/1999 | Errico et al. | |
| 5,961,554 A | 10/1999 | Janson et al. | |
| 5,964,769 A | 10/1999 | Wagner et al. | |
| 5,976,186 A | 11/1999 | Bao et al. | |
| 5,984,967 A | 11/1999 | Zdeblick et al. | |
| 5,989,250 A | 11/1999 | Wagner et al. | |
| 5,989,290 A | 11/1999 | Biedermann et al. | |
| 5,997,539 A | 12/1999 | Errico et al. | |
| 6,001,130 A | 12/1999 | Bryan et al. | |
| 6,017,344 A | 1/2000 | Errico et al. | |
| 6,019,792 A | 2/2000 | Cauthen | |
| 6,022,376 A | 2/2000 | Assell et al. | |
| 6,030,389 A | 2/2000 | Wagner et al. | |
| 6,039,763 A | 3/2000 | Shelokov | |
| 6,045,579 A | 4/2000 | Hochshuler et al. | |
| 6,053,921 A | 4/2000 | Wagner et al. | |
| 6,063,089 A | 5/2000 | Errico et al. | |
| RE36,758 E | 6/2000 | Fitz | |
| 6,080,193 A | 6/2000 | Hochshuler et al. | |
| 6,093,205 A | 7/2000 | McLeod et al. | |
| 6,096,038 A | 8/2000 | Michelson | |
| 6,102,950 A | 8/2000 | Vaccaro | |
| 6,106,526 A | 8/2000 | Harms et al. | |
| 6,110,210 A | 8/2000 | Norton et al. | |
| 6,113,637 A | 9/2000 | Gill et al. | |
| 6,123,707 A | 9/2000 | Wagner et al. | |
| 6,126,689 A | 10/2000 | Brett | |
| 6,132,430 A | 10/2000 | Wagner et al. | |
| 6,132,464 A | 10/2000 | Martin | |
| 6,132,465 A | 10/2000 | Ray et al. | |
| 6,136,031 A | 10/2000 | Middleton | |
| 6,139,579 A | 10/2000 | Steffee et al. | |
| 6,146,421 A | 11/2000 | Gordon et al. | |
| 6,146,422 A | 11/2000 | Lawson | |
| 6,156,067 A | 12/2000 | Bryan et al. | |
| 6,162,252 A | 12/2000 | Kuras et al. | |
| 6,165,218 A | 12/2000 | Husson et al. | |
| 6,176,882 B1 | 1/2001 | Biedermann et al. | |
| 6,179,874 B1 | 1/2001 | Cauthen | |
| 6,187,048 B1 | 2/2001 | Milner et al. | |
| 6,200,348 B1 | 3/2001 | Biedermann et al. | |
| 6,206,924 B1 | 3/2001 | Timm | |
| 6,214,049 B1 | 4/2001 | Gayer et al. | |
| 6,214,050 B1 | 4/2001 | Huene | |
| 6,217,579 B1 | 4/2001 | Koros | |
| 6,228,118 B1 | 5/2001 | Gordon | |
| 6,231,609 B1 | 5/2001 | Mehdizadeh | |
| 6,241,730 B1 | 6/2001 | Alby | |
| 6,264,656 B1 | 7/2001 | Michelson | |
| 6,290,724 B1 | 9/2001 | Marino | |
| 6,296,664 B1 | 10/2001 | Middleton | |
| 6,315,797 B1 | 11/2001 | Middleton | |
| 6,331,179 B1 | 12/2001 | Freid et al. | |
| 6,348,071 B1 | 2/2002 | Steffee et al. | |
| RE37,665 E | 4/2002 | Ralph et al. | |
| 6,368,350 B1 | 4/2002 | Erickson et al. | |
| 6,368,351 B1 | 4/2002 | Glenn et al. | |
| 6,371,990 B1 | 4/2002 | Ferree | |
| 6,375,682 B1 | 4/2002 | Fleischmann et al. | |
| 6,375,683 B1 | 4/2002 | Crozet et al. | |
| 6,391,190 B1 | 5/2002 | Wagner et al. | |
| 6,395,032 B1 | 5/2002 | Gauchet | |
| 6,395,034 B1 | 5/2002 | Suddaby | |
| 6,402,784 B1 | 6/2002 | Wardlaw | |
| 6,402,785 B1 | 6/2002 | Zdeblick et al. | |
| 6,409,766 B1 | 6/2002 | Brett | |
| 6,413,259 B1 | 7/2002 | Lyons et al. | |
| 6,416,515 B1 | 7/2002 | Wagner et al. | |

| | | | | | | |
|---|---|---|---|---|---|---|
| 6,419,703 B1 | 7/2002 | Fallin et al. | | 6,991,632 B2 | 1/2006 | Ritland |
| 6,419,704 B1 | 7/2002 | Ferree | | 6,994,727 B2 | 2/2006 | Khandkar et al. |
| 6,436,140 B1 | 8/2002 | Liu et al. | | 6,997,929 B2 | 2/2006 | Manzi et al. |
| 6,440,168 B1 | 8/2002 | Cauthen | | 7,011,685 B2 | 3/2006 | Arnin et al. |
| 6,442,814 B1 | 9/2002 | Landry et al. | | 7,018,415 B1 | 3/2006 | McKay |
| 6,443,990 B1 | 9/2002 | Aebi et al. | | 7,029,475 B2 | 4/2006 | Panjabi |
| 6,447,512 B1 | 9/2002 | Landry et al. | | 7,083,622 B2 | 8/2006 | Simonson |
| 6,447,544 B1 | 9/2002 | Michelson | | 7,083,649 B2 | 8/2006 | Zucherman et al. |
| 6,451,021 B1 | 9/2002 | Ralph et al. | | 7,090,698 B2 | 8/2006 | Goble et al. |
| 6,454,769 B2 | 9/2002 | Wagner et al. | | 7,101,398 B2 | 9/2006 | Dooris et al. |
| 6,454,806 B1 | 9/2002 | Cohen et al. | | 7,118,579 B2 | 10/2006 | Michelson |
| 6,454,807 B1 | 9/2002 | Jackson | | 7,118,580 B1 | 10/2006 | Beyersdorff et al. |
| 6,478,822 B1 | 11/2002 | Leroux et al. | | 7,128,760 B2 | 10/2006 | Michelson |
| 6,478,823 B1 | 11/2002 | Michelson | | 7,147,664 B2 | 12/2006 | Louis et al. |
| 6,482,207 B1 | 11/2002 | Errico | | 7,153,310 B2 | 12/2006 | Ralph et al. |
| 6,482,234 B1 | 11/2002 | Weber et al. | | 7,204,853 B2 | 4/2007 | Gordon et al. |
| 6,488,710 B2 | 12/2002 | Besselink | | 7,273,496 B2 | 9/2007 | Mitchell |
| 6,500,205 B1 | 12/2002 | Michelson | | 7,291,150 B2 | 11/2007 | Graf |
| 6,520,996 B1 | 2/2003 | Manasas et al. | | 7,311,713 B2 | 12/2007 | Johnson et al. |
| 6,524,312 B2 | 2/2003 | Landry et al. | | 7,318,839 B2 | 12/2007 | Malberg et al. |
| 6,533,817 B1 | 3/2003 | Norton et al. | | 7,316,714 B2 | 1/2008 | Gordon et al. |
| 6,533,818 B1 | 3/2003 | Weber et al. | | 7,320,707 B2 | 1/2008 | Zucherman |
| 6,540,748 B2 | 4/2003 | Lombardo | | 7,326,250 B2 | 2/2008 | Beaurain et al. |
| 6,558,423 B1 | 5/2003 | Michelson | | 7,338,525 B2 | 3/2008 | Ferree |
| 6,562,040 B1 | 5/2003 | Wagner et al. | | 7,364,589 B2 | 4/2008 | Eisermann |
| 6,562,074 B2 | 5/2003 | Gerbec et al. | | 7,473,276 B2 | 1/2009 | Aebi et al. |
| 6,565,566 B1 | 5/2003 | Wagner et al. | | 7,476,238 B2 | 1/2009 | Panjabi |
| 6,565,605 B2 | 5/2003 | Goble et al. | | 7,517,359 B2 | 4/2009 | Drewry et al. |
| 6,569,442 B2 | 5/2003 | Gan et al. | | 7,547,309 B2 | 6/2009 | Bertagnoli et al. |
| 6,572,653 B1 | 6/2003 | Simonson | | 7,550,009 B2 | 6/2009 | Arnin et al. |
| 6,576,016 B1 | 6/2003 | Hochshuler et al. | | 7,615,068 B2 | 11/2009 | Timm et al. |
| 6,579,318 B2 | 6/2003 | Varga et al. | | 7,635,379 B2 | 12/2009 | Callahan et al. |
| 6,579,319 B2 | 6/2003 | Goble et al. | | 7,682,396 B2 | 3/2010 | Beaurain et al. |
| 6,582,467 B1 | 6/2003 | Teitelbaum et al. | | 7,699,875 B2 | 4/2010 | Timm et al. |
| 6,595,992 B1 | 7/2003 | Wagner et al. | | 7,708,778 B2 | 5/2010 | Gordon et al. |
| 6,595,998 B2 | 7/2003 | Johnson et al. | | 7,713,287 B2 | 5/2010 | Timm et al. |
| 6,610,091 B1 | 8/2003 | Reiley | | 7,713,288 B2 | 5/2010 | Timm et al. |
| 6,610,094 B2 | 8/2003 | Husson | | 7,753,958 B2 | 7/2010 | Gordon et al. |
| 6,613,050 B1 | 9/2003 | Wagner et al. | | 7,785,351 B2 | 8/2010 | Gordon et al. |
| 6,616,671 B2 | 9/2003 | Landry et al. | | 7,794,480 B2 | 9/2010 | Gordon et al. |
| 6,626,904 B1 | 9/2003 | Jammet et al. | | 7,799,082 B2 | 9/2010 | Gordon et al. |
| 6,626,905 B1 | 9/2003 | Schmeil et al. | | 2001/0020476 A1 | 9/2001 | Gan et al. |
| 6,635,062 B2 * | 10/2003 | Ray et al. ............... 606/96 | | 2001/0032020 A1 | 10/2001 | Besselink |
| 6,641,614 B1 | 11/2003 | Wagner et al. | | 2002/0040243 A1 | 4/2002 | Attali et al. |
| 6,648,893 B2 | 11/2003 | Dudasik | | 2002/0065557 A1 | 5/2002 | Goble et al. |
| 6,648,915 B2 | 11/2003 | Sazy | | 2002/0068977 A1 | 6/2002 | Jackson |
| 6,648,917 B2 | 11/2003 | Gerbec et al. | | 2002/0072801 A1 | 6/2002 | Michelson |
| 6,666,870 B2 | 12/2003 | Dixon | | 2002/0082701 A1 | 6/2002 | Zdeblick et al. |
| 6,666,891 B2 | 12/2003 | Boehm et al. | | 2002/0091390 A1 * | 7/2002 | Michelson ............... 606/61 |
| 6,679,915 B1 | 1/2004 | Cauthen | | 2002/0095154 A1 | 7/2002 | Atkinson et al. |
| 6,682,533 B1 | 1/2004 | Dinsdale et al. | | 2002/0123806 A1 | 9/2002 | Reiley |
| 6,685,742 B1 | 2/2004 | Jackson | | 2002/0128659 A1 | 9/2002 | Michelson |
| 6,692,495 B1 | 2/2004 | Zacouto | | 2002/0128714 A1 | 9/2002 | Manasas et al. |
| 6,706,070 B1 | 3/2004 | Wagner et al. | | 2002/0130112 A1 | 9/2002 | Manasas et al. |
| 6,712,819 B2 | 3/2004 | Zucherman et al. | | 2002/0138077 A1 | 9/2002 | Ferree |
| 6,716,247 B2 | 4/2004 | Michelson | | 2002/0143401 A1 | 10/2002 | Michelson |
| 6,719,796 B2 | 4/2004 | Cohen et al. | | 2003/0028250 A1 | 2/2003 | Reiley et al. |
| 6,733,531 B1 | 5/2004 | Trieu | | 2003/0040802 A1 | 2/2003 | Errico |
| 6,736,850 B2 | 5/2004 | Davis | | 2003/0055427 A1 | 3/2003 | Graf |
| 6,743,257 B2 | 6/2004 | Castro | | 2003/0069643 A1 | 4/2003 | Ralph et al. |
| 6,758,861 B2 | 7/2004 | Ralph et al. | | 2003/0074063 A1 | 4/2003 | Gerbec et al. |
| 6,773,460 B2 | 8/2004 | Jackson | | 2003/0074066 A1 | 4/2003 | Errico et al. |
| 6,802,844 B2 | 10/2004 | Ferree | | 2003/0074067 A1 | 4/2003 | Errico et al. |
| 6,811,567 B2 | 11/2004 | Reiley | | 2003/0074068 A1 | 4/2003 | Errico et al. |
| 6,821,298 B1 | 11/2004 | Jackson | | 2003/0074069 A1 | 4/2003 | Errico et al. |
| 6,852,129 B2 | 2/2005 | Gerbec et al. | | 2003/0074070 A1 | 4/2003 | Errico et al. |
| 6,863,673 B2 | 3/2005 | Gerbec et al. | | 2003/0074071 A1 | 4/2003 | Errico et al. |
| D505,205 S | 5/2005 | Freid | | 2003/0074072 A1 | 4/2003 | Errico et al. |
| 6,893,464 B2 | 5/2005 | Kiester | | 2003/0074073 A1 | 4/2003 | Errico et al. |
| 6,902,580 B2 | 6/2005 | Fallin et al. | | 2003/0074074 A1 | 4/2003 | Errico et al. |
| 6,928,284 B2 | 8/2005 | Palat et al. | | 2003/0135275 A1 | 7/2003 | Garcia et al. |
| 6,936,070 B2 | 8/2005 | Muhanna | | 2003/0135277 A1 * | 7/2003 | Bryan et al. ............... 623/17.12 |
| 6,953,477 B2 | 10/2005 | Berry | | 2003/0139812 A1 | 7/2003 | Garcia et al. |
| 6,962,606 B2 | 11/2005 | Michelson | | 2003/0149483 A1 | 8/2003 | Michelson |
| 6,964,664 B2 | 11/2005 | Freid et al. | | 2003/0176923 A1 | 9/2003 | Keller et al. |
| 6,966,929 B2 | 11/2005 | Mitchell | | 2003/0191470 A1 | 10/2003 | Ritland |
| 6,966,930 B2 | 11/2005 | Arnin et al. | | 2003/0204259 A1 | 10/2003 | Goble et al. |
| 6,974,478 B2 | 12/2005 | Reiley et al. | | 2003/0204260 A1 | 10/2003 | Ferree |
| 6,981,989 B1 | 1/2006 | Fleischmann et al. | | 2003/0220643 A1 | 11/2003 | Ferree |

| | | | | | | |
|---|---|---|---|---|---|---|
| 2003/0225409 A1 | 12/2003 | Freid et al. | | 2005/0228500 A1 | 10/2005 | Kim et al. |
| 2003/0233145 A1 | 12/2003 | Landry et al. | | 2005/0245930 A1 | 11/2005 | Timm et al. |
| 2004/0006391 A1 | 1/2004 | Reiley | | 2005/0256578 A1* | 11/2005 | Blatt et al. ............... 623/17.15 |
| 2004/0019353 A1 | 1/2004 | Freid et al. | | 2005/0273167 A1* | 12/2005 | Triplett et al. ............ 623/17.11 |
| 2004/0030387 A1* | 2/2004 | Landry et al. ............... 623/16.11 | | 2005/0273171 A1 | 12/2005 | Gordon et al. |
| 2004/0030389 A1 | 2/2004 | Ferree | | 2005/0273173 A1 | 12/2005 | Gordon et al. |
| 2004/0039448 A1 | 2/2004 | Pisharodi | | 2005/0273174 A1 | 12/2005 | Gordon et al. |
| 2004/0044411 A1 | 3/2004 | Suddaby | | 2005/0273175 A1 | 12/2005 | Gordon et al. |
| 2004/0049190 A1 | 3/2004 | Biedermann et al. | | 2005/0278026 A1 | 12/2005 | Gordon et al. |
| 2004/0049271 A1 | 3/2004 | Biedermann et al. | | 2005/0283244 A1 | 12/2005 | Gordon et al. |
| 2004/0049272 A1 | 3/2004 | Reiley | | 2005/0283245 A1 | 12/2005 | Gordon et al. |
| 2004/0049273 A1 | 3/2004 | Reiley | | 2005/0283247 A1 | 12/2005 | Gordon et al. |
| 2004/0049274 A1 | 3/2004 | Reiley | | 2005/0283248 A1 | 12/2005 | Gordon et al. |
| 2004/0049275 A1 | 3/2004 | Reiley | | 2005/0288670 A1 | 12/2005 | Panjabi et al. |
| 2004/0049276 A1 | 3/2004 | Reiley | | 2006/0009768 A1 | 1/2006 | Ritland |
| 2004/0049277 A1 | 3/2004 | Reiley | | 2006/0009850 A1 | 1/2006 | Frigg et al. |
| 2004/0049278 A1 | 3/2004 | Reiley | | 2006/0015100 A1 | 1/2006 | Panjabi et al. |
| 2004/0049280 A1 | 3/2004 | Cauthen | | 2006/0036240 A1 | 2/2006 | Colleran |
| 2004/0049281 A1 | 3/2004 | Reiley | | 2006/0036245 A1* | 2/2006 | Stern ............................... 606/61 |
| 2004/0087947 A1 | 5/2004 | Lim et al. | | 2006/0084986 A1* | 4/2006 | Grinberg et al. ................ 606/61 |
| 2004/0093083 A1* | 5/2004 | Branch et al. ............... 623/17.11 | | 2006/0089717 A1 | 4/2006 | Krishna et al. |
| 2004/0102774 A1 | 5/2004 | Trieu | | 2006/0095132 A1 | 5/2006 | Kirschman |
| 2004/0106997 A1* | 6/2004 | Lieberson .................. 623/17.16 | | 2006/0129244 A1 | 6/2006 | Ensign |
| 2004/0117020 A1 | 6/2004 | Frey et al. | | 2006/0142759 A1 | 6/2006 | Arnin et al. |
| 2004/0127989 A1 | 7/2004 | Dooris et al. | | 2006/0149228 A1 | 7/2006 | Schlapfer et al. |
| 2004/0133278 A1 | 7/2004 | Marino et al. | | 2006/0149229 A1 | 7/2006 | Kwak et al. |
| 2004/0133281 A1 | 7/2004 | Khandkar et al. | | 2006/0149278 A1* | 7/2006 | Abdou ............................ 606/90 |
| 2004/0138662 A1 | 7/2004 | Landry et al. | | 2006/0149383 A1 | 7/2006 | Arnin et al. |
| 2004/0138749 A1 | 7/2004 | Zucherman | | 2006/0155377 A1 | 7/2006 | Beaurain et al. |
| 2004/0143265 A1 | 7/2004 | Landry et al. | | 2006/0167547 A1 | 7/2006 | Suddaby |
| 2004/0143332 A1* | 7/2004 | Krueger et al. ............ 623/17.14 | | 2006/0189983 A1 | 8/2006 | Fallin et al. |
| 2004/0147928 A1 | 7/2004 | Landry et al. | | 2006/0195114 A1* | 8/2006 | Bertagnoli ....................... 606/90 |
| 2004/0153065 A1 | 8/2004 | Lim | | 2006/0195191 A1 | 8/2006 | Sweeney et al. |
| 2004/0167626 A1 | 8/2004 | Geremakis et al. | | 2006/0195192 A1 | 8/2006 | Gordon et al. |
| 2004/0181223 A1 | 9/2004 | Ritland | | 2006/0229729 A1 | 10/2006 | Gordon |
| 2004/0181284 A1 | 9/2004 | Simonson | | 2006/0241642 A1* | 10/2006 | Arnin et al. ..................... 606/90 |
| 2004/0220567 A1* | 11/2004 | Eisermann et al. .............. 606/61 | | 2006/0241769 A1 | 10/2006 | Gordon et al. |
| 2004/0236327 A1 | 11/2004 | Paul | | 2006/0241770 A1 | 10/2006 | Rhoda et al. |
| 2004/0236329 A1 | 11/2004 | Panjabi | | 2006/0241771 A1 | 10/2006 | Gordon et al. |
| 2004/0243240 A1 | 12/2004 | Beaurain et al. | | 2006/0247635 A1 | 11/2006 | Gordon et al. |
| 2004/0254643 A1 | 12/2004 | Jackson | | 2006/0247779 A1* | 11/2006 | Gordon et al. ............ 623/17.15 |
| 2004/0254644 A1 | 12/2004 | Taylor | | 2006/0260483 A1 | 11/2006 | Hartmann et al. |
| 2004/0267364 A1 | 12/2004 | Carli et al. | | 2006/0264937 A1 | 11/2006 | White |
| 2004/0267369 A1 | 12/2004 | Lyons et al. | | 2006/0265068 A1 | 11/2006 | Schwab |
| 2005/0010295 A1 | 1/2005 | Michelson | | 2006/0265074 A1 | 11/2006 | Krishna |
| 2005/0015146 A1 | 1/2005 | Louis et al. | | 2007/0010886 A1 | 1/2007 | Banick |
| 2005/0015149 A1 | 1/2005 | Michelson | | 2007/0073405 A1 | 3/2007 | Verhulst et al. |
| 2005/0021144 A1 | 1/2005 | Malberg et al. | | 2007/0073406 A1 | 3/2007 | Gordon et al. |
| 2005/0027361 A1 | 2/2005 | Reiley | | 2007/0093828 A1* | 4/2007 | Abdou ............................ 606/61 |
| 2005/0033431 A1 | 2/2005 | Gordon et al. | | 2007/0093846 A1* | 4/2007 | Frigg et al. ..................... 606/90 |
| 2005/0033432 A1 | 2/2005 | Gordon et al. | | 2007/0162137 A1 | 7/2007 | Kloss et al. |
| 2005/0033437 A1 | 2/2005 | Bao et al. | | 2007/0213720 A1 | 9/2007 | Gordon et al. |
| 2005/0033439 A1 | 2/2005 | Gordon et al. | | 2007/0213821 A1 | 9/2007 | Kwak et al. |
| 2005/0060034 A1 | 3/2005 | Berry | | 2007/0225814 A1 | 9/2007 | Atkinson |
| 2005/0107881 A1 | 5/2005 | Alleyne et al. | | 2007/0239279 A1 | 10/2007 | Francis |
| 2005/0113927 A1 | 5/2005 | Malek | | 2007/0270972 A1 | 11/2007 | Gordon et al. |
| 2005/0124991 A1 | 6/2005 | Jahng | | 2007/0288094 A1 | 12/2007 | Krishna et al. |
| 2005/0125061 A1 | 6/2005 | Zucherman et al. | | 2008/0015702 A1 | 1/2008 | Lakin et al. |
| 2005/0131406 A1 | 6/2005 | Reiley | | 2008/0027547 A1 | 1/2008 | Yu et al. |
| 2005/0143818 A1 | 6/2005 | Yuan et al. | | 2008/0033562 A1 | 2/2008 | Krishna |
| 2005/0149020 A1 | 7/2005 | Jahng | | 2008/0177310 A1 | 7/2008 | Reiley |
| 2005/0149023 A1 | 7/2005 | Ritland | | 2008/0234732 A1 | 9/2008 | Landry et al. |
| 2005/0154461 A1 | 7/2005 | Humphreys et al. | | 2008/0234740 A1 | 9/2008 | Landry et al. |
| 2005/0154465 A1 | 7/2005 | Hodges et al. | | 2008/0234741 A1 | 9/2008 | Landry et al. |
| 2005/0154466 A1 | 7/2005 | Humphreys et al. | | 2008/0234823 A1 | 9/2008 | Landry et al. |
| 2005/0159818 A1 | 7/2005 | Blain | | 2008/0312692 A1 | 12/2008 | Brennan et al. |
| 2005/0171543 A1 | 8/2005 | Timm et al. | | 2009/0143862 A1 | 6/2009 | Trieu |
| 2005/0171608 A1 | 8/2005 | Peterman et al. | | 2009/0177196 A1 | 7/2009 | Zlock et al. |
| 2005/0171610 A1 | 8/2005 | Humphreys et al. | | 2010/0174317 A1 | 7/2010 | Timm et al. |
| 2005/0177156 A1 | 8/2005 | Timm et al. | | 2010/0222819 A1 | 9/2010 | Timm et al. |
| 2005/0177157 A1 | 8/2005 | Jahng | | 2010/0331985 A1 | 12/2010 | Gordon et al. |
| 2005/0177164 A1 | 8/2005 | Walters et al. | | | | |
| 2005/0177166 A1 | 8/2005 | Timm et al. | | | | |
| 2005/0182401 A1 | 8/2005 | Timm et al. | | | FOREIGN PATENT DOCUMENTS | |
| 2005/0182409 A1 | 8/2005 | Callahan et al. | | FR | 2718946 | 10/1995 |
| 2005/0203517 A1 | 9/2005 | Jahng et al. | | FR | 2745706 | 9/1997 |
| 2005/0209697 A1 | 9/2005 | Paponneau et al. | | FR | 2799949 | 4/2001 |
| 2005/0209698 A1 | 9/2005 | Gordon et al. | | RU | 2085145 | 7/1997 |
| 2005/0222569 A1 | 10/2005 | Panjabi | | WO | 9641582 | 12/1996 |
| | | | | WO | 9848739 | 11/1998 |

| | | |
|---|---|---|
| WO | 0004851 | 2/2000 |
| WO | 0074606 | 12/2000 |
| WO | 0101893 | 1/2001 |
| WO | 0156513 | 8/2001 |
| WO | 0245625 | 6/2002 |
| WO | 2004019762 | 3/2004 |
| WO | 2004019828 | 3/2004 |
| WO | 2004019830 | 3/2004 |
| WO | 2004024011 | 3/2004 |
| WO | 2004026188 | 4/2004 |
| WO | 2004041129 | 5/2004 |
| WO | 2004054479 | 7/2004 |
| WO | 2006066198 | 6/2006 |
| WO | 2006116851 | 11/2006 |
| WO | 2007104024 | 9/2007 |
| WO | 2008089350 | 7/2008 |

OTHER PUBLICATIONS

U. S. Patent and Trademark Office "Communication" for U.S. Appl. No. 11/371,190, mailed Apr. 17, 2008; available in PAIR.
Co-pending U.S. Appl. No. 11/975,921 entitled "Dampener System for a Posterior Stabilization System With a Variable Length Elongated Member" to Gimbel et al available in PAIR.
Co-pending U.S. Appl. No. 11/975,918 entitled "Dampener System for a Posterior Stabilization System With a Fixed Length Elongated Member" to Gimbel et al available in PAIR.
Co-pending U.S. Appl. No. 11/975,920 entitled "Posterior Stabilization System With Isolated, Dual Dampener Systems" to Gimbel et al available in PAIR.
Co-pending U.S. Appl. No. 11/975,916 entitled "Posterior Stabilization System With Shared, Dual Dampener Systems" to Gimbel et al available in PAIR.
Co-pending U.S. Appl. No. 11/975,917 entitled "Dampener System for a Posterior Stabilization System With a Variable Length Elongated Member" to Gimbel et al available in PAIR.
Co-pending U.S. Appl. No. 11/975,919 entitled "Spinal Stabilization Systems With Dynamic Interbody Devices" to Gimbel et al available in PAIR.
U. S. Patent and Trademark Office "Communication" for U.S. Appl. No. 11/371,190, mailed Oct. 11, 2007; available in PAIR.
U. S. Patent and Trademark Office "Communication" for U.S. Appl. No. 11/371,181, mailed Oct. 11, 2007; available in PAIR.
U. S. Patent and Trademark Office "Communication" for U.S. Appl. No. 11/371,376, mailed Nov. 29, 2007; available in PAIR.
Co-pending U.S. Appl. No. 11/655,737 entitled "Dynamic Interbody Device" to Landry et al. filed Jan. 19, 2007, available in PAIR.
Co-pending U.S. Appl. No. 11/655,723 entitled "Artificial Functional Spinal Unit System and Method for Use" to Landry et al. filed Jan. 19, 2007, available in PAIR.
Co-pending U.S. Appl. No. 11/655,787 entitled "Artificial Functional Spinal Unit System and Method for Use" to Landry et al. filed Jan. 19, 2007, available in PAIR.
Co-pending U.S. Appl. No. 11/655,724 entitled "Artificial Functional Spinal Unit System and Method for Use" to Landry et al. filed Jan. 19, 2007, available in PAIR.
Co-pending U.S. Appl. No. 11/655,790 entitled "Artificial Functional Spinal Unit System and Method for Use" to Landry et al. filed Jan. 19, 2007, available in PAIR.
Co-pending U.S. Appl. No. 11/371,170 entitled ""Dynamic Interbody Device"" to Gordon et al. filed Mar. 8, 2006, available in PAIR.
Co-pending U.S. Appl. No. 11/371,376 entitled "Artificial Functional Spinal Unit System and Method for Use" to Gordon et al. filed Mar. 8, 2006, available in PAIR.
Co-pending U.S. Appl. No. 11/655,723 entitled ""Artificial Functional Spinal Unit System and Method for Use"" to Landry et al. filed Jan. 19, 2007, available in PAIR.
Co-pending U.S. Appl. No. 11/655,724 entitled ""Artificial Functional Spinal Unit System and Method for Use"" to Landry et al. filed Jan. 19, 2007, available in PAIR.
Co-pending U.S. Appl. No. 11/655,737 entitled ""Dynamic Interbody Device"" to Landry et al. filed Jan. 19, 2007, available in PAIR.

Serhan et al. "Biomechanics of the posterior lumbar articulating elements," Neurosurg Focus 2007, 22(1):E1, 6 pages.
Khoueir et al. "Classification of posterior dynamic stabilization devices," Neurosurg Focus, 2007, 22(1):E1, 8 pages.
Humphreys et al., "Biomechanics of the KENTI (TM) Total Joint Replacement", Presented at the Global Symposium on Motion Preservation Technology, May 9-13, 2006; 3 pages.
Hodges et al., "Biomechanics of the KENTI (TM) Total Joint Replacement", Presented at the Global Symposium on Motion Preservation Technology, May 9-13, 2006; 1 page.
Patel et al., "Changes in Kinematics following Single Level fusion, Single and Bi-Level Charite disc replacement in the Lumbar Spine" Presented at the Global Symposium on Motion Preservation Technology, May 9-13, 2006; 1 page.
PCT Search Report and Written Opinion for PCT/US2004/025090 mailed on Apr. 11, 2005 (23 pages).
PCT Search Report and Written Opinion for International Application No. PCT/US2007/063595 mailed Dec. 11, 2007, 15 pages.
International Preliminary Report on Patentability for International Application No. PCT/US2008/051346 mailed Mar. 27, 2009, 23 pages.
International Search Report and Written Opinion for International Application No. PCT/US2008/051346 mailed Sep. 9, 2008, 20 pages.
U. S. Patent and Trademark Office "Communication" for U.S. Appl. No. 11/526,849, mailed Dec. 6, 2010.
U. S. Patent and Trademark Office "Communication" for U.S. Appl. No. 11/371,328, mailed Jan. 6, 2011.
U. S. Patent and Trademark Office "Communication" for U.S. Appl. No. 11/371,376, mailed Jul. 29, 2010.
U. S. Patent and Trademark Office "Communication" for U.S. Appl. No. 11/371,190, mailed Aug. 11, 2010.
U. S. Patent and Trademark Office "Communication" for U.S. Appl. No. 11/134,091, mailed Aug. 4, 2010.
U. S. Patent and Trademark Office "Communication" for U.S. Appl. No. 11/975,916, mailed Aug. 4, 2010.
U. S. Patent and Trademark Office "Communication" for U.S. Appl. No. 11/975,917, mailed Aug. 17, 2010.
U. S. Patent and Trademark Office "Communication" for U.S. Appl. No. 11/975,919, mailed Aug. 19, 2010.
U. S. Patent and Trademark Office "Communication" for U.S. Appl. No. 11/371,182, mailed Aug. 25, 2010.
U. S. Patent and Trademark Office "Communication" for U.S. Appl. No. 11/371,188, mailed Sep. 1, 2010.
U. S. Patent and Trademark Office "Communication" for U.S. Appl. No. 10/777,411, mailed Oct. 15, 2010.
U. S. Patent and Trademark Office "Communication" for U.S. Appl. No. 11/371,170, mailed Jul. 12, 2010.
U. S. Patent and Trademark Office "Communication" for U.S. Appl. No. 10/777,411, mailed Mar. 5, 2010.
U. S. Patent and Trademark Office "Communication" for U.S. Appl. No. 11/050,632, mailed Mar. 2, 2010.
U. S. Patent and Trademark Office "Communication" for U.S. Appl. No. 11/371,190, mailed Feb. 26, 2010.
U. S. Patent and Trademark Office "Communication" for U.S. Appl. No. 11/134,082, mailed Mar. 12, 2010.
U. S. Patent and Trademark Office "Communication" for U.S. Appl. No. 11/134,069, mailed Apr. 19, 2010.
U. S. Patent and Trademark Office "Communication" for U.S. Appl. No. 11/371,188, mailed Apr. 28, 2010.
U. S. Patent and Trademark Office "Communication" for U.S. Appl. No. 11/371,170, mailed May 4, 2010.
U. S. Patent and Trademark Office "Communication" for U.S. Appl. No. 11/371,376, mailed May 26, 2010.
U. S. Patent and Trademark Office "Communication" for U.S. Appl. No. 11/526,849, mailed Jun. 1, 2010.
U. S. Patent and Trademark Office "Communication" for U.S. Appl. No. 11/134,082, mailed May 25, 2010.
U. S. Patent and Trademark Office "Communication" for U.S. Appl. No. 10/777,411, mailed Jun. 9, 2010.
U. S. Patent and Trademark Office "Communication" for U.S. Appl. No. 11/371,328, mailed Jun. 17, 2010.

U. S. Patent and Trademark Office "Communication" for U.S. Appl. No. 11/371,188, mailed Jun. 15, 2010.
U. S. Patent and Trademark Office "Communication" for U.S. Appl. No. 11/371,182, mailed Jun. 8, 2010.
U. S. Patent and Trademark Office "Communication" for U.S. Appl. No. 11/371,170, mailed May 4, 2010.
U. S. Patent and Trademark Office "Communication" for U.S. Appl. No. 11/371,170, mailed Jan. 28, 2011.
U. S. Patent and Trademark Office "Communication" for U.S. Appl. No. 11/975,916, mailed Feb. 9, 2011.
U. S. Patent and Trademark Office "Communication" for U.S. Appl. No. 11/975,917, mailed Feb. 4, 2011.
U. S. Patent and Trademark Office "Communication" for U.S. Appl. No. 11/975,919, mailed Feb. 4, 2011.
U. S. Patent and Trademark Office "Communication" for U.S. Appl. No. 11/526,849, mailed Feb. 23, 2011.
Co-pending U.S. Appl. No. 13/072,511 entitled "Interbody Device Insertion Systems and Methods" to Gimbel et al. filed Mar. 25, 2011.

* cited by examiner

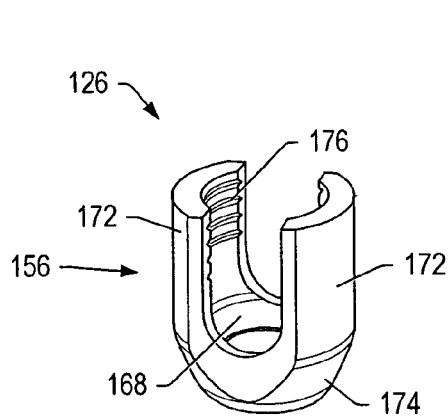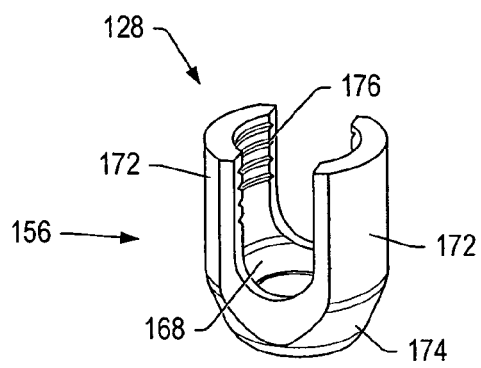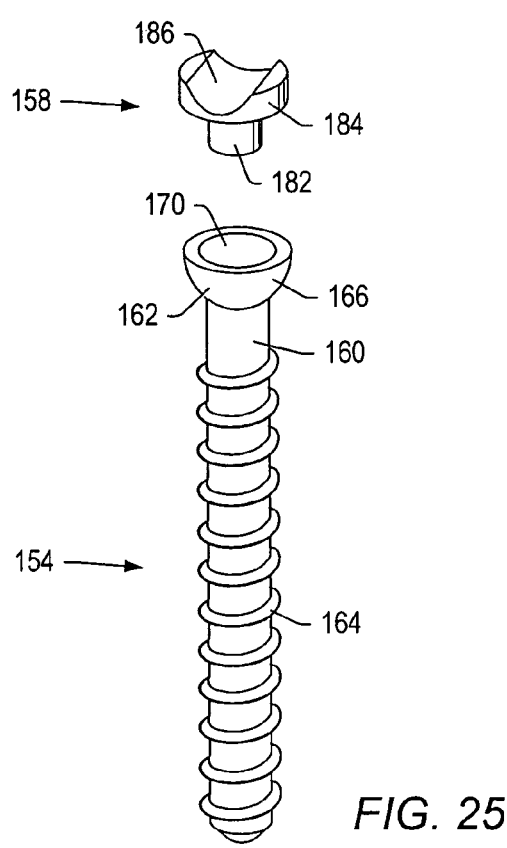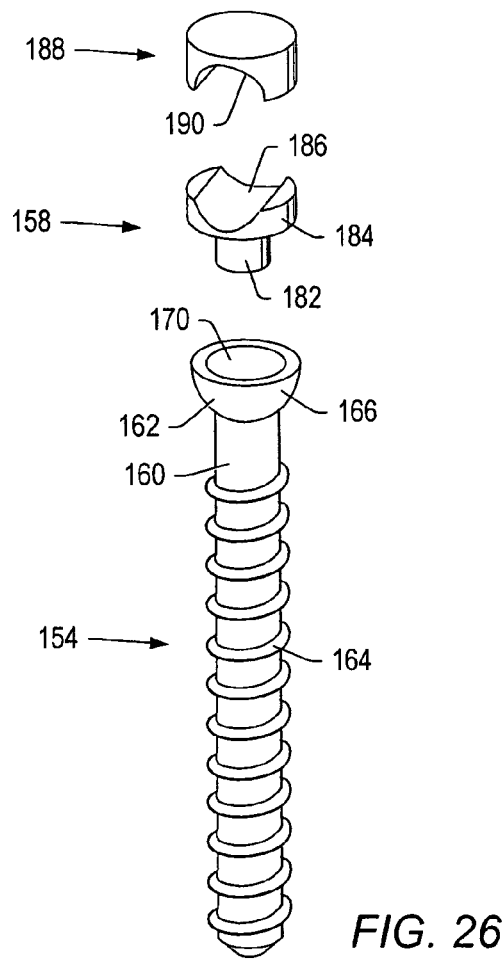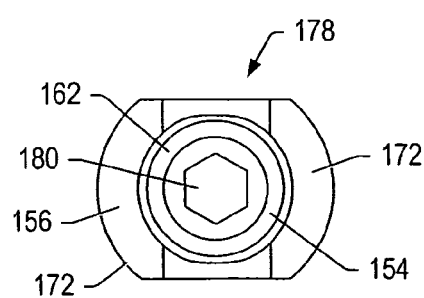
FIG. 25
FIG. 26
FIG. 27

ARTIFICIAL FUNCTIONAL SPINAL UNIT SYSTEM AND METHOD FOR USE

BACKGROUND

1. Field of the Invention

Embodiments of the invention generally relate to functional spinal implant assemblies for insertion into an intervertebral space between adjacent vertebrae of a human spine and reconstruction of the posterior elements to provide stability, flexibility, and proper biomechanical motion. More specifically, embodiments relate to dynamic intervertebral devices that allow vertebrae adjacent to the intervertebral devices to have coupled axial rotation and lateral bending. Embodiments also relate to methods of using dynamic interbody devices and dynamic stabilization systems, and to insertion methods for installing dynamic interbody devices and dynamic stabilization systems.

2. Description of Related Art

The human spine is a complex mechanical structure including alternating bony vertebrae and fibrocartilaginous discs that are connected by strong ligaments and supported by musculature that extends from the skull to the pelvis and provides axial support to the body. The intervertebral discs provide mechanical cushion between adjacent vertebral segments of the spinal column and generally include two basic components: the nucleus pulposus and the annulus fibrosis. The intervertebral discs are positioned between two vertebral end plates. The annulus fibrosis forms the perimeter of the disc and is a tough outer ring that binds adjacent vertebrae together. The end plates are made of thin cartilage overlying a thin layer of hard cortical bone that attaches to the spongy, cancellous bone of a vertebra. The vertebrae generally include a vertebral foramen bounded by the anterior vertebral body and the neural arch, which consists of two pedicles that are united posteriorly by the laminae. The spinous and transverse processes protrude from the neural arch. The superior and inferior articular facets lie at the root of the transverse process.

The human spine is a highly flexible structure capable of a high degree of curvature and twist in nearly every direction. However, genetic or developmental irregularities, trauma, chronic stress, and degenerative wear can result in spinal pathologies for which surgical intervention may be necessary. In cases of deterioration, disease, or injury, an intervertebral disc, or a portion of the intervertebral disc, may be removed from the human spine during a discectomy.

After some discectomies, one or more non-dynamic intervertebral devices may be placed in the disc space to fuse or promote fusion of the adjacent vertebrae. During some procedures, fusion may be combined with posterior fixation to address intervertebral disc and/or facet problems. The fusion procedure (e.g., posterior lumbar interbody fusion) and the posterior fixation procedure may be performed using a posterior approach. The posterior fixation and non-dynamic intervertebral devices may cooperate to inhibit motion and promote bone healing. Fusing two vertebrae together results in some loss of motion. Fusing two vertebrae together may also result in the placement of additional stress on one or more adjacent functional spinal units. The additional stress may cause deterioration of an adjacent functional spinal unit that may result in the need for an additional surgical procedure or procedures.

After some discectomies, a dynamic intervertebral device (DID) may be placed in the disc space. The DID may allow for movement of adjacent vertebrae coupled to the DID relative to each other. U.S. Pat. No. 4,863,477 to Monson, which is incorporated herein by reference, discloses a resilient dynamic device intended to replace the resilience of a natural human spinal disc. U.S. Pat. No. 5,192,326 to Bao et al., which is incorporated herein by reference, describes a prosthetic nucleus for replacing just the nucleus portion of a human spinal disc. U.S. Patent Application Publication No. 2005/0021144 to Malberg et al., which is incorporated herein by reference, describes an expandable spinal implant. Allowing for movement of the vertebrae coupled to the disc prosthesis may promote the distribution of stress that reduces or eliminates the deterioration of adjacent functional spinal units.

An intervertebral device may be positioned between vertebrae using a posterior approach, an anterior approach, a lateral approach, or other type of approach. A challenge of positioning a device between adjacent vertebrae using a posterior approach is that a device large enough to contact the end plates and slightly expand the space must be inserted through a limited space. This challenge is often further heightened by the presence of posterior osteophytes, which may cause "fish mouthing" of the posterior vertebral end plates and result in very limited access to the disc. A further challenge in degenerative disc spaces is the tendency of the disc space to assume a lenticular shape, which may require a larger implant than can be easily introduced without causing trauma to adjacent nerve roots. The size of rigid devices that may safely be introduced into the disc space is thereby limited. During some spinal fusion procedures using a posterior approach, two implants are inserted between the vertebrae. During some posterior procedures, one or both facet joints between the vertebrae may be removed to provide additional room for the insertion of a fusion device. Removal of the facet may also allow for the removal of soft tissue surrounding the facet (for example, the facet capsule) that work to resist posterior distraction.

The anterior approach poses significant challenges as well. Though the surgeon may gain very wide access to the interbody space from the anterior approach, this approach has its own set of complications and limitations. The retroperitoneal approach usually requires the assistance of a surgeon skilled in dealing with the visceral contents and the great vessels. The spine surgeon has extremely limited access to the nerve roots and no ability to access or replace the facet joints. Complications of the anterior approach that are approach specific include retrograde ejaculation, ureteral injury, and great vessel injury. Injury to the great vessels may result in massive blood loss, postoperative venous stasis, limb loss, or death. The anterior approach is more difficult in patients with significant obesity and may be virtually impossible in the face of previous retroperitoneal surgery.

A facet joint or facet joints of a functional spinal unit may be subjected to deterioration, disease or trauma that requires surgical intervention. Disc degeneration is often coupled with facet degeneration, so that disc replacement only may not be sufficient treatment for a large group of patients.

Facet degeneration may be addressed using a posterior approach. Thus a second surgical approach may be required if the disc degeneration is treated using an anterior approach. The need to address facet degeneration has led to the development of facet replacement devices. Some facet replacement devices are shown in U.S. Pat. No. 6,419,703 to Fallin et al.; U.S. Pat. No. 6,902,580 to Fallin et al.; U.S. Pat. No. 6,610,091 to Reiley; U.S. Pat. No. 6,811,567 to Reiley; and U.S. Pat. No. 6,974,478 to Reiley et al, each of which is incorporated herein by reference. The facet replacement devices may be used in conjunction with anterior disc replacement devices, but the facet replacement devices are not designed to provide a common center of rotation with the anterior disc replacement devices. The use of an anterior disc replacement device that has a fixed center of rotation contrary to the fixed center of rotation of the facet replacement device may restrict or diminish motion and be counterproductive to the intent of the operation.

Despite the difficulties of the anterior approach, the anterior approach does allow for the wide exposure needed to place a large device. In accessing the spine anteriorly, one of the major structural ligaments, the anterior longitudinal ligament, must be completely divided. A large amount of anterior annulus must also be removed along with the entire nucleus. Once these structures have been resected, the vertebral bodies may need to be over distracted to place the device within the disc space and restore disc space height. Failure to adequately tension the posterior annulus and ligaments increases the risk of device failure and/or migration. Yet in the process of placing these devices, the ligaments are overstretched while the devices are forced into the disc space under tension. Over distraction can damage the ligaments and the nerve roots. The anterior disc replacement devices currently available or in clinical trials may be too large to be placed posteriorly, and may require over distraction during insertion to allow the ligaments to hold them in position.

During some spinal stabilization procedures a posterior fixation system may be coupled to the spine. During some procedures, posterior fixation systems may be coupled to each side of the spine. The posterior fixation systems may include elongated members that are coupled to vertebrae by fasteners (e.g., hooks and screws). In some embodiments, one or more transverse connectors may be connected to the posterior fixation systems to join and stabilize the posterior fixation systems.

During some spinal stabilization procedures, dynamic posterior stabilization systems may be used. U.S. Patent Application Nos. 2005/0182409 to Callahan et al.; 2005/0245930 to Timm et al.; and 2006/0009768 to Ritland, each of which is incorporated herein by reference, disclose dynamic posterior stabilization systems.

During some spinal stabilization procedures, a dynamic interbody device or devices may be used in conjunction with one or more dynamic posterior stabilization systems. U.S. patent application Ser. No. 11/371,188 to Gordon et al., which is incorporated herein by reference, discloses dynamic interbody devices and dynamic posterior stabilization systems that may be used together to stabilize a portion of a spine.

A portion of the load applied to a spine of a patient may apply shear forces to dynamic interbody devices positioned between vertebrae. In some spinal stabilization systems, shear forces applied to the dynamic interbody devices are resisted by rod and pedicle screw constructs. The shear forces may apply large moments to the pedicle screws through the rods that result in undesired loosening of the pedicle screws. In some embodiments, the pedicle screw and rod constructs are relatively massive constructs to accommodate applied shear loads without loosening.

The width of fusion devices or dynamic devices that are installed using a posterior approach may be limited by the available insertion space and/or the need to limit retraction of neural structures exiting the vertebrae being stabilized. Subsidence of the lower vertebra caused by a fusion device or dynamic device inserted using a posterior approach has been noted in some patients. Subsidence may be due to small contact area between the vertebra and the device and/or by limited or no contact of the device over cortical bone surrounding the end plate of the vertebra. The contact surfaces of many fusion devices and/or dynamic interbody devices that are inserted using posterior approaches have substantially the same contact area against the upper vertebra and the lower vertebra being stabilized.

SUMMARY

In an embodiment, one or more dynamic interbody devices for a spine may be inserted in a disc space between vertebrae to form all or part of a stabilization system. The stabilization system for a first vertebra and a second vertebra of a human spine may comprise a first member and a second member coupled to the first member. The first member moves relative to the second member to accommodate coupled lateral bending and axial rotation of the first vertebra relative to the second vertebra when the first member and second member are positioned between the first vertebra and the second vertebra. The first member and the second member comprise a dynamic interbody device.

In an embodiment, the stabilization system for a first vertebra and a second vertebra of a human spine comprises a first member having at least one guide surface and a second member having at least one guide surface configured to interact with the guide surface of the first member. Interaction of a guide surface of the first member with a guide surface of the second member allows for lateral bending of the first vertebra relative to the second vertebra when the first member and second member are positioned between the first vertebra and the second vertebra. The first member and the second member comprise a dynamic interbody device.

In an embodiment, the stabilization system for a first vertebra and a second vertebra of a human spine comprises a first member having at least one guide surface and a second member having at least one guide surface configured to interact with the guide surface of the first member. Interaction of a guide surface of the first member with a guide surface of the second member allows for axial rotation of the first vertebra relative to the second vertebra when the first member and the second member are positioned between the first vertebra and the second vertebra. The first member and the second member comprise a dynamic interbody device.

In an embodiment, the stabilization system for a first vertebra and a second vertebra of a human spine comprises a first dynamic interbody device comprising a first member and a second member, wherein the second member is configured to move relative to the first member to accommodate coupled lateral bending and axial rotation of the first vertebra relative to the second vertebra when the first member and the second member are positioned between the first vertebra and the second vertebra; and a second dynamic interbody device comprising a first member and a second member, wherein the second member is configured to move relative to the first member to accommodate axial rotation and lateral bending of the first vertebra relative to the second vertebra when the first member and the second member are positioned between the first vertebra and the second vertebra.

In an embodiment, the stabilization system for a first vertebra and a second vertebra of a human spine comprises a first dynamic interbody device comprising: a first member having at least one guide surface; a second member having at least one guide surface configured to interact with the guide surface of the first member; and wherein interaction of a guide surface of the first member with a guide surface of the second member allows the second member to move relative to the first member to accommodate lateral bending of the first vertebra relative to the second vertebra when the first member and second member are positioned between the first vertebra and the second vertebra. The stabilization system also comprises a second dynamic interbody device comprising a first member and a second member, wherein the second member is configured to move relative to the first member to accommodate lateral bending of the first vertebra relative to the second vertebra. The first dynamic interbody device includes a portion configured to mate to a portion of the second dynamic interbody device so that the second member of the first dynamic interbody device moves in tandem with the second member of the second dynamic interbody device when the portion of the first dynamic interbody device is connected to the portion of the second dynamic interbody device.

In an embodiment, the stabilization system for a first vertebra and a second vertebra of a human spine comprises a first dynamic interbody device comprising: a first member having at least one guide surface; a second member having at least one guide surface configured to interact with the guide surface of the first member; and wherein interaction of a guide surface of the first member with a guide surface of the second member allows the second member to move relative to the first member to accommodate axial rotation of the first vertebra relative to the second vertebra when the first member and second member are positioned between the first vertebra and the second vertebra. The stabilization system also comprises a second dynamic interbody device comprising a first member and a second member, wherein the second member is configured to move relative to the first member to accommodate axial rotation of the first vertebra relative to the second vertebra when the first member and second member are positioned between the first vertebra and the second vertebra. The first dynamic interbody device includes a portion configured to mate to a portion of the second dynamic interbody device so that the second member of the first dynamic interbody device moves in tandem with the second member of the second dynamic interbody device when the portion of the first dynamic interbody device is connected to the portion of the second dynamic interbody device.

In an embodiment, the stabilization system for a first vertebra and a second vertebra of a human spine comprises a first member configured to couple to the first vertebra, the first member having an inferior surface configured to contact the first vertebra and a width; and a second member configured to couple to an upper vertebra of a pair of vertebra, the second member having a superior surface configured to contact the second vertebra and a width. The first member is coupled to the second member to allow for motion of the first member relative to the second member to accommodate motion of the first vertebra relative to the second vertebra when the first member and the second member are coupled to the first vertebra and second vertebra. The width of the first member is larger than width of the second member.

In an embodiment, the stabilization system for a first vertebra and a second vertebra of a human spine comprises a first member configured to couple to the first vertebra, the first member having an inferior surface configured to contact the first vertebra; a second member coupled to the first member, wherein the second member is configured to move relative to the first member to allow for coupled axial rotation and lateral bending; and a third member coupled to the second member, the third member having a superior surface configured to contact the second vertebra, and wherein the third member is configured to move relative to the second member to accommodate flexion of the first vertebra relative to the second vertebra when the first member and the third member are coupled to the first vertebra and second vertebra. The width of the first member is larger than the width of the third member.

In an embodiment, the stabilization system for a first vertebra and a second vertebra of a human spine comprises a first member configured to couple to the first vertebra, the first member having an inferior surface configured to contact the first vertebra; a second member coupled to the first member, wherein the second member is configured to move relative to the first member to allow for coupled axial rotation and lateral bending; and a third member coupled to the second member, the third member having a superior surface configured to contact the second vertebra, and wherein the third member is configured to move relative to the second member to accommodate extension of the first vertebra relative to the second vertebra when the first member and the third member are coupled to the first vertebra and second vertebra. The surface area of the inferior surface of the first member is larger than the surface area of the superior surface of the third member.

In an embodiment, the stabilization system for a first vertebra and a second vertebra of a human spine comprises a first member having a plurality of arcuate grooves and ridges and a second member having a plurality of arcuate grooves and ridges. The grooves and ridges of the first member interact with the grooves and ridges of the second member so that axial rotation of the first vertebra relative to the second vertebra causes lateral bending of the first vertebra relative to the second vertebra when the first member and the second member are positioned between the first vertebra and the second vertebra. The first member and the second member comprise a dynamic interbody device.

In an embodiment, the stabilization system for a first vertebra and a second vertebra of a human spine comprises a first member having a plurality of arcuate grooves and ridges and a second member having a plurality of arcuate grooves and ridges. The grooves and ridges of the first member interact with the grooves and ridges of the second member so that lateral bending of the first vertebra relative to the second vertebra causes axial rotation of the first vertebra relative to the second vertebra when the first member and the second member are positioned between the first vertebra and the second vertebra. The first member and the second member comprise a dynamic interbody device.

In an embodiment, a method for stabilizing a first vertebra and a second vertebra of a human spine comprises inserting a dynamic interbody device into a disc space between the first vertebra and the second vertebra from an anterior side of the first vertebra, wherein a first member of the interbody device is configured to move relative to a second member of the dynamic interbody device to allow for coupled axial rotation and lateral bending of the first vertebra relative to the second vertebra.

In an embodiment, a method for stabilizing a first vertebra and a second vertebra of a human spine comprises inserting a first dynamic interbody device into a disc space on a first side of the first vertebra and the second vertebra from a posterior side of the first vertebra and inserting a second dynamic interbody device into the disc space on a second side of the first vertebra and the second vertebra from the posterior side of the first vertebra. A first member of the first dynamic interbody device is configured to move relative to a second member of the first dynamic interbody device to allow for coupled axial rotation and lateral bending of the first vertebra relative to the second vertebra.

In an embodiment, a method for stabilizing a first vertebra and a second vertebra of a human spine comprises inserting a first dynamic interbody device into a disc space on a first side of the first vertebra and the second vertebra from a posterior side of the first vertebra; inserting a second dynamic interbody device into the disc space on a second side of the first vertebra and the second vertebra from the posterior side of the first vertebra; and coupling the first dynamic interbody device to the second dynamic interbody device. A first member of the first dynamic interbody device is configured to move relative to a second member of the first dynamic interbody device to allow for coupled axial rotation and lateral bending of the first vertebra relative to the second vertebra.

In an embodiment, a method may be used to insert a first dynamic interbody device and a second dynamic interbody device in a disc space between a first vertebra and a second vertebra. The method may include placing taps into the first vertebra, attaching a bridge assembly to the taps and positioning a face of the bridge assembly at a desired position relative to the first vertebra, attaching a first guide and a second guide to the bridge assembly, placing an end of a first expandable trial through the first guide and in the disc space between the first vertebra and the second vertebra, placing an end of a second expandable trial through the second guide and in the disc space between the first vertebra and the second vertebra, adjusting the separation distance between a movable plate and a base plate of the first expandable trial and adjusting the separation distance between a movable plate and a base plate of the second expandable trial, attaching the first dynamic interbody device to an inserter and attaching the second dynamic interbody device to an inserter, removing the first expandable trial from the disc space and first guide, placing the first dynamic interbody device through the first guide and into the disc space, removing the second expandable trial from the disc space and second guide, placing the second dynamic interbody device through the second guide and into the disc space, and releasing the first dynamic interbody device and the second dynamic interbody device from the inserters.

In an embodiment, a method may be used to insert a first dynamic interbody device and a second dynamic interbody device in a disc space between a first vertebra and a second vertebra. The method may include inserting a first expandable trial and a second expandable trial in the disc space between the vertebra, coupling a first guide to the first expandable trial and a second guide to the second expandable trial, attaching a bridge assembly to the first guide and the second guide, adjusting the separation distance between a movable plate and a base plate of the first expandable trial and adjusting the separation distance between a movable plate and a base plate of the second expandable trial, attaching the first dynamic interbody device to an inserter and attaching the second dynamic interbody device to an inserter, removing the first expandable trial from the disc space and guide, placing the first dynamic interbody device through the first guide and into the disc space, removing the second expandable trial from the disc space and second guide, placing the second dynamic interbody device through the second guide and into the disc space, and releasing the first dynamic interbody device and the second dynamic interbody device from the inserters.

BRIEF DESCRIPTION OF THE DRAWINGS

Advantages of the present invention will become apparent to those skilled in the art with the benefit of the following detailed description and upon reference to the accompanying drawings in which:

FIG. 25 depicts the components of an embodiment of a first bone fastener of a dynamic posterior stabilization system.

FIG. 26 depicts a top view of an embodiment of a fastener and collar combination for a bone fastener.

FIG. 27 depicts the components of an embodiment of a second bone fastener of a dynamic posterior stabilization system.

Figure 1:
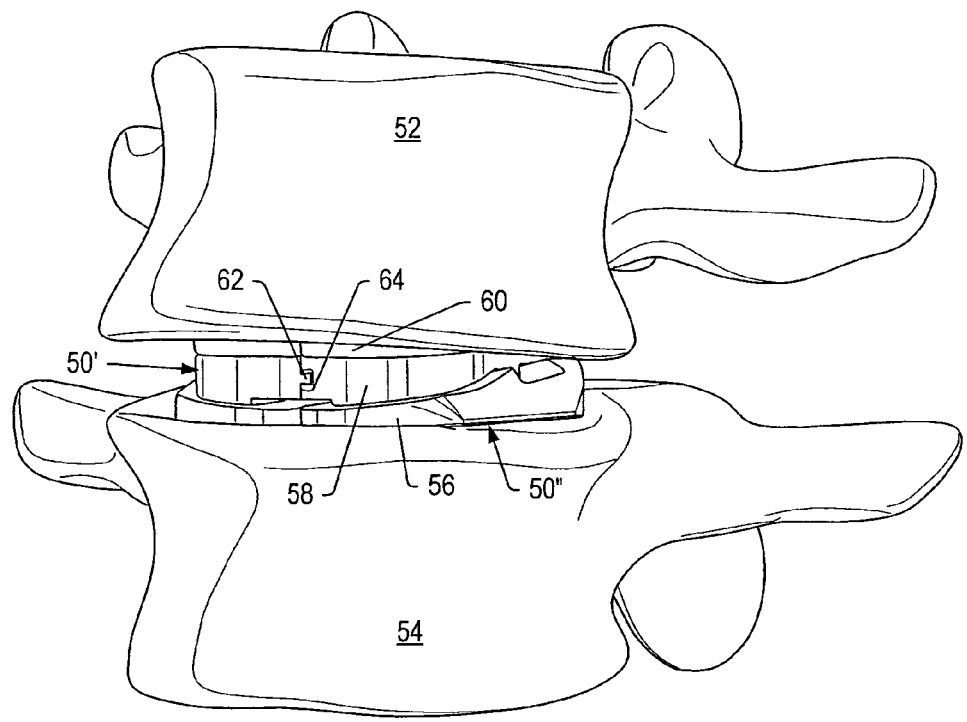
FIG. 1 depicts embodiments of dynamic interbody devices positioned between vertebrae.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

A "functional spinal unit" generally refers to a motion segment of a spine. The functional spinal unit may include two vertebrae, an intervertebral disc between the vertebrae, and the two facet joints between the vertebrae. An "artificial functional spinal unit" refers to a functional spinal unit where one or more of the components of the functional spinal unit are replaced by implants or devices that permit at least some motion of the spine. At least a portion of the intervertebral disc and/or one or both of the facet joints may be replaced by implants or devices during a spinal stabilization procedure.

As used herein, "coupled" includes a direct or indirect joining or touching unless expressly stated otherwise. For example, a first member is coupled to a second member if the first member contacts the second member, or if a third member is positioned between the first member and the second member.

A "dynamic interbody device" generally refers to an artificial intervertebral implant that allows for flexion/extension, lateral bending and/or axial rotation of vertebrae coupled to the device. The dynamic interbody device may replace a portion or all of an intervertebral disc. In some embodiments, a pair of dynamic interbody devices are installed during a spinal stabilization procedure. In some embodiments, one or more dynamic interbody devices are installed using a posterior approach. In other embodiments, a dynamic interbody device may be installed using an anterior approach or other type of approach. In some embodiments, one or more dynamic interbody devices are placed in a disc space between vertebrae, and at least one posterior stabilization system is coupled to the vertebrae. In some embodiments, one or more dynamic interbody devices are placed in the disc space without coupling a posterior stabilization system to the vertebrae.

In some embodiments, the dynamic interbody device is a bimodal device. Bimodal refers to a device that has at least two separate curved surfaces to accommodate flexion/extension with lateral bending and/or axial rotation.

Dynamic interbody devices may have surfaces that contact vertebrae. In some embodiments, a surface of the dynamic interbody device that contacts a vertebra may include one or more keels, protrusions, and/or osteoconductive/osteoinductive layers or coatings. A keel of the dynamic interbody device may be positioned in a channel formed in a vertebra. The channel may be formed in the vertebra so that the dynamic interbody device will be positioned at a desired location when inserted into the patient. Protrusions of the dynamic interbody device may penetrate an endplate of the vertebra to secure the dynamic interbody device to the vertebra. An osteoconductive/osteoinductive layer may promote bone growth that secures the dynamic interbody device to the vertebra. The osteoconductive/osteoinductive layer may include, but is not limited to a scaffold, a roughened surface, a surface treated with a titanium plasma spray, bone morphogenic proteins, and/or hydroxyapatite. A roughened surface may be formed by chemical etching, by surface abrading, by shot peening, by an electrical discharge process, and/or by embedding particles in the surface.

An anterior end of a dynamic interbody device may have a height that is greater than the height of a posterior end of the dynamic interbody device. The difference in heights between the anterior end and the posterior end of the dynamic interbody device may provide the patient with a desired amount of lordosis. Dynamic interbody devices that provide different amounts of lordosis may be provided in an instrument kit supplied for a spinal stabilization procedure. For example, the instrument kit for a posterior spinal stabilization procedure may include pairs of dynamic interbody devices that establish 0°, 3°, 6°, 9°, 12° or 15° of lordosis. Other dynamic interbody device lordosis angles or lordosis angle ranges may be provided. The amount of lordosis provided by a dynamic interbody device may be printed or etched on a visible surface of the dynamic interbody device. Other information may also be printed or etched on the visible surface of the dynamic interbody device. Such information may include dimension information (e.g., length, width, and/or height) and whether the dynamic interbody device is to be installed on the left side of the patient or the right side of the patient.

In some embodiments, one or more dynamic interbody devices are installed in a disc space formed between vertebrae during a spinal stabilization procedure. The shape and/or size of a dynamic interbody device may depend on a number of factors including surgical approach employed for insertion, intended position in the spine (e.g., cervical or lumbar), and patient anatomy. A dynamic interbody device for the lumbar spine may have a height that is less than about 22 mm. Several sizes of interbody devices may be provided in the instrument kit for the spinal stabilization procedure. In an embodiment, dynamic interbody devices having heights of 6 mm, 8 mm, 10 mm, 12, mm, 14 mm, 16 mm, 18 mm, and 20 mm are provided in the instrument kit for the spinal stabilization procedure. Other sizes and/or different height ranges of dynamic interbody devices may be provided in the instrument kit for the spinal stabilization procedure. The dynamic interbody devices may include indicia indicating the height of the spinal stabilization devices.

The dynamic interbody devices may allow for flexion/extension. The dynamic interbody device may allow for a maximum of about 20° of flexion from the neutral position. The dynamic interbody device may be designed so that the dynamic interbody device has a smaller or a larger maximum angle of flexion from the neutral position. In some embodiments, the dynamic interbody device allows for a maximum of about 7° of flexion from the neutral position. In some embodiments, the maximum amount of flexion allowed by the dynamic interbody device is substantially the same as the maximum amount of extension allowed by the dynamic interbody device. In some embodiments, the maximum amount of flexion allowed by the dynamic interbody device is different from the maximum amount of extension. For example, an embodiment of a dynamic interbody device allows for a maximum of about 15° of flexion and a maximum of about 10° of extension.

The dynamic interbody device may allow for up to about 5° of axial rotation of vertebrae coupled to the dynamic interbody device (e.g. ±2.5° of rotation from a neutral position). The dynamic interbody device may allow for more or less axial rotation. In an embodiment, the dynamic interbody device allows for about ±1.5° of axial rotation of vertebrae coupled to the dynamic interbody device from a neutral position.

The dynamic interbody device may allow for up to about 10° of lateral bending of vertebrae coupled to the dynamic interbody device (e.g. ±5° of lateral bending from a neutral position). The dynamic interbody device may allow for more or less lateral bending. In an embodiment, the dynamic interbody device allows for about ±3° of lateral bending of vertebrae coupled to the dynamic interbody device from a neutral position.

The dynamic interbody device may allow for coupled lateral bending and axial rotation so that axial rotation causes some lateral bending and lateral bending causes some axial rotation. The dynamic interbody device may be formed so that a set amount of lateral bending results in a set amount of axial rotation. For example, 1° of lateral bending results in about 0.5° of axial rotation (i.e. a 2:1 ratio of lateral bending to axial rotation). A 4:1, 3:1, 2.5:1, 2:1, 1.5:1, 1:1 or other ratio of lateral bending to axial rotation may be set for the dynamic interbody devices. In some embodiments, dynamic interbody devices may be designed to be positioned between two particular vertebrae (e.g., between L4 and L5, between L3 and L4, etc.). The ratio of lateral bending to axial rotation may be selected mimic the natural ratio of lateral bending to axial rotation for normal vertebrae of the same level.

In some embodiments, a pair of dynamic interbody devices may be installed between two vertebrae to establish all or a portion of a spinal stabilization system. Each dynamic interbody device of the pair of dynamic interbody devices may be installed using a posterior approach.

In some embodiments, a single dynamic interbody device may be positioned in a disc space between vertebrae. The use of a single dynamic interbody device may avoid the need to have left oriented and right oriented dynamic interbody devices. The single dynamic interbody device may be installed using an anterior approach, a posterior approach, or a different type of approach. Single dynamic interbody devices inserted using an anterior approach may be installed using installation procedures known in the art. The coupled axial rotation/lateral bending of the anterior dynamic interbody device includes the functionality of the facet joints. One or both of the facets may be removed using a simple minimally invasive procedure without the need to install a posterior stabilization system.

As used herein a "dynamic posterior stabilization system" generally refers to an apparatus used to replace or supplement a facet joint while allowing for both dynamic resistance and at least some motion of the first vertebra to be stabilized relative to the second vertebra to be stabilized. The first vertebra and the second vertebra may be vertebrae of a functional spinal unit. In some embodiments, bone fasteners of the dynamic posterior stabilization system are secured to the first vertebra and the second vertebra. In some embodiments, a bone fastener of the dynamic posterior stabilization system may be coupled to a vertebra adjacent to the vertebrae of the functional spinal unit being stabilized. The bone fasteners may be coupled to lamina, pedicles, and/or vertebral bodies of the vertebrae. In some embodiments, dynamic posterior stabilization systems may be positioned in three or more vertebrae to form a multi-level stabilization system.

The dynamic posterior stabilization system may replace or supplement a normal, damaged, deteriorated, defective or removed facet joint. The dynamic posterior stabilization system may include bone fasteners, an elongated member, and at least one bias member. The bias member may provide little initial resistance to movement of a first vertebra coupled to the system relative to a second vertebra coupled to the system. Resistance to additional movement of the first vertebra relative to the second vertebra may increase. The increasing resistance provided by the bias member may mimic the behavior of a normal functional spinal unit. The dynamic posterior stabilization system may stabilize the vertebrae, limit the range of motion of the first vertebra relative to the second vertebra, and/or share a portion of the load applied to the vertebrae.

The dynamic posterior stabilization systems disclosed herein may allow for rotational and/or translational motion of an elongated member (e.g., a rod or plate) relative to one or more bone fasteners. The bone fasteners may include threading, barbs, rings or other protrusions that secure the bone fasteners to vertebrae. In some embodiments, the bone fasteners may be cemented or glued to the vertebrae. Bone fasteners may include collars. In some embodiments, a collar of a bone fastener is an integral portion of the bone fastener. In some embodiments, the collar is a separate component that is coupled to at least one other component of the bone fastener. The collar of the bone fastener is the portion of the bone fastener that couples to an elongated member of the dynamic posterior stabilization system. In some embodiments, the bone fasteners are polyaxial pedicle screws and the collars are the upper portions of the polyaxial pedicle screws. In some embodiments, the bone fasteners are bone screws and the collars are plates or other structures that are coupled to the bone screws.

During installation of dynamic interbody devices of a spinal stabilization system, or during installation of a single dynamic interbody device, one or both facet joints of the vertebrae may be removed. A dynamic posterior stabilization system may be installed to replace a removed facet joint. One or both of the dynamic interbody devices of the spinal stabilization system, or the single dynamic interbody device, may be coupled to a dynamic posterior stabilization system. Coupling a dynamic interbody device to the dynamic posterior stabilization system may inhibit backout of the dynamic interbody device from the disc space.

In some embodiments, a dynamic posterior stabilization system may be installed without removal of a facet joint. The dynamic posterior stabilization system may be installed after a discectomy, laminectomy, or other procedure. The dynamic posterior stabilization system may change the dynamic resistance that is not normal due to degeneration, disease, loss of a portion of the intervertebral disc and/or tissue damage.

A dynamic interbody device and a dynamic posterior stabilization system may include one or more biocompatible metals having a non-porous quality and a smooth finish (e.g., surgical grade stainless steel, titanium and/or titanium alloys). In some embodiments, a dynamic interbody device or dynamic posterior stabilization system may include ceramic and/or one or more other suitable biocompatible materials, such as biocompatible polymers and/or biocompatible metals. Biocompatible polymers may include, but are not limited to, polyetheretherketone resins ("PEEK"), carbon reinforced PEEK, ultra high molecular weight polyethylenes, polyethylenes, polyanhydrides, and alpha polyesters. For example, a dynamic interbody device or a dynamic posterior stabilization system may be constructed of a combination of biocompatible materials including cobalt chromium alloy, ultra high molecular weight polyethylene, and polycarbonate—urethane or silicone blend.

Dynamic interbody devices may include surfaces that mate with complementary surfaces and allow for motion of vertebrae coupled to the dynamic interbody devices. Components or members of dynamic interbody devices may be formed using CNC (computer numerical control) machining or other techniques. Some surfaces of the dynamic interbody devices may be treated to promote movement of the surfaces and/or inhibit galling. For example, two surfaces that move relative to each other may have mismatched hardness and/or different surface finish orientations to promote free movement of the surfaces relative to each other.

In some embodiments, dynamic interbody devices and dynamic posterior stabilization systems may be made of non-magnetic, radiolucent materials to allow unrestricted intra-operative and post-operative imaging. Certain material may interfere with x-ray and/or magnetic imaging. Magnetic materials may interfere with magnetic imaging techniques. Most non-magnetic stainless steels and cobalt chrome contain enough iron and/or nickel so that both magnetic imaging and x-ray imaging techniques are adversely affected. Other materials, such as titanium and some titanium alloys, are substantially iron free. Such materials may be used when magnetic imaging techniques are to be used, but such materials are often radio-opaque and sub-optimal for x-ray imagining techniques. Many ceramics and polymers are radiolucent and may be used with both magnetic imaging techniques and x-ray imaging techniques. The dynamic interbody devices and/or the dynamic posterior stabilization systems may include coatings and/or markers that indicate the positions of the devices and/or systems during operative and/or post-operative imaging.

In some embodiments, two dynamic interbody devices may be positioned in a disc space between two vertebrae during a spinal stabilization procedure. The largest width of each dynamic interbody device may be less than one half the width of the vertebrae the dynamic interbody devices are to be positioned between. FIG. 1 depicts embodiments of dynamic interbody devices 50', 50" that may be implanted using a posterior approach. Anterior ends and/or posterior ends of dynamic interbody devices 50', 50" may be positioned near the edge of the endplates of vertebrae 52, 54 so that the dynamic interbody devices abut strong, supportive bone of the vertebrae to be stabilized. Dynamic interbody devices 50', 50" may be bilateral devices with coupled axial rotation and lateral bending.

Figure 2:
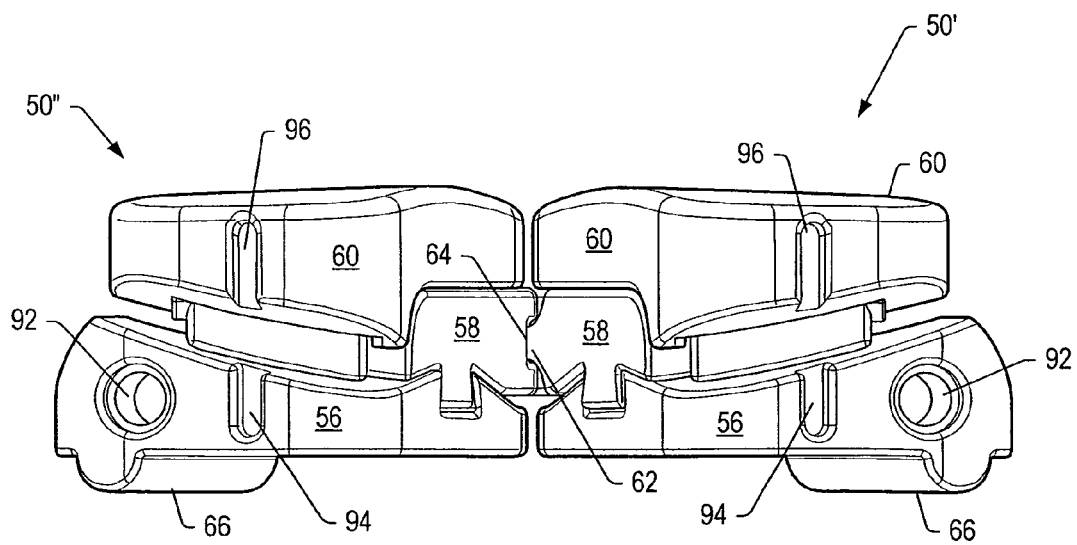
FIG. 2 depicts a rear view of dynamic interbody device embodiments.

FIG. 2 depicts a rear view of dynamic interbody devices 50', 50". Each dynamic interbody device 50' or 50" may include first member 56, second member 58 and third member 60. First members 56 may be coupled to second members 58 so that dynamic interbody devices 50', 50" accommodate lateral bending and axial rotation of vertebrae coupled to the dynamic interbody devices. In some embodiments, dynamic interbody devices 50', 50" couple lateral bending and axial motion together so that lateral bending motion causes axial rotation, and axial rotation causes lateral bending. Third members 60 may be coupled to second members 58 so that dynamic interbody device 50', 50" accommodate flexion and extension of vertebrae coupled to the dynamic interbody device. Dynamic interbody devices 50', 50" are shown in positions of neutral lateral bending, neutral axial rotation and maximum flexion in FIG. 2.

In some embodiments, the first members are coupled to the second members to allow for lateral bending without coupled axial rotation. In some embodiments, the first members are coupled to the second members to allow for axial rotation without coupled lateral bending.

In some embodiments, first member 56 of dynamic interbody device 50' may be substantially a mirror image first member 56 of dynamic interbody device 50", and third member 60 of dynamic interbody device 50' may be substantially a mirror image of third member 60 of dynamic interbody device 50". In other embodiments, the first member of dynamic interbody device 50' may have a shape that is different than the mirror image of the first member of dynamic interbody device 50" and/or the third member of dynamic interbody device 50' may have a shape that is different than the mirror image of the third member of dynamic interbody device 50".

Second member 58 of dynamic interbody device 50' may be substantially the mirror image of second member 58 of dynamic interbody device 50" with the exception of second member 58 of dynamic interbody device 50' having portion 62 that engages portion 64 of second member 58 of dynamic interbody device 50" to join dynamic interbody device 50' to dynamic interbody device 50" when the dynamic interbody devices are positioned between vertebrae. In other embodiments, first member 56 of dynamic interbody device 50' has a portion that engages a portion of first member 56 of dynamic interbody device 50" when the dynamic interbody devices are positioned between vertebrae. In other embodiments, third member 60 of dynamic interbody device 50' has a portion that engages a portion of first member 60 of dynamic interbody device 50" when the dynamic interbody devices are positioned between vertebrae.

Figure 3:
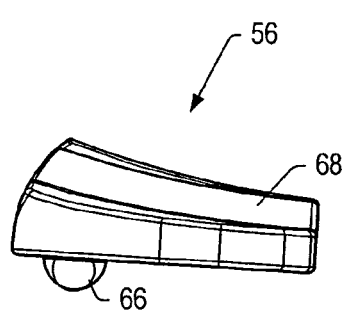
FIG. 3 depicts a front view of the first member of a dynamic interbody device embodiment.
Figure 4:
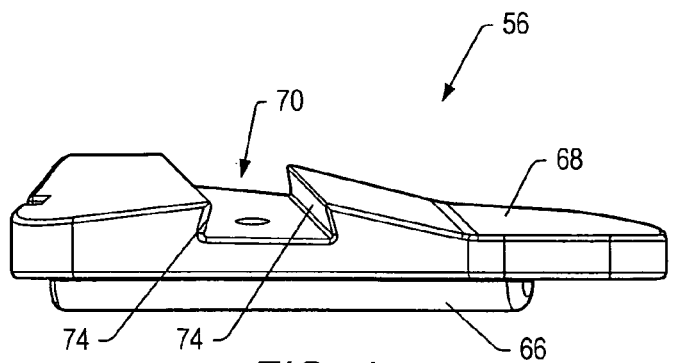
FIG. 4 depicts a side view of the first member of the dynamic interbody device embodiment.
Figure 5:
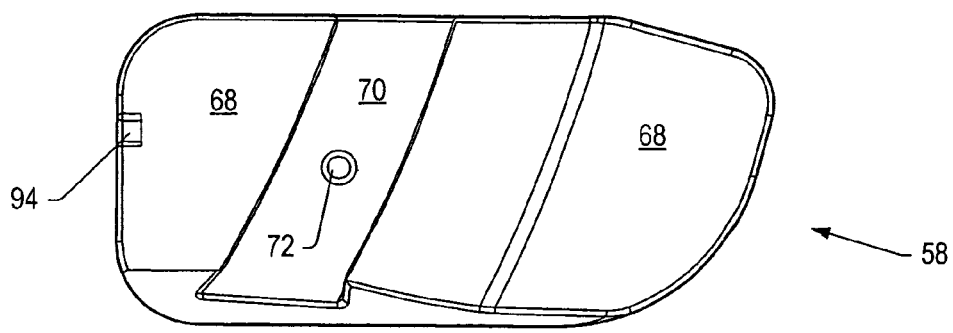
FIG. 5 depicts a top view of the first member of the dynamic interbody device embodiment.

FIG. 3 depicts a front view of first member 56 of dynamic interbody device 50'. FIG. 5 depicts a side view of first member 56 of dynamic interbody device 50'. FIG. 4 depicts a top view of first member 56 of dynamic interbody device 50'. First member 56 may include keel 66, superior surface 68, slot 70, and opening 72. Keel 66 may reside in a groove or recess formed in a vertebra when dynamic interbody device 50' is positioned in a disc space between vertebrae. Keel 66 may inhibit undesired movement of dynamic interbody device 50' relative to the vertebrae.

Superior surface 68 of first member 56 may be curved. The curvature of superior surface 68 may complement a curvature of an inferior surface of the second member of the dynamic interbody device to allow the dynamic interbody device to accommodate lateral bending.

First member 56 may include arcuate slot 70. Arcuate slot 70 may interact with a complementary protrusion of the second member to allow the dynamic interbody device to accommodate axial rotation. The curvature of superior surface 68 and arcuate slot 70 allows the dynamic interbody device to provide coupled lateral bending and axial rotation to vertebrae adjacent to the dynamic interbody device. In some embodiments, the second member may have an arcuate slot and the first member may have a complementary protrusion.

Arcuate slot 70 and the protrusion of the second member may be dovetailed or include another type of interconnection system that inhibits non-rotational separation of first member 56 from the second member when the protrusion of the second member is engaged in the slot of the first member. End surfaces 74 of arcuate slot 70 may interact with the end surfaces of the protrusion of the second member to resist shear load applied to the dynamic interbody device when the dynamic interbody device is positioned between vertebrae. End surfaces 74 and the end surfaces of the protrusion of the second member may be guides for lateral bending axial rotation of vertebrae coupled to the dynamic interbody device.

First member 56 may include opening 72 in slot 70. A pin may be positioned in opening 72. The pin may reside in a groove in the second member to define the maximum amount of lateral bending/axial rotation allowed by the dynamic interbody device. In other embodiments, a pin positioned in an opening in the second member may reside in a groove in the first member to define the maximum amount of lateral bending/axial rotation allowed by the dynamic interbody device.

Figure 6:
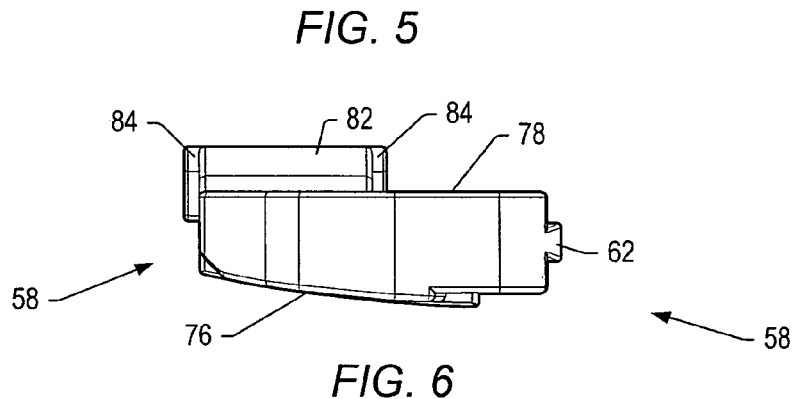
FIG. 6 depicts a front view of the second member of the dynamic interbody device embodiment.
Figure 7:
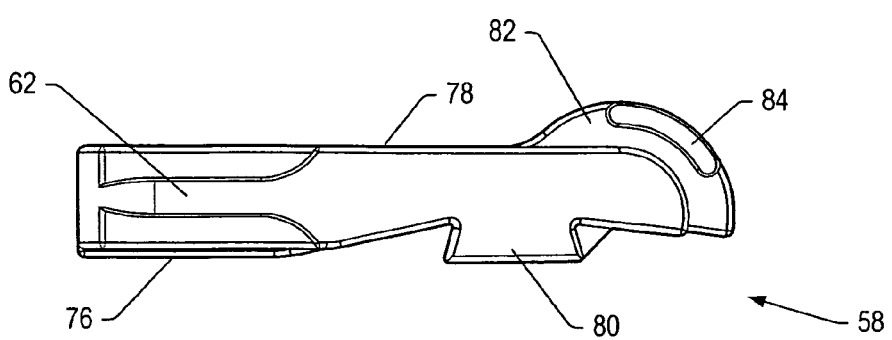
FIG. 7 depicts a side view of the second member of the dynamic interbody device embodiment.
Figure 8:
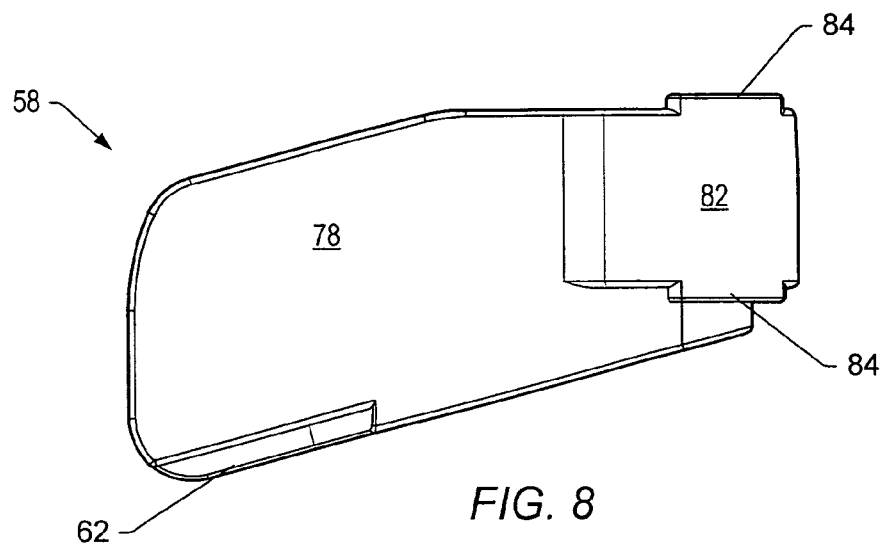
FIG. 8 depicts a top view of the second member of the dynamic interbody device embodiment.
Figure 9:
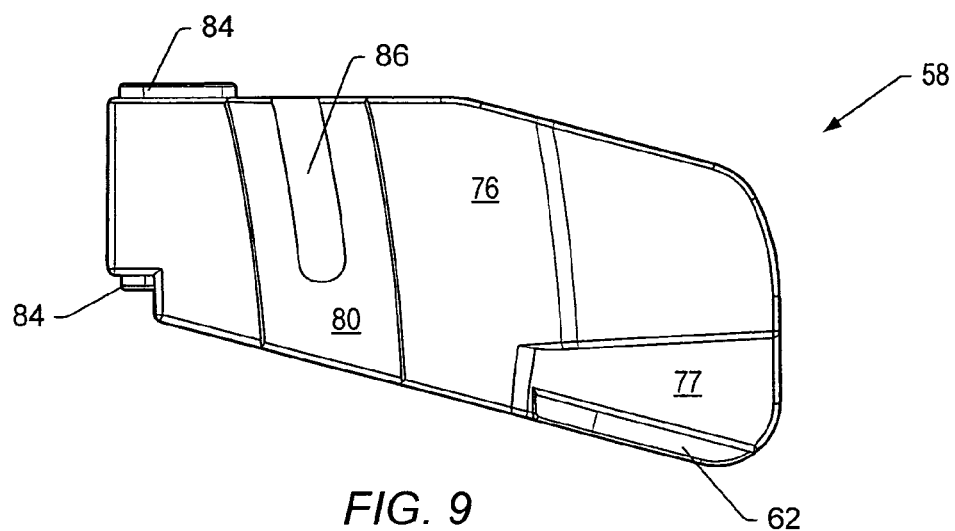
FIG. 9 depicts a bottom view of the second member of the dynamic interbody device embodiment.

FIG. 6 depicts a front view of second member 58 of dynamic interbody device 50'. FIG. 7 depicts a side view of first member 58 of dynamic interbody device 50'. FIG. 8 depicts a top view of first member 58 of dynamic interbody device 50'. FIG. 9 depicts a bottom view of second member 58 of dynamic interbody device 50'. Second member 58 may include inferior surface 76, recessed surface 77, superior surface 78, protrusion 80, bearing 82, tabs 84, groove 86, and portion 62. Some of inferior surface 76 may rest on the superior surface of the first member when protrusion 80 is placed in the arcuate slot of the first member. Inferior surface 76 may include a curvature that complements the curvature of the superior surface of the first member and protrusion 80 may complement the arcuate slot in the first member so that the dynamic interbody device is able to accommodate coupled lateral bending and axial rotation of vertebra joined to the dynamic interbody device.

Figure 10:
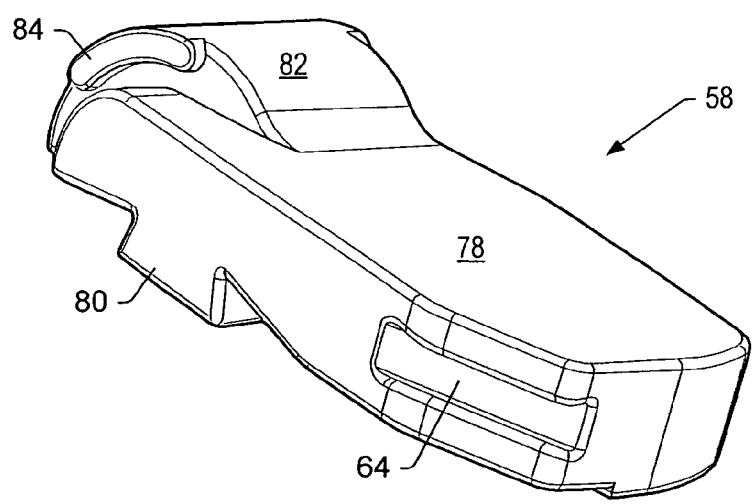
FIG. 10 depicts a perspective view of the second member of a dynamic interbody device.

Portion 62 of second member 58 of the dynamic interbody device (shown in FIG. 6) may engage a complementary portion of the second member of a second dynamic interbody device positioned adjacent to the dynamic interbody device when the dynamic interbody devices are positioned in a disc space between vertebrae. FIG. 10 depicts second member 58 with portion 64 that complements portion 62 of second member shown in FIG. 6. Engaging portion 62 with complementary portion 64 of the second dynamic interbody device may stabilize the dynamic interbody devices when the dynamic interbody devices are positioned between vertebrae. Coupling the dynamic interbody devices together with portions 62, 64 may assure that the second members of the dynamic interbody devices move in tandem relative to the first members of the dynamic interbody devices.

Coupling the dynamic interbody devices together with portions 62, 64 may inhibit migration of the dynamic interbody devices and/or subsidence of the vertebrae coupled to the dynamic interbody devices. Having complementary portions may require that a specific dynamic interbody device be installed prior to the other dynamic interbody device during an insertion procedure. For example, the dynamic interbody device with a female connection portion (i.e., portion 64 in FIG. 10) may need to be installed first. After insertion, migration and/or removal of the dynamic interbody devices is only possible by reversing the insertion order with the two dynamic interbody devices held in the same position as during insertion (i.e., neutral in axial rotation and lateral bending while in full flexion). Proper positioning of the two dynamic interbody devices may be determined by examining the position of the connected portions using imaging techniques before removal of the insertion instruments.

As shown in FIG. 7, second member 58 may include bearing 82. Bearing 82 may fit in a recess of the third member to allow the dynamic interbody device to accommodate flexion and extension of vertebra coupled to the dynamic interbody device. Bearing 82 may include tabs 84. Tabs 84 may fit in tracks in the third member to inhibit separation of second member 58 from the third member. To assemble the dynamic interbody device, the third member may be coupled to the second member. The second member may be coupled to the first member. The first member will inhibit separation of the third member from the second member even when the dynamic interbody device is subjected to the maximum amount of extension.

As shown in FIG. 9, groove 86 may be formed in protrusion 80 of second member 58. In some embodiments, groove 86 may be open at one side of second member 58. A pin in the first member may reside in groove 86 of the assembled dynamic interbody device.

Second member 58 may include recessed surface 77 in inferior surface 76. Recessed surface 77 may allow a portion of second member 58 to extend over a portion of the first member of the second dynamic interbody device without interference during lateral bending.

Figure 11:
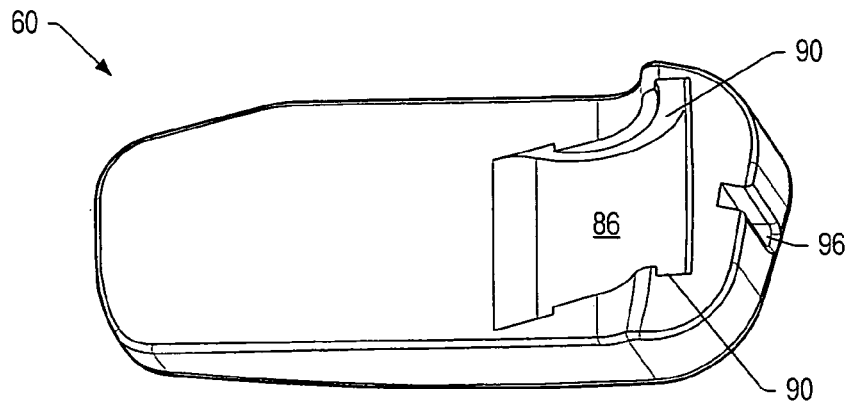
FIG. 11 depicts a perspective view of the third member of the dynamic interbody device with the second member depicted in FIGS. 6-9.

FIG. 11 depicts a perspective view that emphasizes bottom surface of third member 60. Third member 60 may include recess 88 with tracks 90. Recess 88 and tracks 90 may complement the bearing and tabs of the second member.

As shown in FIG. 2, first member 56 of each dynamic interbody device 50', 50" may include opening 92. Opening 92 may be a threaded opening or have another type of releasable coupling mechanism. Opening 92 may be used to releasably couple the dynamic interbody device to an insertion instrument. In other embodiments, openings for the insertion instrument may be located in the second member and/or the third member.

The dynamic interbody device may include one or more features that allow the insertion instrument to hold the dynamic interbody device in a desired position. For example, first member 56 may include slot 94 and third member 60 may include slot 96. A portion of the insertion instrument may be placed in slots 94, 96. The portion of the insertion instrument that fits in slots 94, 96 may place the dynamic interbody device in a desired position for insertion between vertebrae (i.e., neutral axial rotation, neutral lateral bending, and full flexion).

Figure 12:
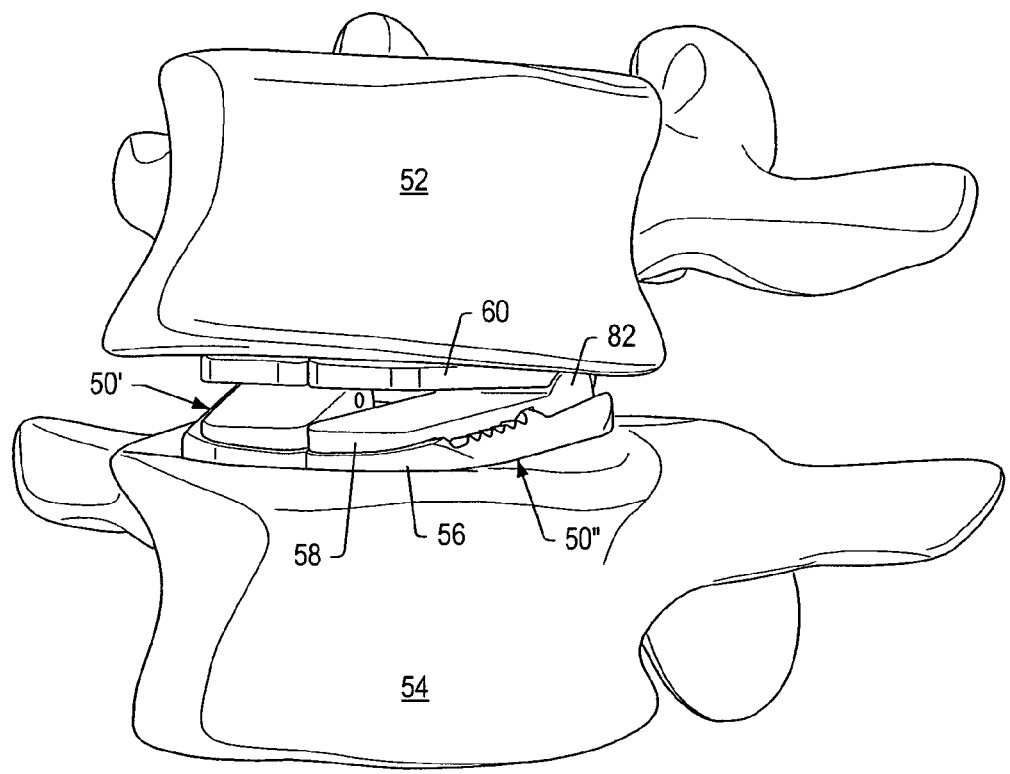
FIG. 12 depicts embodiments of dynamic interbody devices positioned between vertebrae.

FIG. 12 depicts alternate embodiments of dynamic interbody devices 50', 50" positioned between vertebra 52, 54. Each dynamic interbody device may include first member 56, second member 58 and third member 60. First member 56 and second member 58 may include complementary curved ridges that allow for coupled lateral bending and axial rotation of vertebrae 52, 54 that the dynamic interbody devices are positioned between. In some embodiments, the second member includes a guide recess. A guide pin of the first member resides in the guide recess to join the first member and the second member together and/or to limit the amount of axial rotation and lateral bending allowed by the dynamic interbody device. The first member may include undercut surfaces. The undercut surfaces of the first member may interact with undercut surfaces of the second member to inhibit separation of the first member from the second member and to take a portion of the shear load applied to the dynamic interbody device.

A tab of third member 60 may be placed in a slot of second member 58. A pin may be positioned in second member 58 through an opening in the slot to join the second member to third member 60. Second member 58 may include bearing 82. Third member 60 may include a recess with a curved surface that complements the curve of bearing 82. The coupling of the recess of third member 60 with the bearing of second member 58 may accommodate flexion and extension of vertebrae 52, 54 that dynamic interbody devices 50', 50" are positioned between.

Dynamic interbody devices 50', 50" work in conjunction to allow for coupled lateral bending and axial rotation and/or flexion/extension of vertebrae 52, 54 the dynamic interbody devices are positioned between. During an insertion procedure, careful positioning of the dynamic interbody devices 50', 50" may be needed to ensure that dynamic interbody device 50' works in conjunction with dynamic interbody device 50". In some dynamic interbody device embodiments, a separation angle of about 30° (i.e., each implant oriented at about 15° from a center line of endplate of the lower vertebra being stabilized) is desired between dynamic interbody devices 50', 50". Other embodiments of dynamic interbody devices may be designed to operate in conjunction with each other at other separation angles.

In some embodiments, insertion instruments may allow insertion of dynamic interbody devices 50', 50" so that ends of the dynamic interbody devices touch. Intra-operative imaging may be used to ensure the proper positioning and alignment of the dynamic interbody devices. In some embodiments, a portion of dynamic interbody device 50' may engage a portion of dynamic interbody device 50" to ensure proper positioning of the dynamic interbody devices 50', 50". For example, a dovetailed portion of dynamic interbody device 50' fits in a complementary groove of dynamic interbody device 50" when the dynamic interbody devices are properly positioned. Engaging dynamic interbody devices may inhibit migration of the dynamic interbody devices after insertion.

Figure 13:
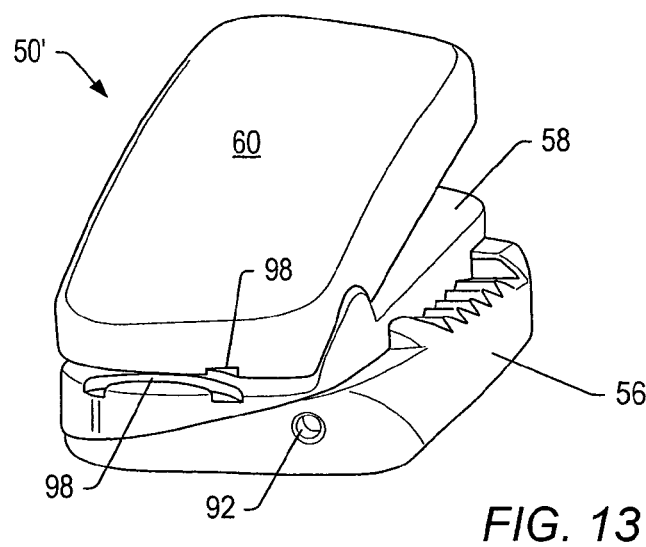
FIG. 13 depicts the posterior end of an embodiment of a dynamic interbody device.

FIG. 13 depicts the posterior end of dynamic interbody device 50' when there is no lateral bending or axial rotation of second member 58 of the dynamic interbody device relative to first member 56. In some embodiments, first member 56 may be wider than second member 58 and third member 60. First member 56 may abut the lower vertebra of the vertebrae to be stabilized. Having the first member wider than second member 58 and/or third member 60 may take advantage of the space available for insertion of the dynamic interbody devices between the vertebrae.

In many previous devices inserted using a posterior approach, the width of the portion of the device that contacted the upper vertebra was substantially the same as the width of the portion of the device that contacted the lower vertebra. The width of devices was typically the largest width that allowed insertion of the portion of the device that contacted the upper vertebra without undue retraction of neural structures exiting between the vertebrae. The space available for insertion of a device using a posterior approach is typically wider near the lower vertebra and becomes less wide nearer the upper vertebra.

In some embodiments, second member 58 and third member 60 may include curved dovetailed slots 98. Slots 98 may accept a first portion of an inserter. When the first portion of the inserter is coupled to slots 98 of second member 58 and third member 60, movement of the second member relative to the third member (e.g., flexion/extension) is inhibited. First member 56 may include inserter opening 92. Inserter opening 92 may be threaded. A second portion of the inserter may fit in inserter opening 92. When the first portion of the inserter is coupled to slots 98 and the second portion of the inserter is positioned in inserter opening 92, movement of first member 56 relative to second member 58 is inhibited.

The first member of the dynamic interbody device may be wider than the third member to take advantage of the available insertion space for the dynamic interbody devices. Having first members with large widths provides large contact area between the first members and the lower vertebra. The large contact area may inhibit subsidence of the vertebra that is more likely to subside due to the presence of the dynamic interbody devices. Even though third member may be less wide than first member, the third member provides sufficient contact against the upper vertebra to inhibit subsidence of the upper vertebra.

Pairs of dynamic interbody devices having different widths, lengths, and/or heights may be provided in the instrument kit for the spinal stabilization procedure. For example, the instrument kit may include pairs of implants having small widths, medium widths, and large widths of different heights and/or lengths.

In some embodiments, a dynamic interbody device or dynamic interbody devices may not allow coupled axial rotation and lateral bending of vertebrae adjacent to the dynamic interbody device or dynamic interbody devices. For example, in an embodiment, the curvature of ridges in the first member and second member of the dynamic interbody device only allows for axial rotation of vertebrae adjacent to the dynamic interbody device without allowing for lateral bending. The interaction of the first member with the second member allows for axial rotation and resists at least a portion of the shear load applied by the vertebrae to the dynamic interbody device. In an embodiment, the curvature of ridges in the first member and the second member allow for lateral bending of vertebrae adjacent to the dynamic interbody device without allowing for axial rotation. The interaction of the first member with the second member allows for lateral bending and resists at least a portion of the shear load applied by the vertebrae to the dynamic interbody device.

Figure 14:
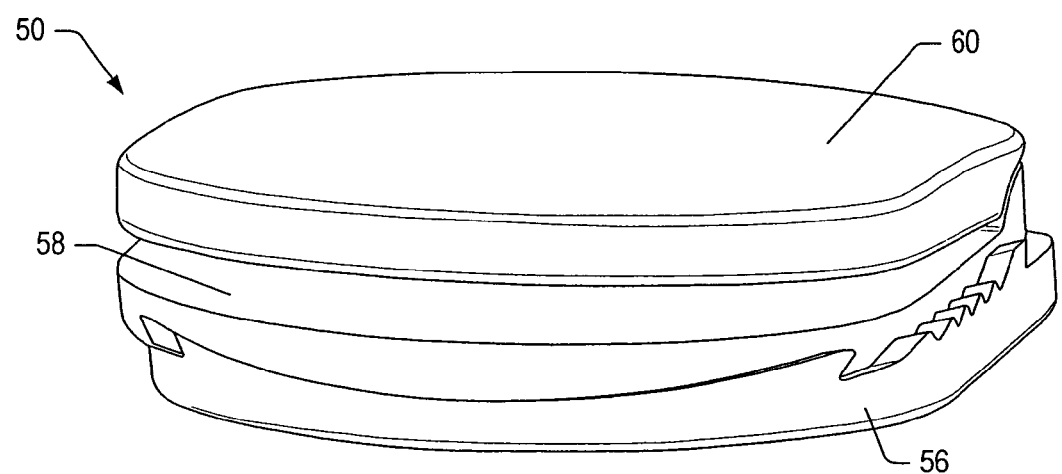
FIG. 14 depicts a perspective view of an embodiment of a dynamic interbody device.

In some embodiments, a single dynamic interbody device may be used. FIG. 14 depicts a perspective view of dynamic interbody device 50 emphasizing the anterior side and the superior surface. Dynamic interbody device 50 is shown with some axial rotation and lateral bending from a neutral position. Dynamic interbody device 50 may be placed in a disc space between two vertebrae using an anterior approach. The width of the dynamic interbody device may be greater that one half the width of the vertebrae the dynamic interbody device is to be positioned between. The width of the dynamic interbody device may be substantially the same as the width of the vertebrae the dynamic interbody device is to be positioned between. Dynamic interbody device 50 may include first member 56, second member 58, and third member 60. Dynamic interbody device 50 may be a bilateral device with coupled axial rotation and lateral bending. First member 56 may be coupled to second member 58 so that dynamic interbody device 50 accommodates lateral bending and axial rotation of vertebrae coupled to dynamic interbody device 50. As with a natural functional spinal unit, dynamic interbody device 50 couples lateral bending and axial motion together so that lateral bending motion causes axial rotation, and axial rotation causes lateral bending. Third member 60 may be coupled to second member 58 so that dynamic interbody device 50 accommodates flexion and extension of vertebrae coupled to the dynamic interbody device.

The superior surface may be coupled to an upper vertebra of the vertebrae to be stabilized. An inferior surface of the dynamic interbody device may be coupled to the lower vertebra of the vertebrae to be stabilized. At least a portion of the superior surface may be positioned near the edge of the endplate of the upper vertebra so that the dynamic interbody device abuts strong, supportive bone of the upper vertebra. At least a portion of the inferior surface may be positioned near the edge of the endplate of the lower vertebra so that the dynamic interbody device abuts strong, supportive bone of the lower vertebra.

Figure 15:
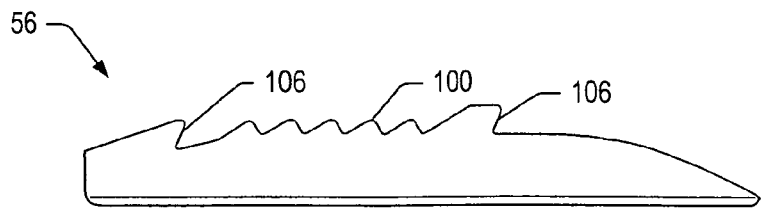
FIG. 15 depicts a side view of a first member of the dynamic interbody device depicted in FIG. 14.
Figure 16:
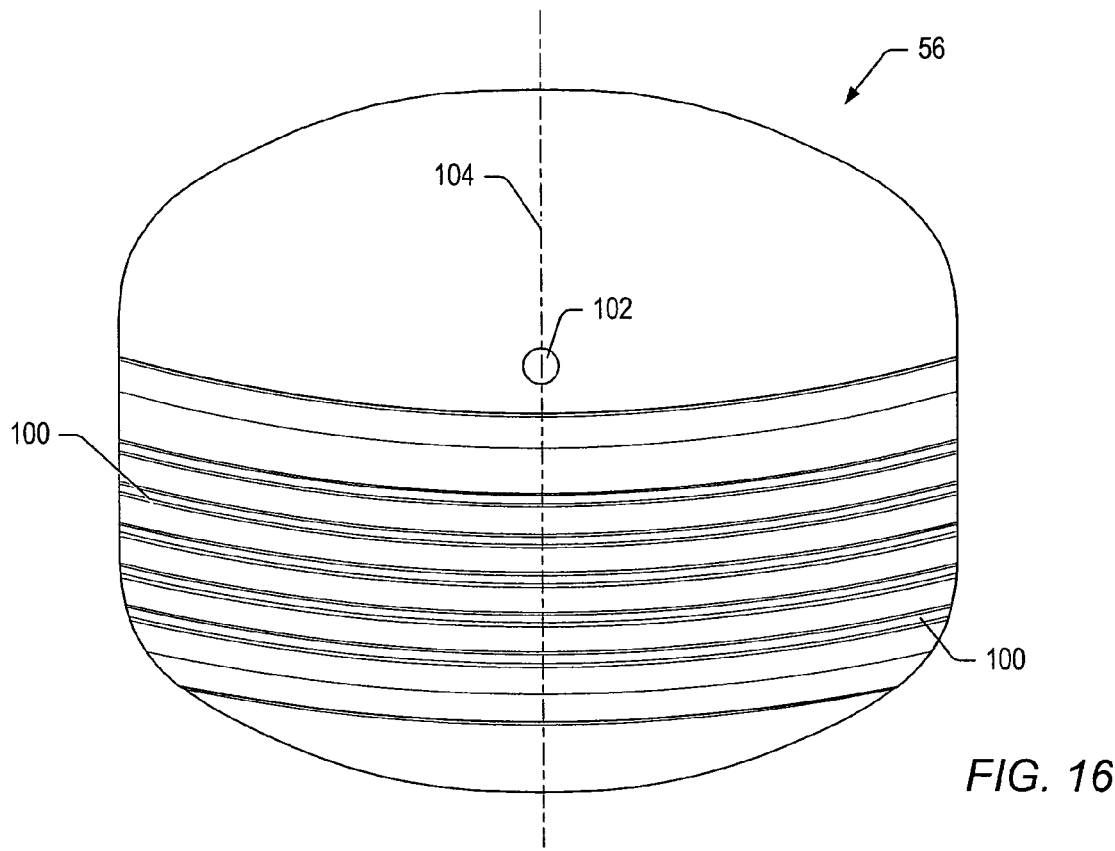
FIG. 16 depicts a top view of the first member of the dynamic interbody device depicted in FIG. 14.

FIG. 15 depicts a side view of first member 56 and FIG. 16 depicts a top view of the first member. First member 56 may include ridges 100 and pin opening 102. Ridges 100 and the grooves between the ridges may mate with corresponding grooves and ridges of the second member so that the dynamic interbody device accommodates coupled lateral bending and axial rotation. As depicted in FIG. 16, ridges 100 may be curved. The curvature allows the dynamic interbody device to accommodate axial rotation. Ridges 100 may be symmetrical about center line 104 of first member 56 so that the dynamic interbody device accommodates the same amount of clockwise axial rotation as counterclockwise axial rotation. In some embodiments, the ridges and grooves may not be symmetrical about the centerline so that the dynamic interbody device allows no or limited axial rotation in a particular direction to accommodate the needs of a patient.

A guide pin may be press fit or otherwise secured in pin opening 102 after the second member is coupled to first member 56. The guide pin may fit in a guide recess in the second member. The guide pin may limit the amount of lateral bending and axial rotation allowed by the dynamic interbody device and/or inhibit separation of first member 56 from the second member. In some embodiments, the first member may have a guide recess and a guide pin may positioned in the second member may reside in the guide recess.

As seen in FIG. 15, first member 56 may include one or more undercut surfaces 106. Undercut surfaces 106 may inhibit separation of the second member from first member 56 when the second member is coupled to the first member. Undercut surfaces 106 may share a portion of the load applied to the dynamic interbody device.

Figure 17:
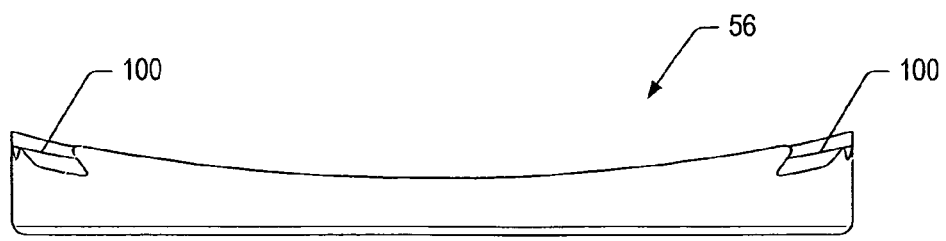
FIG. 17 depicts a front view of the first member of the dynamic interbody device depicted in FIG. 14.

FIG. 17 depicts a front view of first member 56. First member 56 may decrease in height from a position at or near the right side of the first member to the center of the first member. The first member 56 may increase in height from the center to a position near or at the left side of the first member. At least a portion of first member 56 has a concave shape. The concave shape of at least a portion of first member 56 may allow the dynamic interbody device to accommodate lateral bending of vertebrae coupled to the dynamic interbody device.

Figure 18:
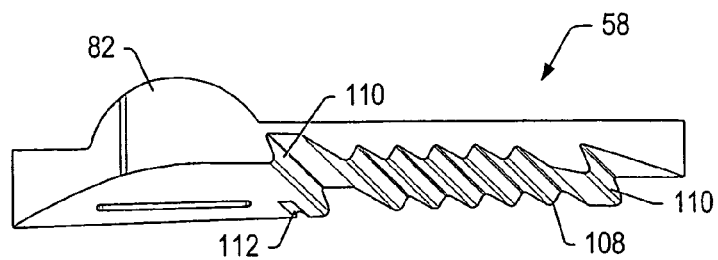
FIG. 18 depicts a side view of the second member of the dynamic interbody device depicted in FIG. 14.

FIG. 18 depicts a side view of second member 58. The bottom of second member 58 may include ridges 108, one or more undercut surfaces 110, and guide recess 112. Ridges 108 may be curved and the bottom of second member 58 may have a convex shape so that the ridges of the second member mate with the grooves between the ridges of the first member, and the ridges of the first member mate with the grooves between the ridges of the second member. Undercut surfaces 110 may interact with the undercut surfaces of the first member to inhibit separation of second member 58 from the first member when the dynamic interbody device is assembled. An end of the guide pin placed in the pin opening of the first member may reside in guide recess 112 of second member. The guide pin may limit the range of motion for axial rotation and lateral bending of the assembled dynamic interbody device and inhibit separation of the first member from second member 58.

Second member 58 may include bearing 82. Bearing 82 may fit in a recess in the third member so that the assembled dynamic interbody device is able to accommodate flexion and/or extension of vertebrae coupled to the dynamic interbody device. Other connection systems between the second member and the third member that accommodate flexion/extension of vertebrae coupled to the dynamic interbody device may also be used.

In some embodiments, the second member includes a bearing recess and the third member includes a bearing that fits in the recess. Bearing 82 may be located towards a posterior end of the dynamic interbody device. Locating bearing 82 near the posterior end of the dynamic interbody device locates the axis of rotation for flexion/extension close to the natural axis of rotation for flexion/extension of the vertebrae. The curvature of bearing 82 may be relative small to limit translational movement of the third member relative to second member during flexion/extension.

Figure 19:
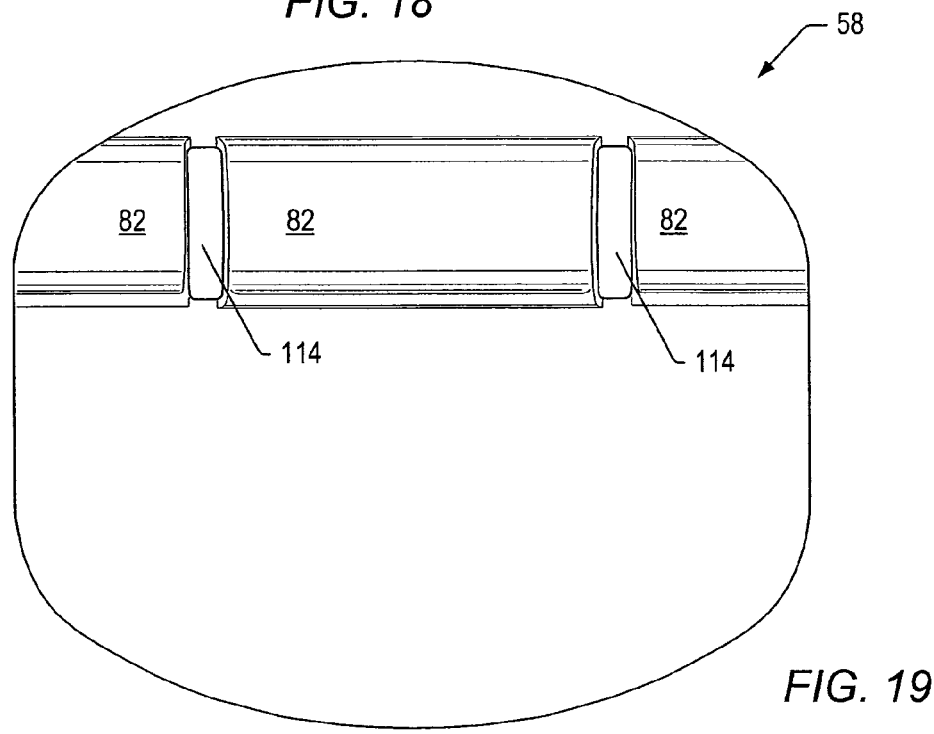
FIG. 19 depicts a top view of the second member of the dynamic interbody device depicted in FIG. 14.

FIG. 19 depicts a top surface of second member 58. Second member 58 may include slots 114. Tabs of the third member may be positioned in slots 114. One or more pins positioned in bearing 82 of second member 58 and through the tabs of the third member may couple the second member to the third member. When the dynamic interbody device is positioned between vertebrae, fluid may enter the slots and keep the dynamic interbody device lubricated.

In some embodiments, the second member of the dynamic interbody device may have a protrusion and the first member may have a complementary slot instead of a plurality of complementary ridges and grooves. In some embodiments, the second member of the dynamic interbody device may have a slot and the first member may have a complementary protrusion instead of a plurality of complementary ridges and grooves in the second member and the first member.

Figure 20:
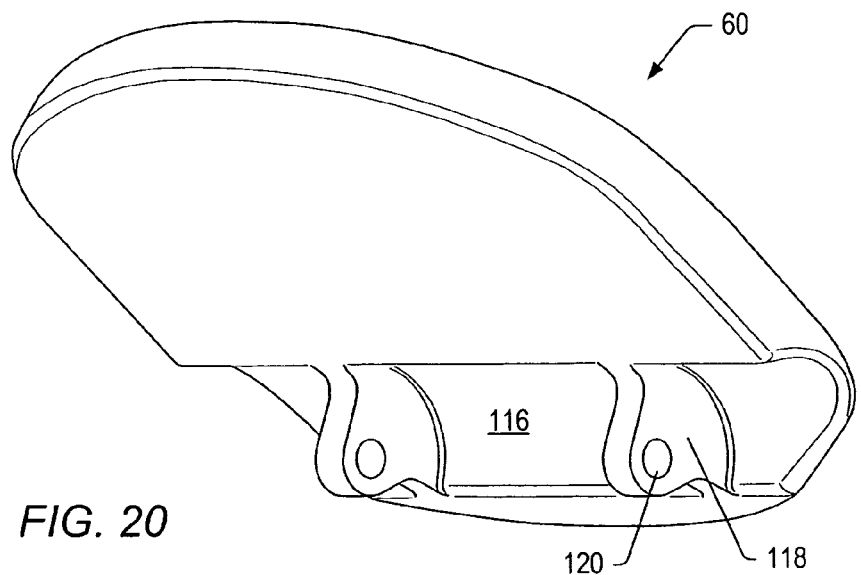
FIG. 20 depicts a perspective view of the third member of the dynamic interbody device depicted in FIG. 14.

FIG. 20 depicts a perspective view of third member 60 that emphasizes a bottom surface of the third member. Third member 60 may include recess 116 and tabs 118. Recess 116 may be complementary to the bearing of the second member so that the assembled dynamic interbody device allows for flexion/extension of vertebrae coupled to the dynamic interbody device. Tabs 118 may be positioned in the slots of the second member. A pin or pins positioned through openings 120 in tabs 118 may couple third member 60 to the second member.

In some embodiments, the front faces of the first member, second member and/or third member may include indentions, openings, or other surface features for connecting the dynamic interbody device to an inserter. The connection between the dynamic interbody device and the inserter allows force to be applied substantially evenly to the dynamic interbody device to facilitate insertion of the dynamic interbody device into the disc space. The inserter may maintain the position of the first member relative to the second member and the third member during insertion.

The ridges of the first member are complementary to the ridges of the second member. When the dynamic interbody device is positioned between vertebrae, the vertebrae exert compressive and/or shear forces on the dynamic interbody device. Having a number of ridges increases the surface area for dissipating force applied to the dynamic interbody device. Increasing the surface area for dissipating force applied to the dynamic interbody device may reduce pressure and decrease wear of the dynamic interbody device.

A front part of the third member may rotate towards the second member to accommodate flexion. The front part of the third member may rotate away from the second member to accommodate extension.

Figure 21:
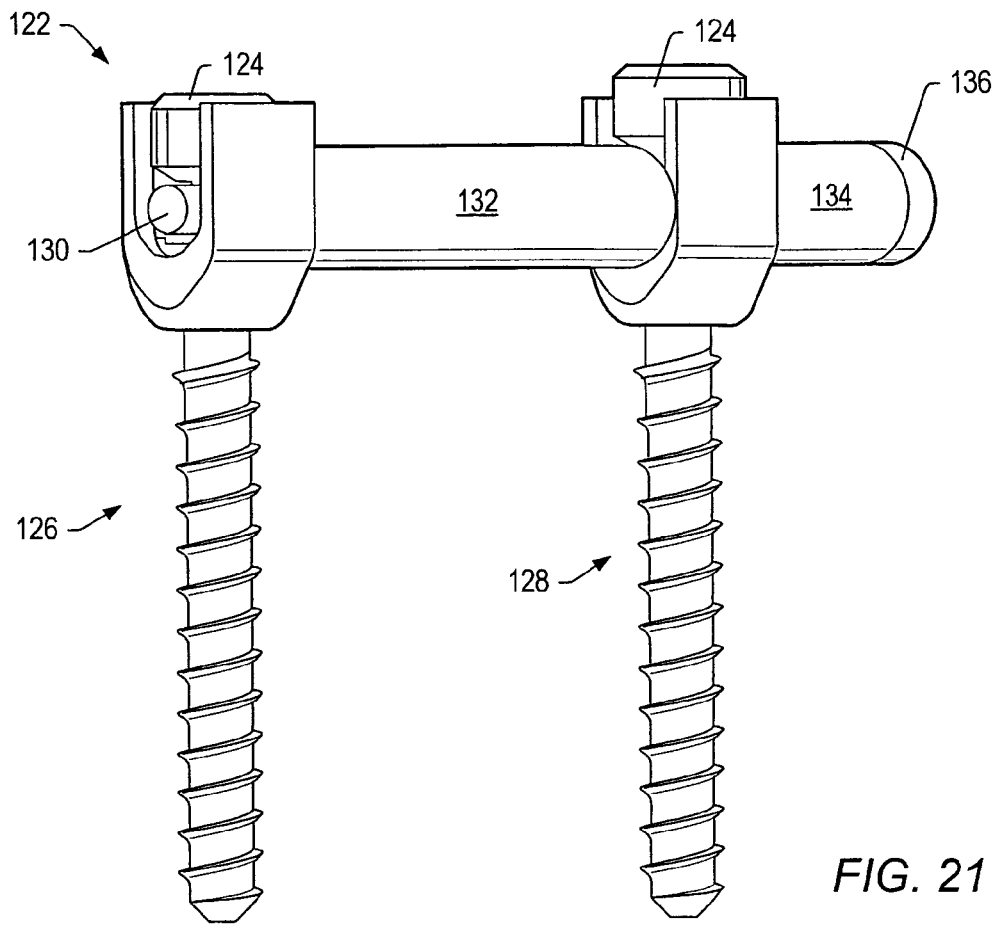
FIG. 21 depicts a perspective view of an embodiment of a posterior stabilization system.

FIG. 21 depicts an embodiment of dynamic posterior stabilization system 122. Dynamic posterior stabilization system 122 may include closure members 124; first bone fastener 126; second bone fastener 128; elongated member 130; bias members 132, 134; and stop 136. In some embodiments, first bone fastener 126 is positioned in the upper vertebra of the vertebrae to be stabilized. In other embodiments, first bone fastener is positioned in the lower of the vertebrae to be stabilized.

When closure member 124 couples elongated member 130 to first bone fastener 126, movement of the elongated member relative to the first bone fastener may be inhibited. When closure member 124 couples elongated member 130 to second bone fastener 128, translational and/or rotational movement of the elongated member relative to the second bone fastener may be possible. The ability to have translational movement of elongated member 130 relative to second bone fastener 128 may allow dynamic posterior stabilization system 122 to accommodate flexion, extension and lateral bending of a first vertebra coupled to the dynamic posterior stabilization system relative to a second vertebra coupled to the dynamic posterior stabilization system. The ability to have rotational movement of elongated member 130 relative to second bone fastener 128 may allow dynamic posterior stabilization system 122 to accommodate axial rotation of the first vertebra coupled to the dynamic posterior stabilization system relative to the second vertebra coupled to the dynamic posterior stabilization system.

Figure 22:
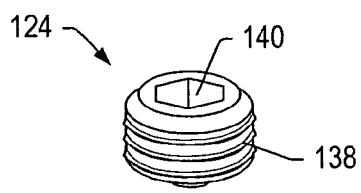
FIG. 22 depicts a perspective view of an embodiment of a closure member.

FIG. 22 depicts an embodiment of closure member 124. Closure member 124 may couple the elongated member of the dynamic posterior stabilization system to the first bone fastener or to the second bone fastener. Closure member 124 may include threading 138 or other structure that secures the closure member to a collar of the first bone fastener 126 or to a collar of the second bone fastener. Closure member 124 may include tool opening 140. A portion of a driver may be inserted into tool opening 140 to facilitate attaching closure member 124 to the collar of the first bone fastener or to the collar of the second bone fastener.

Closure members may be other types of fasteners, including but not limited to clips and snap on connectors. In some embodiments, the closure member coupled to the first bone fastener may be different from the closure member coupled to the second bone fastener. For example, the closure member used to secure the elongated member to the first bone screw may be a closure member as depicted in FIG. 22, while a closure member used to couple the elongated member to the second bone fastener may be a clip that allows the elongated member to move relative to the second bone fastener.

As shown in FIG. 21, dynamic posterior stabilization system 122 includes elongated member 130. Elongated member 130 may be a rod, bar, plate, combination thereof, or other type of member coupled to first bone fastener 126 and second bone fastener 128. In some embodiments where the dynamic posterior stabilization system is to be used with a dynamic interbody device, elongated member 130 may be bent so that the elongated member has a curvature that facilitates the use of the dynamic posterior stabilization system in conjunction with the dynamic interbody device. In embodiments where the dynamic posterior stabilization system is not used in conjunction with a dynamic interbody device, the elongated member may be straight or curved. Elongated members with appropriate curvature may be included in the instrument kit for the spinal stabilization procedure.

Figure 23:
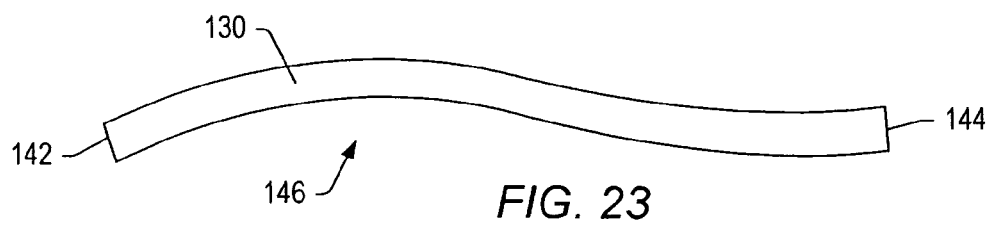
FIG. 23 depicts a side view of an embodiment of an elongated member.

FIG. 23 depicts an embodiment of bent elongated member 130. In an embodiment, a portion of elongated member 130 near first end 142 is secured to the first bone fastener of the dynamic posterior stabilization system so that movement of the elongated member relative to the first bone fastener is inhibited. A portion of elongated member 130 near second end 144 may be coupled to the second bone fastener of the dynamic posterior stabilization system so that translational movement and or rotational movement of the elongated member relative to the second bone fastener is allowed. In some embodiments, concave portion 146 of elongated member 130 may be oriented to face the vertebrae coupled to the dynamic posterior stabilization system. In some embodiments, a portion of elongated member 130 near second end 144 may be bent so that the elongated member does not contact or approach a vertebra during patient movement.

As shown in FIG. 21, an end of elongated member 130 near second bone fastener 128 may include stop 136. Stop 136 may retain bias member 134 on elongated member 130. In some embodiments, the position of stop 136 may be adjustable along the length of the elongated member. A fixed position stop or an adjustable position stop may be used in conjunction with bias member 132 instead of using the collar of first bone fastener 126 as the stop for bias member 132. In some embodiments, a removable stop may initially maintain bias member 132 in compression. In some embodiments, a removable stop may initially maintain bias member 132 in compression. The removable stops may facilitate coupling elongated member 130 to second bone fastener 128. After elongated member 130 is coupled to second bone fastener 128, the removable stops may be removed so that the bias members can accommodate movement of the elongated member relative to the second bone fastener caused by flexion/extension and/or lateral bending. In some embodiments, an insertion instrument may hold bias members 132, 134 in compression when elongated member 130 is being coupled to first bone fastener 126 and second bone fastener 128.

Bias members 132, 134 may surround or partially surround elongated member 130. Bias members 132, 134 may be stacks of elastic washers, elastic tubes, springs, or other systems that provide resistance to compression. In some embodiments, bias members 132, 134 may be formed of biocompatible polymeric material. For example, bias members 132, 134 may be formed of silicone-urethane co-polymer.

Bias members 132, 134 may transmit little or no force to second bone fastener 128 when dynamic posterior stabilization system 122 is in a neutral position. If second bone fastener 128 is coupled to the more caudal vertebra of the vertebrae to be stabilized, compression of bias member 132 may accommodate translational movement of elongated member 130 caused by extension and/or lateral bending of the vertebrae coupled to dynamic posterior stabilization system 122. If second bone fastener 128 is coupled to the more caudal vertebra of the vertebrae to be stabilized, compression of bias member 134 may accommodate translational movement of elongated member 130 caused by flexion and/or lateral bending of the vertebrae coupled to dynamic posterior stabilization system 122.

Bias member 132 may accommodate up to about 3 mm of travel of second bone fastener 128 towards first bone fastener 126. Bias member 134 may accommodate up to about 2 mm of travel of second bone fastener 128 away from first bone fastener 126.

In some embodiments, bias member 132 and bias member 134 are the same. For example, bias members 132, 134 may be stacks of washers. In some embodiments, bias member 132 is different than bias member 134. For example, bias member 132 is a spring, and bias member 134 is an elastic tube.

Figure 24:
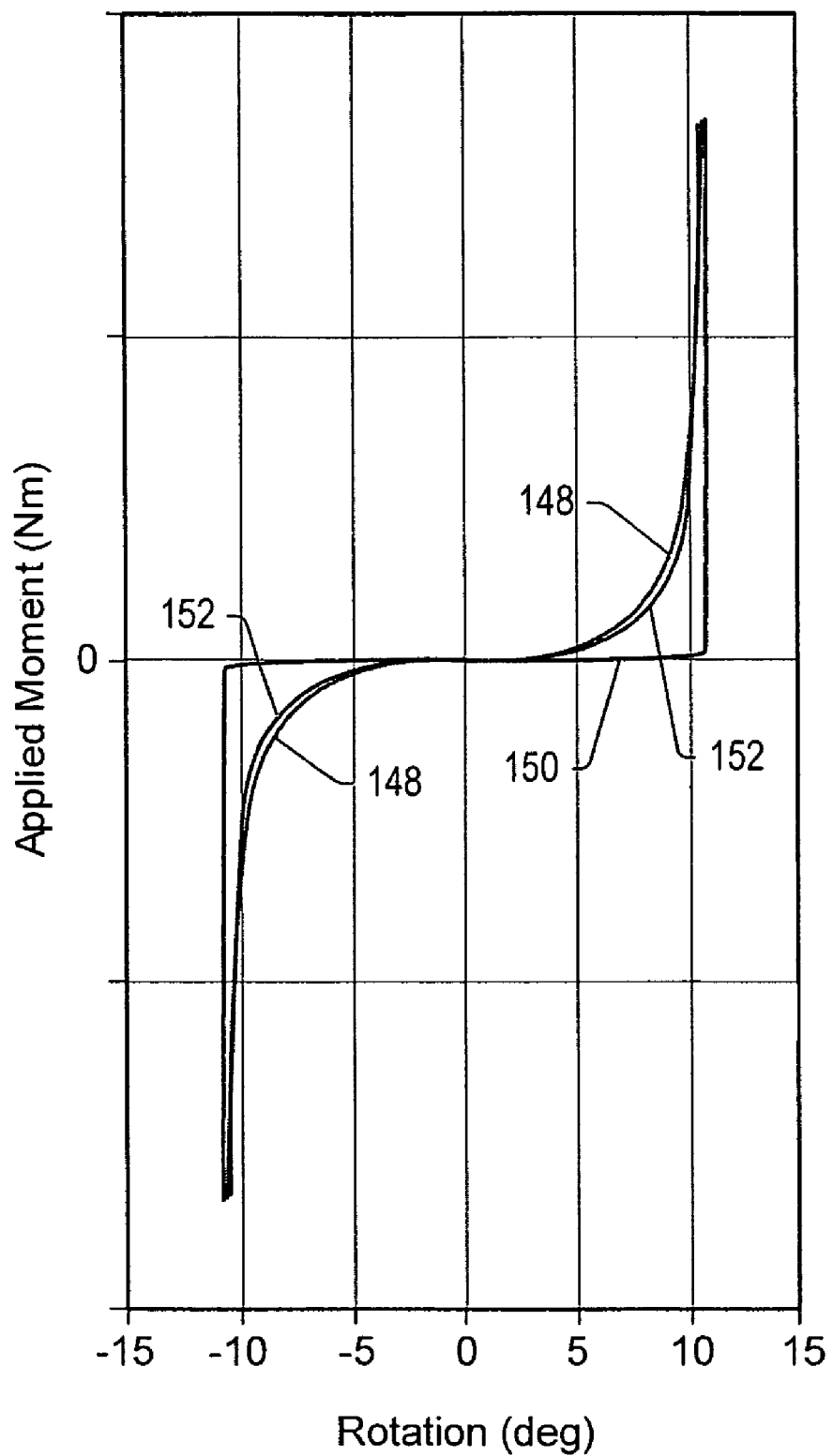
FIG. 24 depicts a plot of applied moment versus rotation.

Bias members 132, 134 may allow dynamic posterior stabilization system 122 to provide stability while still allowing for anatomical motion and dynamic resistance that mimics normal segmental stiffness of the spine. Knowledge of the elastic properties (e.g., the amount of compression per degree of rotation) of the material chosen for bias members 132, 134 allows the length of the bias members placed on the elongated member to be selected so that the dynamic posterior stabilization system provides a desired amount of resistance. FIG. 24 depicts a plot of the applied moment versus the amount of rotation for an intact (normal) functional spinal unit (plot 148), for an unconstrained functional spinal unit (plot 150), and for a functional spinal unit with a dynamic posterior stabilization system (plot 152). The slope of the curves at each point represents spinal stiffness. The neutral zone is the low stiffness region of the range of motion. The dynamic posterior stabilization system may allow for stabilization of the spine while providing substantially unconstrained motion within the neutral zone and increasing resistance to rotation within the elastic zone. The stiffness of vertebrae supported by the dynamic posterior stabilization system may closely mimic the stiffness of a normal functional spinal unit. The behavior of the dynamic posterior stabilization system may closely mimic the normal kinematics of the functional spinal unit.

FIG. 25 depicts the components of an embodiment of first bone fastener 126. First bone fastener 126 may include fastener 154, collar 156, and saddle 158. Fastener 154 may include shaft 160 and head 162. Shaft 160 may secure first bone fastener 126 to bone (e.g. a vertebra). Shaft 160 may include threading 164 that secures the shaft to the bone.

A portion of outer surface 166 of head 162 may have a spherical contour complementary to a portion of spherically contoured inner surface 168 of collar 156. The shape of outer surface 166 and inner surface 168 of collar 156 may allow for polyaxial positioning of the collar relative to fastener 154. Inner surface 170 of head 162 may be spherically contoured. The spherical contour of inner surface 170 may allow saddle 158 to be positioned in fastener 154 at a desired angle to accommodate the position of collar 156 relative to the fastener.

Collar 156 may include arms 172 and lower body 174. A portion of the elongated member may be positioned in the slot between arms 172. A portion of the inner surfaces of arms 172 may include threading 176 that is complementary to threading of the closure member used to secure the elongated member to first bone fastener 126. Portion 168 of the inner surface of lower body 174 may have a spherically contoured section that complements the spherical contour of outer surface 166 of fastener head 162 to allow for polyaxial positioning of collar 156 relative to fastener 154.

Head 162 of fastener 154 may be positioned in collar 156 to form a fastener and collar combination. FIG. 26 depicts a top view of fastener and collar combination 178. When head 162 is positioned in collar 156, separation of the fastener from the collar may be difficult. Several fastener and collar combinations 178 may be provided in an instrument kit for a dynamic spinal stabilization procedure. The instrument kit may include several combinations 178 with fasteners 154 of varying lengths. For example, the kit may include fastener and collar combinations with fastener having lengths from about 30 mm to about 75 mm in 5 mm increments. In some embodiments, collar 156 of each combination 178 is stamped, printed or etched with the length of fastener 154. Fasteners 154 and/or collars 156 of combinations 178 in the instrument kit may be color coded to indicate the length of the fasteners. For example, the collars of all combinations in the instrument kit with fasteners 154 that are about 30 mm in length have an orange color, the collars of all combinations in the instrument kit with fasteners that are about 35 mm in length have a yellow color, and the collars of all combinations with fasteners that are about 40 mm in length have a green color. Additional colors may be used for additional sizes.

Fastener 154 may include tool opening 180. Tool opening 180 may complement a head of a driver. The driver may be used to insert fastener 154 into bone. The driver may be included in the instrument kit for the spinal stabilization procedure. In some embodiments, arms 172 may include flats, recesses or openings that engage insertion tools or guides.

Referring to FIG. 25, saddle 158 may have post 182 and support 184. Saddle 158 may be positioned in fastener 154 after the fastener and collar combination has been inserted into a vertebra. Post 182 may be positioned in fastener 154. Post 182 may be angled within head 162 of fastener 154 so that saddle 158 can accommodate polyaxial positioning of collar 156 relative to the fastener. In some embodiments, a retaining ring inhibits separation of saddle 158 from fastener 154.

Support 184 may include groove 186. A portion of the elongated member of the dynamic posterior stabilization system may be positioned in groove 186. In some embodiments, saddle 158 and/or collar 156 are shaped so that groove 186 aligns with the slot formed between arms 172 of collar 156 when the saddle is placed in the collar.

A portion of the elongated member may be positioned in groove 186. The closure member for first bone fastener 126 may be threaded on collar 156 and tightened against elongated member 130. In some embodiments, the closure member may include one or more points or edges that bite into the elongated member when the closure member is tightened against the elongated member. When the closure member is tightened against the elongated member, the position of collar 156 relative to fastener 154 may become fixed, and movement of the elongated member relative to first bone fastener may be inhibited.

FIG. 27 depicts an embodiment of second bone fastener 128. Second bone fastener 128 may include fastener 154, collar 156, saddle 158, and cover 188. Fastener 154, collar 156, and saddle 158 of second bone fastener 128 may be substantially the same as the fastener, collar and saddle of the first bone fastener. Cover 188 may include groove 190.

Saddle 158 may be positioned in collar 156 after the fastener and collar combination are inserted into a vertebra. A portion of the elongated member may be positioned in groove 186 of saddle 158. Cover 188 may be positioned on top of the elongated member. The radius of groove 190 may be larger than the radius of the portion of the elongated member positioned in the groove. The closure member for second bone fastener 128 may be threaded on collar 156 and tightened against cover 188. In some embodiments, the closure member may include one or more points or edges that bite into cover 188 when the closure member is tightened against the cover. The position of collar 156 relative to fastener 154 may become fixed when the closure member is tightened against cover 188. Having the radius of groove 190 larger than the radius of the portion of the elongated member positioned in the groove may allow translational movement and/or rotational movement of the elongated member relative to second bone fastener 128 when the closure member couples the elongated member to the second bone fastener.

When a closure member secures the elongated member between saddle 158 and cover 188, significant change in height of the elongated member relative to second bone fastener 128 may be inhibited. Inhibiting height change of the elongated member relative to second bone fastener may allow the dynamic posterior stabilization system to share a portion of the shear load applied to a dynamic interbody device or intervertebral disc between the vertebrae being stabilized.

Figure 28:
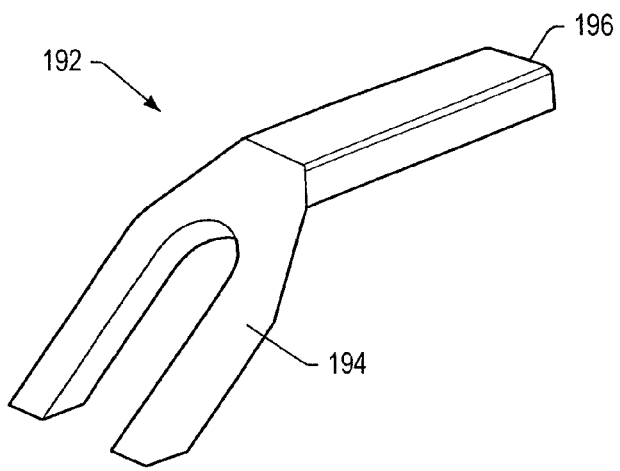
FIG. 28 depicts a perspective view of an embodiment of a bridge.

In some embodiments, a bridge may be coupled to a bone fastener of the dynamic posterior stabilization system. FIG. 28 depicts an embodiment of bridge 192. Bridge 192 may include connector 194, and end 196. Connector 194 may be coupled to the bone fastener inserted into the lower vertebra of the vertebrae being stabilized. Coupling bridge to the lower vertebra may inhibit contact of the bridge with neural structures exiting the vertebrae. End 196 may contact the dynamic interbody device positioned between vertebrae during use to inhibit posterior migration and/or backout of the dynamic interbody device from the disc space.

Figure 29:
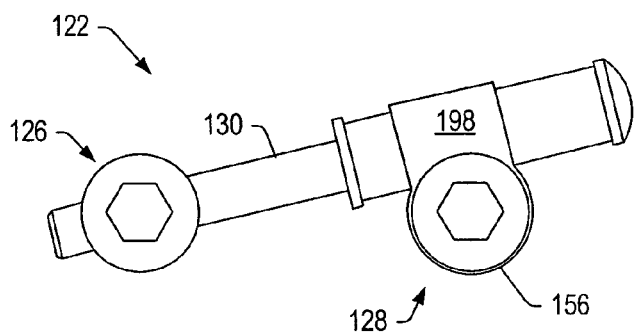
FIG. 29 depicts an embodiment of a dynamic posterior stabilization system with a laterally positioned elongated member.

In some dynamic posterior stabilization system embodiments, the elongated member may be positioned lateral to the first bone fastener and/or the second bone fastener. FIG. 29 depicts a top view representation of an embodiment of dynamic posterior stabilization system 122 where elongated member 130 is positioned lateral to second bone fastener 128. A closure member may secure elongated member 130 to first bone fastener 126 so that movement of the elongated member relative to the first bone fastener is inhibited.

Second bone fastener 128 may include member 198. A portion of member may slide over or into a portion of collar 156 of second bone fastener 128. The connection between the collar and member may inhibit rotation of member 198 relative to collar 156. A closure member may secure member 198 to collar 156 and second bone fastener 128. When the closure member secures member 198 to collar 156 movement of second bone fastener 128 relative to elongated member 130 is allowed. Second bone fastener 128 may be able to move axially relative to elongated member 130 to accommodate flexion/extension and/or lateral bending of vertebrae coupled to the dynamic posterior stabilization system. Second bone fastener 128 may also be able to rotate relative to elongated member 130 to accommodate axial rotation of vertebrae coupled to the dynamic posterior stabilization system.

Figure 30:
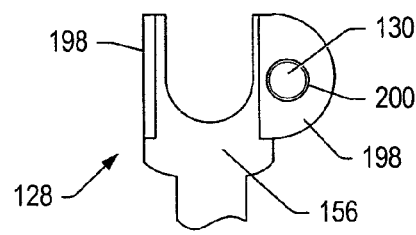
FIG. 30 depicts a front view representation of the second bone fastener depicted in FIG. 29.

FIG. 30 depicts a front view of a portion of second bone fastener 128 of FIG. 29 with member 198 coupled to collar 156 of the second bone fastener. Member 198 may include slot 200. A portion of elongated member 130 may pass through slot 200. Slot 200 and/or the portion of elongated member 130 that can pass through slot may have cross sectional shapes that accommodate rotation of second bone fastener 128 relative to the elongated member so that the dynamic posterior stabilization system is able to accommodate axial rotation of vertebrae being stabilized. Second bone fastener 128 may also be able to move axially along elongated member 130 so that the dynamic posterior stabilization system can accommodate flexion/extension and/or lateral bending of vertebrae being stabilized.

Figure 31:
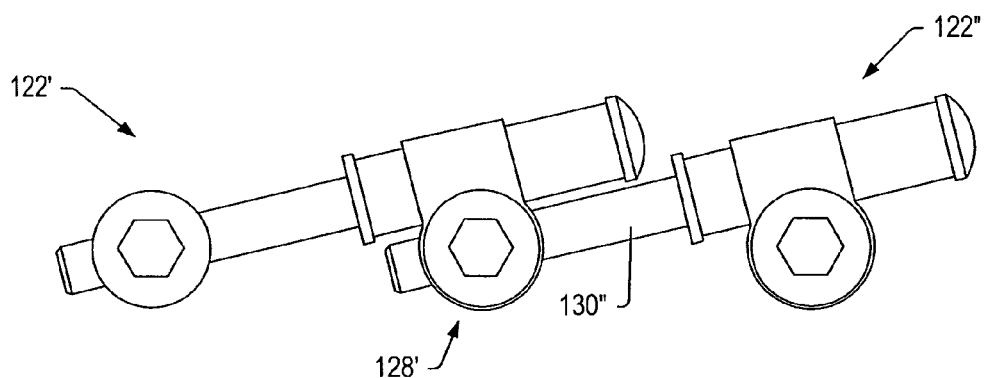
FIG. 31 depicts an embodiment of a multi-level dynamic posterior stabilization system.

Placement of the elongated member adjacent to the second bone fastener may allow for construction of a multi-level dynamic posterior stabilization system. FIG. 31 depicts a multi-level dynamic posterior stabilization system that includes dynamic posterior stabilization system 122' and dynamic posterior stabilization system 122". Elongated member 130" of dynamic posterior stabilization system 122" may be positioned in and secured to the collar of second bone fastener 128' of dynamic posterior stabilization system 122'. A mirror image dynamic posterior stabilization system construction may be installed on the contralateral side of the spine.

Figure 32:
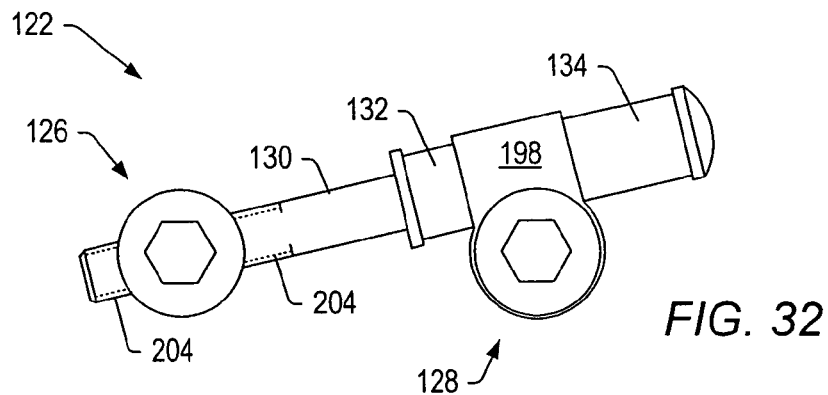
FIG. 32 depicts top view representation of an embodiment of a dynamic posterior stabilization system.

In some dynamic posterior stabilization system embodiments, the elongated member may be at a substantially fixed height relative to the second bone fastener. In some dynamic posterior stabilization system embodiments, the elongated member may angulate so that the height of the elongated member relative to the second bone fastener is variable. Allowing the height of the elongated member relative to the second bone fastener to vary may allow for the use of a straight elongated member with a dynamic interbody device. FIG. 32 depicts a top view representation of an embodiment of dynamic posterior stabilization system 122. Dynamic posterior stabilization system 122 may include first bone fastener 126, second bone fastener 128, elongated member 130, and bias members 132, 134. Elongated member 130 may include threaded portion 204. Second bone fastener 128 may include member 198. Member 198 may allow elongated member 130 to be positioned lateral to the fastener of second bone fastener 128. Lateral placement of the elongated member may allow for the establishment of multi-level stabilization systems. The elongated member of a second dynamic posterior stabilization system may couple to the collar of the second bone fastener of the first dynamic posterior stabilization system. In some embodiments, the member may position the elongated member through the collar of the second bone fastener.

Figure 33:
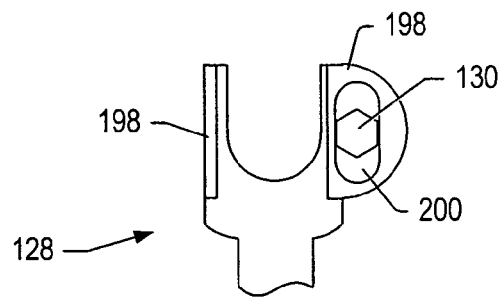
FIG. 33 depicts a front view representation of a portion of an embodiment of a second bone fastener of a dynamic posterior stabilization system.

FIG. 33 depicts a front view representation of a portion of second bone fastener 128. Member 198 may include slot. Slot 200 may allow for change in vertical position of elongated member 130 relative to second bone fastener 128. Change in vertical position of elongated member 130 relative to second bone fastener 128, along with the compression of one the bias members, may allow the dynamic posterior stabilization system to accommodate flexion or extension of vertebrae coupled to the dynamic posterior stabilization system.

The portion of elongated member 130 positioned in slot 200 may have one or more flats. For example, elongated member 130 may have a hexagonal portion. The flats may interact with member 198 to inhibit rotation of elongated member 130 relative to second bone fastener 128 while still allowing for changes in vertical position of the elongated member relative to the second bone fastener. Elongated member 130 may be able to rotate relative to the first bone fastener so that the dynamic posterior stabilization system is able to accommodate axial rotation of a first vertebra coupled to the first bone fastener relative to a second vertebra coupled to the second bone fastener.

Figure 34:
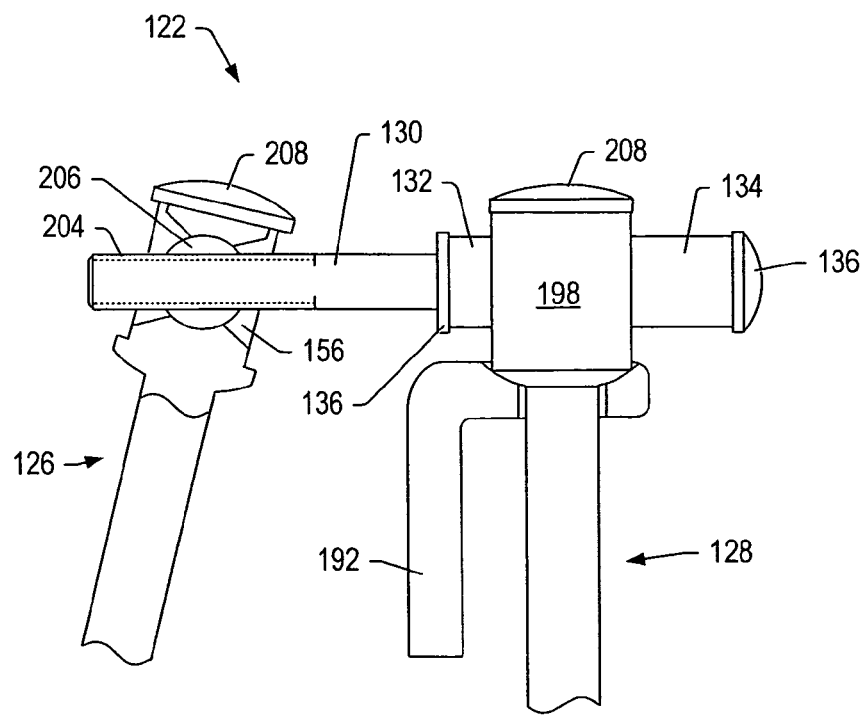
FIG. 34 depicts a side view representation of a portion of an embodiment of a dynamic posterior stabilization system with a bridge, wherein a portion of the first bone fastener is depicted in cutaway to emphasize the interior of the first bone fastener.

FIG. 34 depicts a side view representation of a portion of dynamic posterior stabilization system 122 with a portion of first bone fastener 126 depicted in cutaway to emphasize the interior of the first bone fastener. Ball 206 may be threaded on threaded portion 204 of elongated member 130. Ball 206 may be positioned in collar 156 of first bone fastener 126. Ball 206 may allow elongated member 130 to be pivotably coupled to first bone fastener 126. Closure member 208 for first bone fastener 126 may include a spherically shaped portion that complements a portion of the outer surface of ball 206. In some embodiments, the collar of the second bone fastener may accept a closure member that is identical to closure member 208 for first bone fastener 126 to avoid the need for different types of closure members for the first bone fastener and the second bone fastener.

In some embodiments, one or more lock rings may be placed on the threaded end of the elongated member. After the position of the ball is adjusted so that the elongated member will fit in the first bone fastener and the second bone fastener, one or more lock rings may be positioned against the ball to inhibit rotation of the ball relative to the elongated member. In some embodiments, an adhesive may be used to inhibit change in position of the ball relative to the elongated member after the position of the ball is set. Other systems may also be used to inhibit change in position of the ball relative to the elongated member after the position of the ball is set. In some embodiments, a portion of the end of the elongated member may be removed after the position of the ball is set so that there is little or no extension of the end of the elongated member beyond the collar of the first bone fastener when the dynamic posterior stabilization system is assembled.

In some embodiments, the ball may be at a fixed position on the elongated member. The length of the elongated member may be adjustable to allow the elongated member to be positioned in the first bone fastener and the second bone fastener. In an embodiment, a first portion of the elongated member may move relative to a second portion of the elongated member. A setscrew or other fastener may fix the position of the first portion relative to the second portion. Having a fixed position of the ball allows little or no extension of the end of the elongated member beyond the collar of the first bone fastener.

When closure member 208 is secured to collar 156 of first bone fastener 126, the closure member and the collar may allow rotation of ball 206 relative to the first bone fastener. Rotation of ball 206 allows for rotation and/or angulation of elongated member 130 relative to first bone fastener 126.

Closure member 208, collar 156 and ball 206 may allow for angulation of elongated member 130 relative to first bone fastener 126. The angular movement of elongated member 130, along with compression of bias member 132 or bias member 134, allows dynamic posterior stabilization system 122 to accommodate flexion/extension and/or lateral bending of the vertebrae coupled to the dynamic posterior stabilization system.

Elongated member assemblies may be provided in the instrument kit for the spinal stabilization procedure. The elongated member assemblies may include elongated member 130; ball 206 threaded on the elongated member; member 198; bias members 132, 134; and stops 136. During an installation procedure, the fastener of the first bone fastener 126 and the fastener of second bone fastener 128 may be positioned in the vertebrae to be stabilized. Bridge 192 may be positioned between the collar of second bone fastener 128 and the vertebra to which the second bone fastener is attached. Bridge 192 may be secured to the vertebra by the collar of the second bone fastener.

The position of ball 206 on elongated member 130 may be adjusted by rotating the ball relative to the elongated member until the position of the ball on the elongated member allows the ball to be positioned in collar 156 of first bone fastener 126 when member 198 is positioned in the collar of second bone fastener 128. Member 198 may be coupled to the collar of the second bone fastener and ball 206 may be positioned in collar 156 of first bone fastener 126. Closure member 208 may be used to secure member 198 to second bone fastener 128. Closure member 208 may be used to couple ball 206 to collar 156 of first bone fastener 126.

In some embodiments, a first dynamic posterior stabilization system coupled to vertebrae may be unconnected to a second dynamic posterior stabilization system on a contralateral side of the vertebrae. In some embodiments, one or more transverse connectors may connect dynamic posterior stabilization systems placed on contralateral sides of vertebrae.

Figure 35:
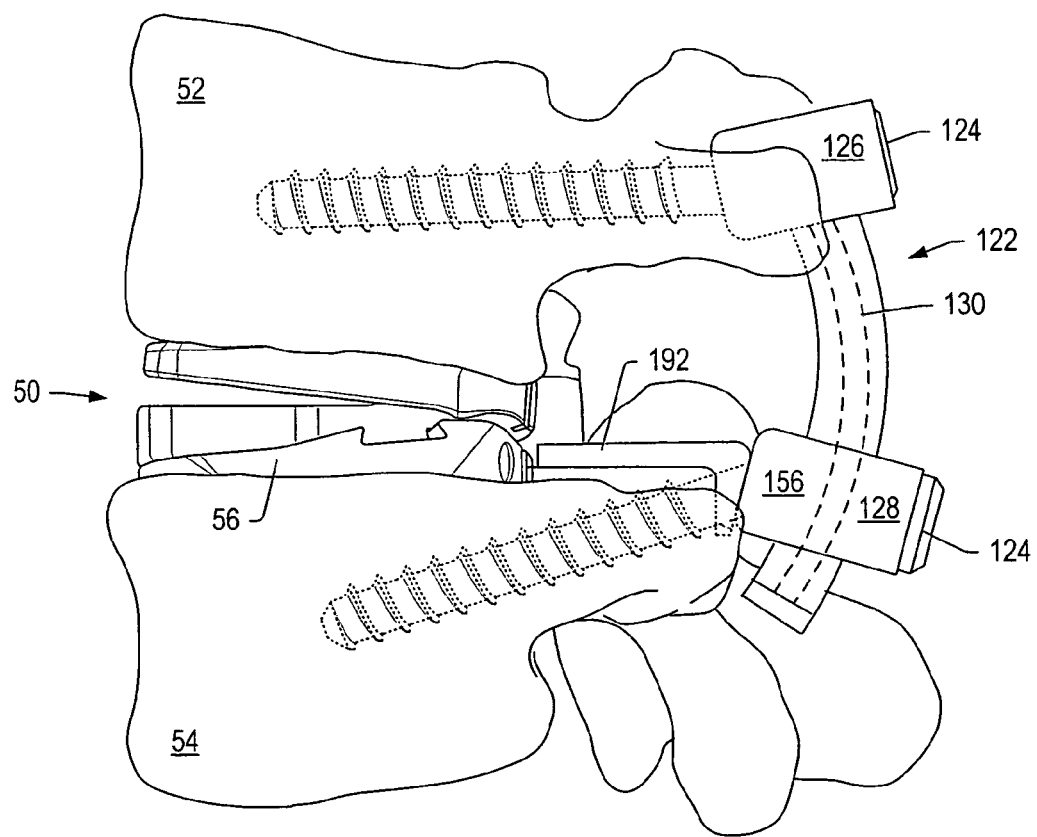
FIG. 35 depicts a representation of a dynamic interbody device and a posterior stabilization system coupled to vertebrae.

FIG. 35 depicts a representation of dynamic interbody device 50 and posterior stabilization system 122 positioned between vertebrae 52, 54. Bridge 192 may be coupled to second bone fastener 128 of dynamic posterior stabilization system 122. Coupling dynamic interbody device 50 to dynamic posterior stabilization system 122 may inhibit undesired migration of the dynamic interbody device relative to vertebrae 52, 54 while still allowing for flexion, extension, lateral bending, and/or axial rotation of the vertebrae.

When closure member 124 is tightened in collar 156 of second bone fastener 128, a bottom surface of the collar may align and be tightened against bridge 192. Tightening closure member 124 may fix the position of bridge 192. When closure member 124 is tightened so that the bottom of collar 156 is positioned against bridge 192, the center of curvature of elongated member 130 may align or substantially align with the center of curvature of dynamic interbody device 50 that allow for flexion/extension and/or lateral bending. Aligning or substantially aligning the center of curvature of elongated member 130 with the center or centers of curvature of dynamic interbody device 50 allows the elongated member to move relative to second bone fastener 128 during flexion/extension and/or lateral bending so that dynamic posterior stabilization system 122 works in conjunction with the dynamic interbody device.

Dynamic posterior stabilization system 122 may share a portion of the load applied to the vertebrae 52, 54 while providing guidance and resistance to flexion/extension and/or lateral bending that is, or is approximate to, the resistance provided by a normal functional spinal unit. Allowing for movement of the dynamic interbody device and for movement of the dynamic posterior stabilization system may inhibit deterioration of adjacent functional spinal units.

In some embodiments, first bone fastener 126 of dynamic posterior stabilization system is placed in the lower (more cephalad) of the vertebrae to be stabilized. Bridge 192 may couple dynamic interbody device 50 to dynamic posterior stabilization system 122. Bridge may be coupled to dynamic posterior stabilization system 122 at or near to second bone fastener 128. Coupling bridge 192 to dynamic posterior stabilization system 122 at or near to second bone fastener 128 may inhibit or eliminate contact of the bridge with neural structure exiting from between the vertebrae.

In some embodiments, a posterior approach may be used to install a stabilization system for a patient. The stabilization system may replace one or more parts of a functional spinal unit of the patient. The stabilization system may include one or more dynamic interbody devices, and one or more dynamic posterior stabilization systems.

Figure 36:
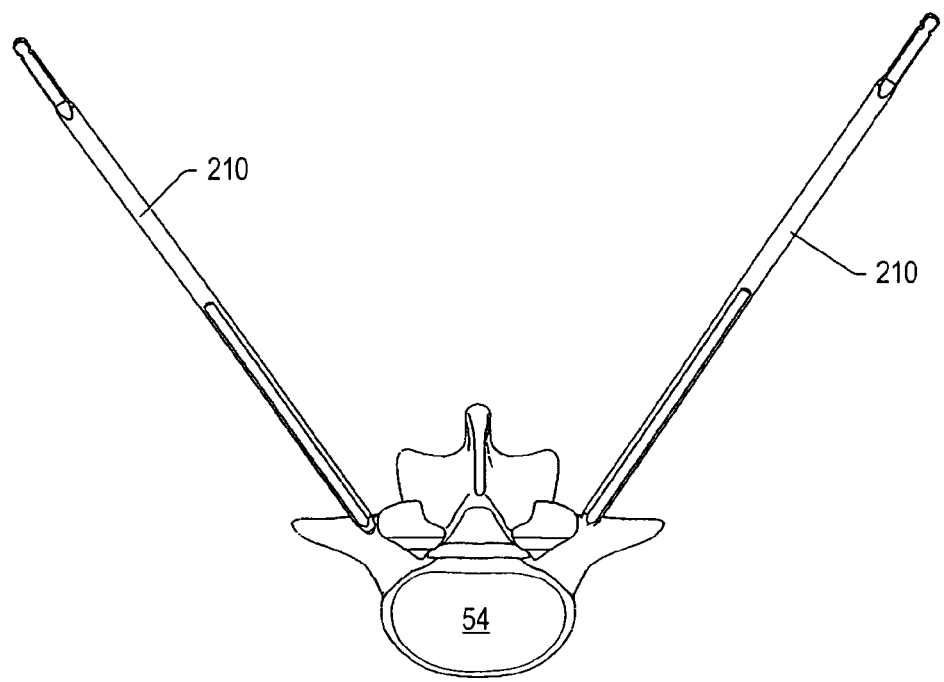
FIG. 36 depicts a representation of taps positioned in a lower vertebra during a spinal stabilization procedure.

During some posterior insertion procedures, the facet joints at the operative level may be removed (e.g., the superior facets from lower vertebra and the inferior facets from the upper vertebra). In some embodiments, the spinous process of the upper vertebra may also be removed. A bone awl may be used to mark each of the pedicles where the bone fasteners are to be positioned. A pedicle probe may be used to widen the initial holes made by the bone awl and set a desired trajectory. A tap may be attached to a handle and inserted into one of the pedicles. After insertion, the handle may be removed leaving the tap extending from the pedicle. The handle and the tap may have an AO connection or other type of low profile connection system. A tap may be inserted in each of the four pedicles. The taps may remain in the pedicles. Initially, the taps may be used to maintain distraction during a discectomy to provide disc space for the dynamic interbody devices. FIG. 36 depicts taps 210 positioned in lower vertebra 54, with the handle removed from the taps. Taps 210 may be positioned at any desired angle into lower vertebra 54 and the upper vertebra.

Figure 37:
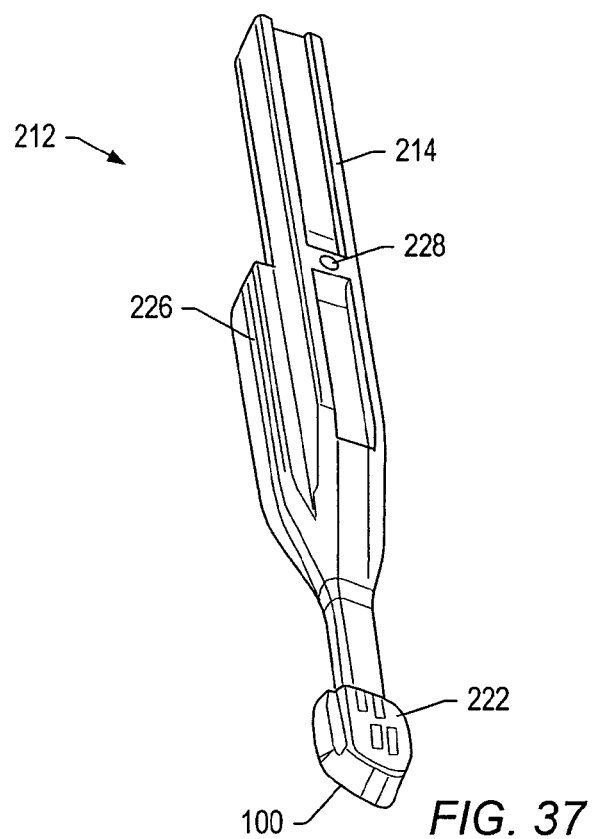
FIG. 37 depicts a perspective view of an embodiment of an expandable trial.
Figure 38:
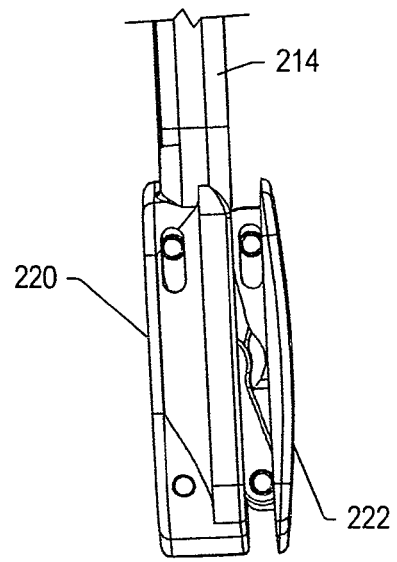
FIG. 38 depicts a perspective view of an end portion the expandable trial with the movable plate lifted from the base plate.
Figure 39:
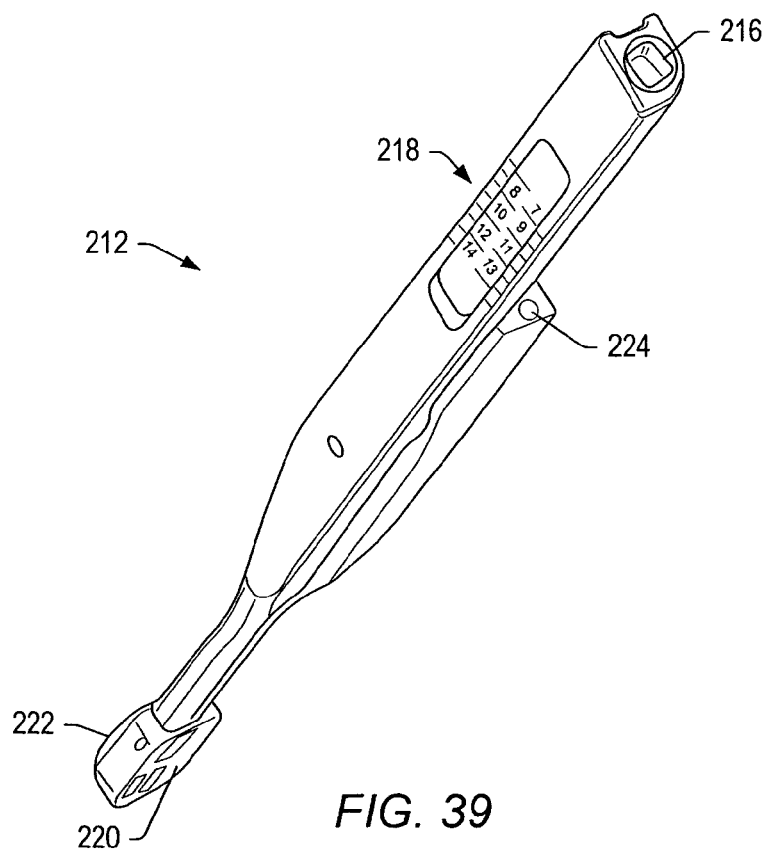
FIG. 39 depicts a perspective view of the expandable trial that emphasizes the top of the expandable trial.

After a discectomy, two expandable trials may be inserted in the disc space between the vertebrae. The expandable trial used on the left side of the patient may be a mirror image of the expandable trial used on the right side of the patient. FIGS. 37-39 depict an embodiment of expandable trial 212 that may be positioned on a first side of the vertebrae. Each expandable trial may include body 214, rotator 216, scale 218, base plate 220 and movable plate 222. Rotator 216 may be located at an end of body 214. Scale 218 may be located in an upper portion of body 214.

A rotatable handle may be coupled to rotator 216. When rotator 216 is turned, movable plate 222 moves in or out relative to base plate 220. FIG. 38 depicts movable plate 222 extended away from base plate 220. The amount of movement of movable plate 222 relative to base plate 220 may be indicated by the change in position of a movable portion of scale 218 relative to a stationary portion of the scale. The movable portion may include numbers and markings that indicate the height of a corresponding dynamic interbody device. The marking and corresponding number that aligns with a marking of the stationary portion of the scale indicates the current separation height of movable plate 222 relative to base plate 220.

A middle portion of body 214 may include passage 224, keyway 226, and guide recess 228. A drill or other type of cutter may be positioned through passage 224 to form a groove in the lower vertebra to accommodate a keel of the dynamic interbody device to be positioned in the disc space between the vertebrae. Keyway 226 may ensure that only the proper instrument guide can be used in association with the particular expandable trial. Guide recess 228 may accept an end of a guide release of the proper guide.

Base plate 220 may have an inferior surface with a shape that is substantially the same as the shape of the inferior surface of the dynamic interbody device to be positioned between the vertebrae. Base plate 220 may be positioned against the lower vertebra of the vertebrae being stabilized. Movable plate 222 may have a superior surface with a shape that is substantially the same as the shape of the superior surface of the dynamic interbody device to be positioned between the vertebrae. When the expandable trial is in an initial position, the movable plate and the base plate have a height that allows for insertion in the disc space between the vertebrae. After insertion, the rotator may be turned to separate the movable plate from the base plate to position the base plate against the lower vertebra and the movable plate against the upper vertebra.

The base plate and movable plate of the expandable trials may be positioned in the disc space between the vertebrae. An engaging end of a handle may be inserted in the rotator of a first expandable trial. The handle may be turned to cause the movable plate to move away from the base plate so that the movable plate and the base plate contact the vertebrae. The handle may be used to rotate the rotator of the second expandable trial so that the movable plate and the base plate of the second expandable trial contact the vertebrae. The separation height between the base plate and the movable plate is indicated by the scale of the expandable trial.

Figure 40:
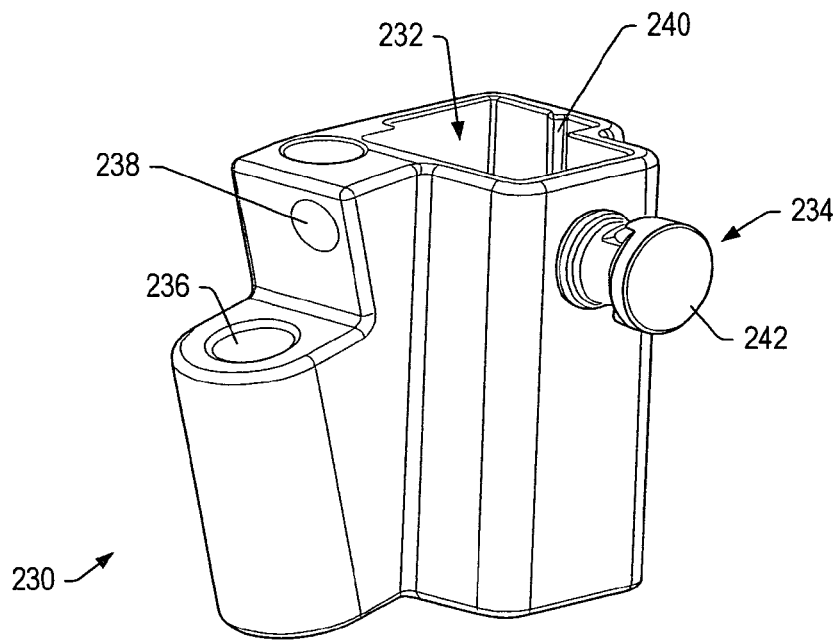
FIG. 40 depicts a perspective view of an embodiment of a guide.
Figure 41:
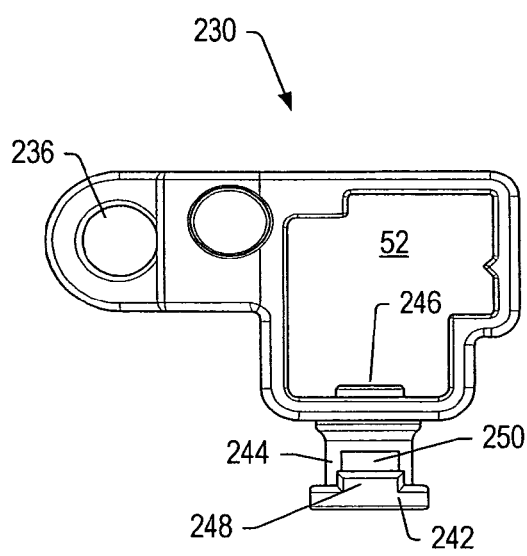
FIG. 41 depicts a top view of the guide with the guide release in a first position.
Figure 42:
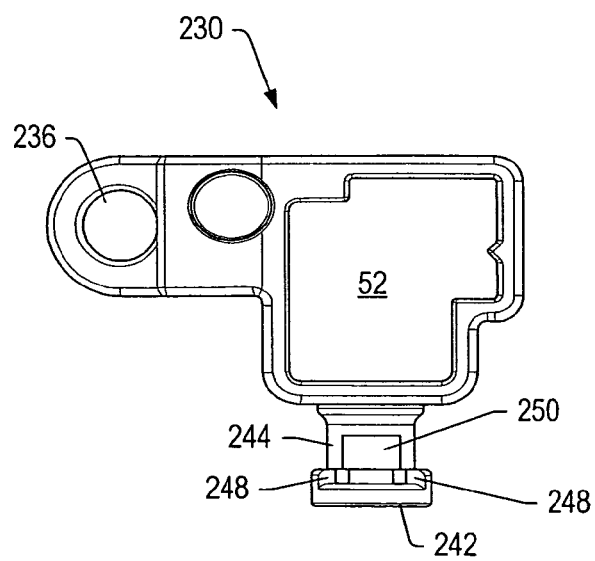
FIG. 42 depicts a top view of the guide with the guide release in a second position.

Guides may be coupled to each expandable trial. FIGS. 40-42 depict an embodiment of guide 230. Guide 230 may include passageway 232, guide release 234, passage 236, and recess 238. Passageway 232 may include key 240. Passageway 232 is shaped to fit over the body of the proper expandable trial. The key of the proper expandable trial fits in keyway 240. Passage 236 accepts posts of a bridge that couples the first expandable trial to the second expandable trial. Recess 238 accommodates a stabilizer of the bridge.

Guide release 234 may include grip 242, body 244, and end 246. When grip 242 is pulled outward from the guide 230, the grip may be rotated relative to body 244. In a first position (depicted in FIG. 41), end 246 of guide release extends into passageway 232. Arms 248 of grip 242 are next to flats 250 of body 244. A spring or other bias member in guide release 234 drives end 246 into passageway 232. In a second position (depicted in FIG. 42), end 246 does not extend into passageway 232. Grip 242 is pulled away from passageway 232 and rotated so that arms 248 of the grip reside on the top of body 244. The second position may be used to facilitate removal of an expandable trial or insertion instrument from guide 230.

A first guide may be placed over the appropriate expandable trial and lowered until the key of the guide is in the keyway of the expandable trial and the end of the guide release inhibits further movement of the guide. The grip may be pulled outwards to withdraw the end of the guide release from the passageway. The guide may be lowered and the grip may be released so that the spring in the guide release forces the end of the guide release against the body of the expandable trial. The guide may be lowered until the end of the guide release extends into the guide recess of the expandable trial. A second guide may be placed over the other expandable trial. Attaching the guides to the expandable trials after insertion of the base plates and movable plates between the vertebrae may allow more visibility of the position of the base plates and movable plates of the expandable trials during insertion. During some dynamic interbody device insertion procedures, the guide for the first expandable trial and/or the guide for the second expandable trial is placed on the appropriate expandable trial before the base plate and movable plate of the expandable trial is positioned between the vertebrae.

The position of the expandable trials may be adjusted so that the passages of the guides are oriented vertically. Also, an end of the base plate of the first expandable trial may touch or be close to touching an end of the base plate of the second expandable trial. In some embodiments, the base plates of the expandable trials may be coupled together with male and female portions when the base plates are positioned between the vertebrae.

Figure 43:
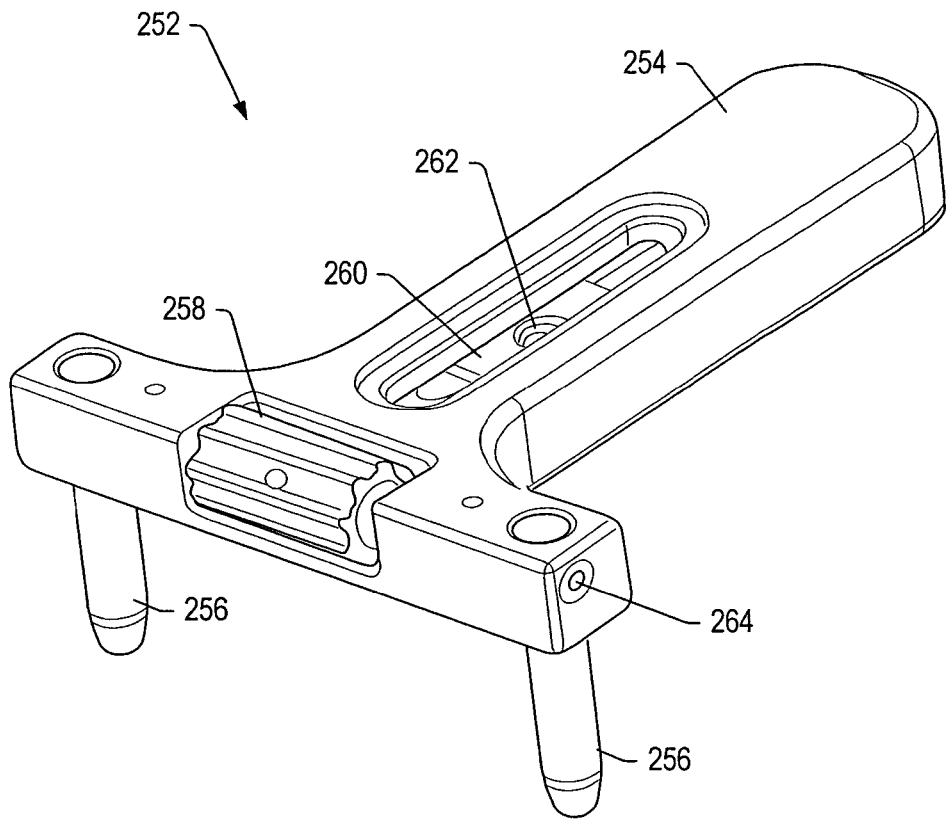
FIG. 43 depicts a perspective view of an embodiment of an insertion bridge.
Figure 44:
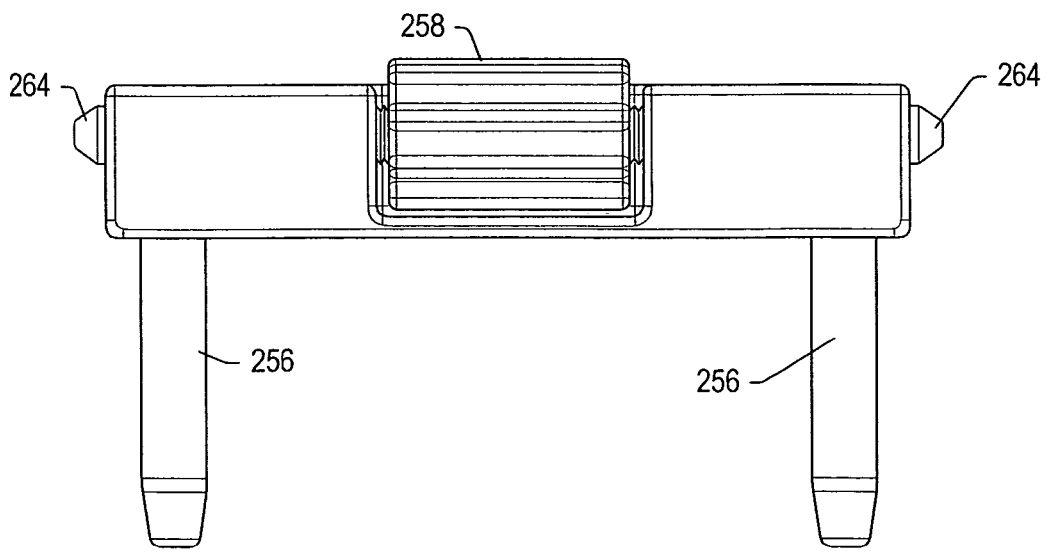
FIG. 44 depicts a front view of the insertion bridge.

Posts of the bridge may be inserted in the passages of the guides. FIG. 43 depicts an embodiment of insertion bridge 252. Insertion bridge 252 may include handle 254, posts 256, and wheel 258. Handle 254 facilitates positioning and moving insertion bridge 252. Handle 254 may include slide 260 with threaded opening 262. Slide 260 may move forward and backward in handle 254. Posts 256 may fit within passages of the guides. Wheel 258 may extend or retract stabilizers 264. Stabilizers 264 may extend from the body of insertion bridge 252 into the recesses of the guides. FIG. 44 depicts stabilizers 264 extended from the body of insertion bridge 252. When the stabilizers 264 are extended against the recesses of the guides, the outward force applied by the stabilizers to the guides generates torque applied by the guide to posts 256. The outward force and the torque couple the guides to insertion bridge 252 so that the guides remain coupled to the bridge when the expandable trials are removed from the guides.

Figure 45:
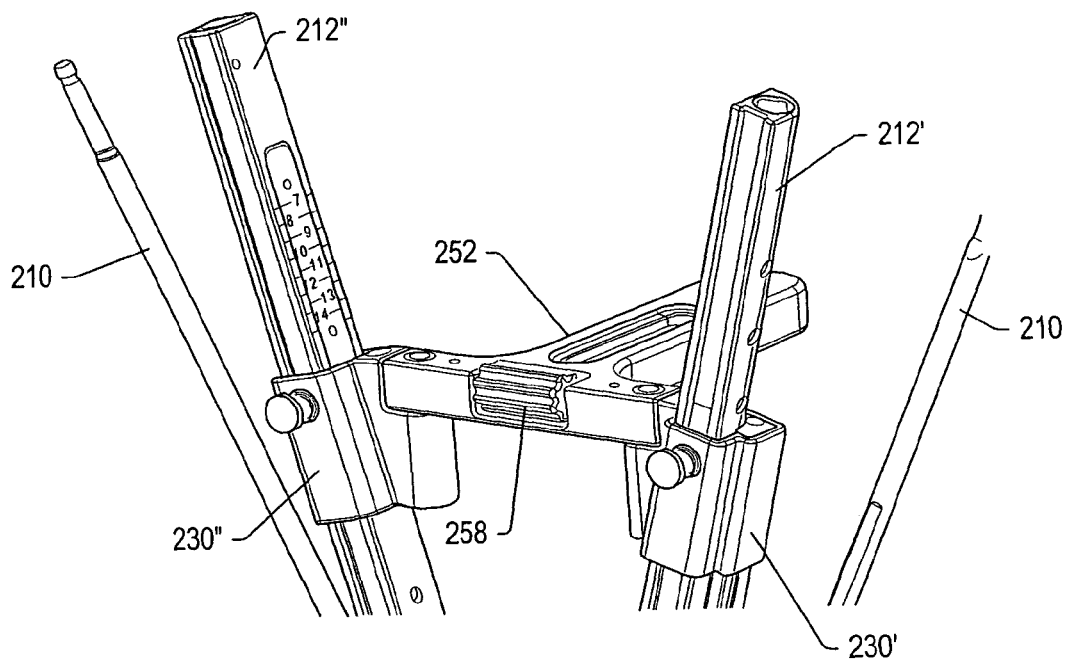
FIG. 45 depicts a perspective view of the bridge coupled to guides and expandable trials.

FIG. 45 depicts insertion bridge 252 coupled to guides 230', 230". Wheel 258 has been turned to extend the stabilizers into the recesses of the guides and couple guides 230', 230" to insertion bridge 252.

Figure 46:
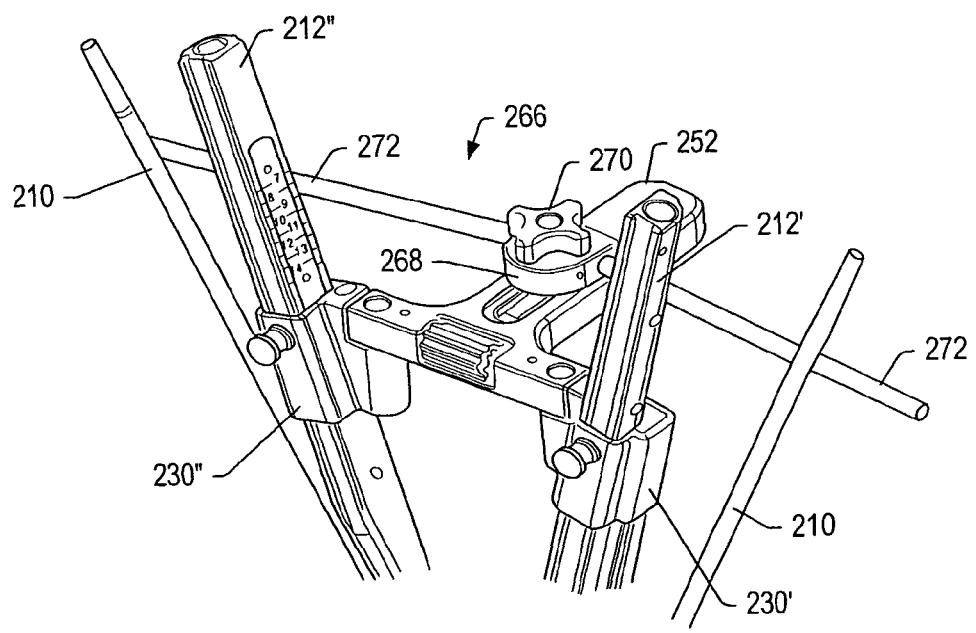
FIG. 46 depicts a perspective view of a bar assembly coupled to the bridge, guides, and expandable trials.

A bar assembly may be coupled to the slide of the insertion bridge. FIG. 46 depicts bar assembly 266 coupled to insertion bridge 252. Bar assembly 266 may include base 268, knob 270, and rods 272. A shaft of coupled to knob 270 may extend through base 268. A threaded end of the shaft may be threaded into the threaded opening in the slide of insertion bridge 252. Rods 272 may be coupled to the base 268. Rods 272 may be positioned near taps 210 by sliding the slide relative to handle 254 and/or by rotating rods 272 relative to the taps. When rods 272 are positioned near taps 210, knob 270 may be tightened against base 268 to inhibit movement of the slide relative to handle 254 and to inhibit rotation of the rods relative to the taps.

Figure 47:
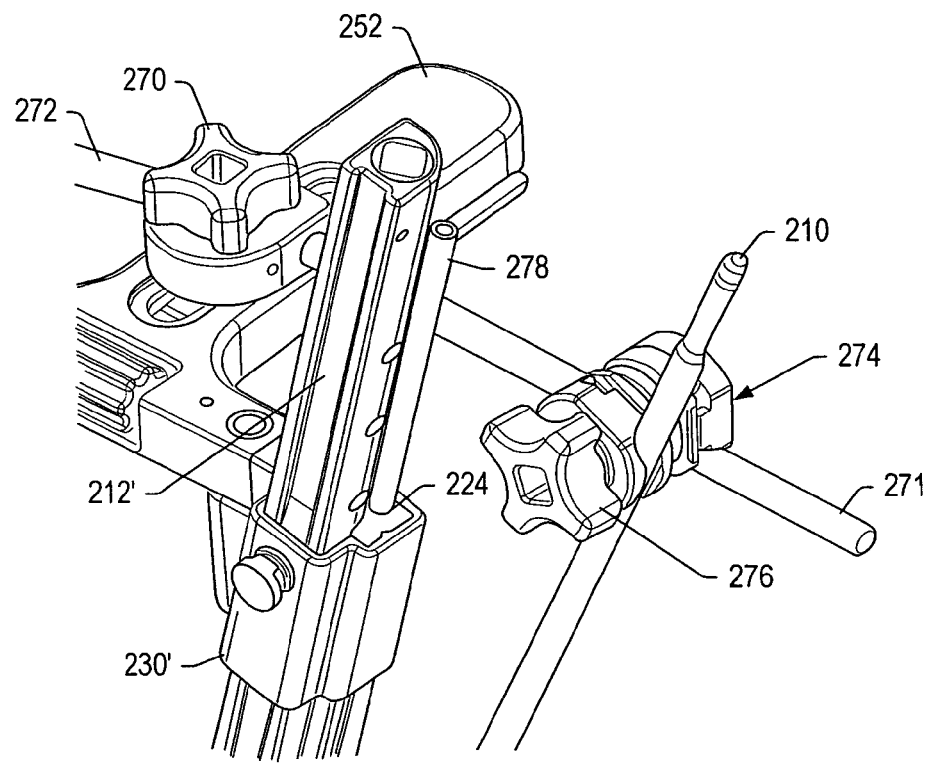
FIG. 47 depicts a perspective view of a rod connector attached to the tap and the rod of the bar assembly.

Rod connectors may be attached to the taps and to the rods of the bar assembly to anchor the insertion bridge to the spine. FIG. 47 depicts rod connector 274 attached to tap 210 and rod 272. When tap 210 and rod 272 are snapped into the openings of rod connector 274, knob 276 of the rod connector may be tightened to secure the taps and rods together. A second rod connector may be used to secure the second tap to the second rod.

Figure 48:
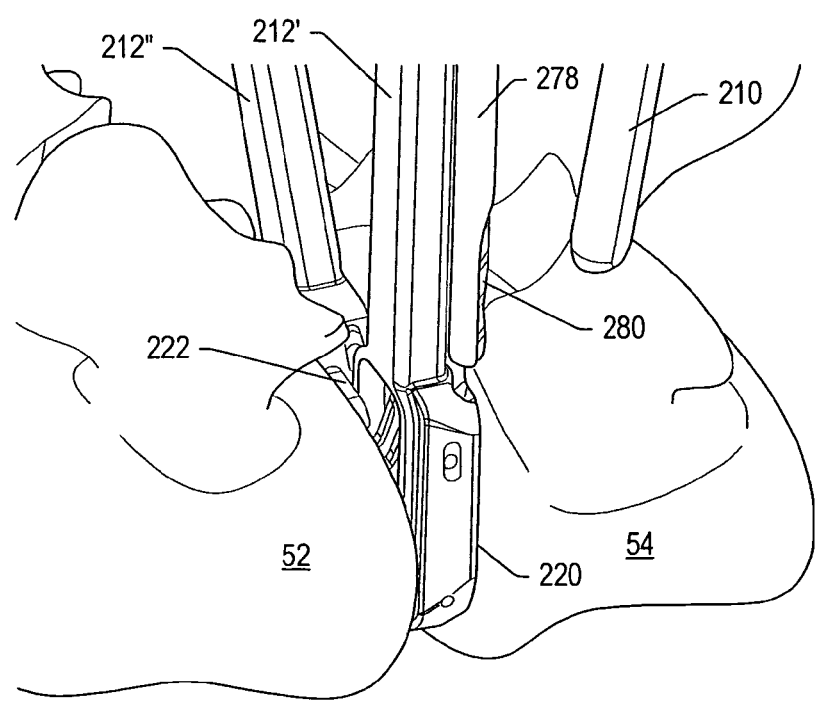
FIG. 48 depicts a perspective view of a keel guide and drill during formation of a keel opening in a vertebra.

The rotatable handle may be inserted into the rotators of the expandable trials and turned to set the expandable trials to the height of the dynamic interbody devices to be placed in the disc space. A keel guide may be inserted in the passage of the first expandable trial. FIG. 47 also depicts keel guide 278 positioned in passage 224 of expandable trial 212'. FIG. 48 depicts a distal portion of keel guide 278 with drill bit 280 forming a groove in lower vertebra 54. Base plate 220 of expandable trial includes a concave groove that accommodates drill bit 280. After the formation of the first keel groove, drill bit 280 and keel guide may be removed from the first expandable trial. The keel guide may be placed in the passage of the second expandable trial. The drill bit may be used to form a second keel groove in the lower vertebra.

Figure 49:
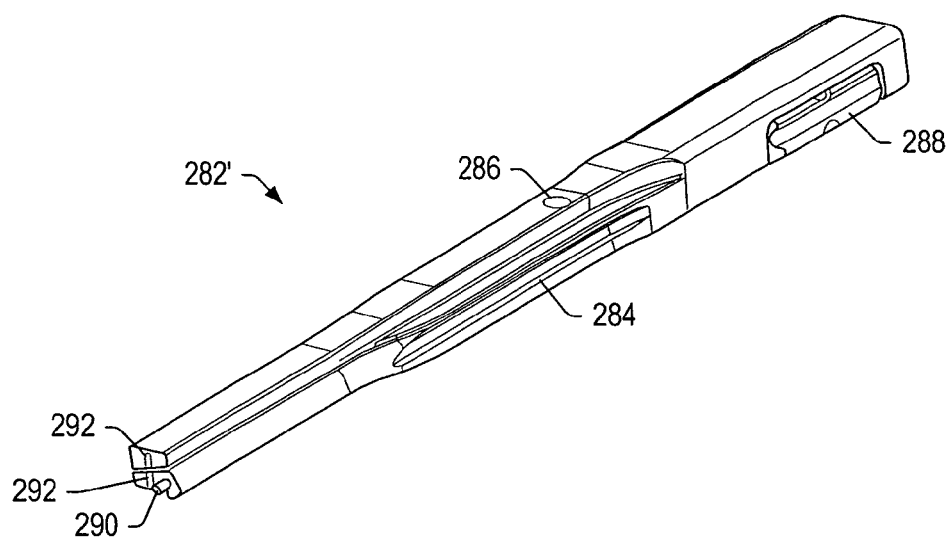
FIG. 49 depicts a perspective view of an embodiment of an insertion instrument.

The dynamic interbody devices to be inserted between the vertebrae may be attached to the appropriate insertion instruments. FIG. 49 depicts insertion instrument 282' for the first dynamic interbody device. The insertion instrument for the second dynamic interbody device may be a mirror image of the insertion instrument for the first dynamic interbody device. Insertion instrument 282 may include key 284, guide recess 286, wheel 288, shaft 290, and ridges 292. Key 284 and the shape of the body of insertion instrument 282 correspond to the shape of the passageway through the appropriate guide. Guide recess 286 accepts the end of the guide release of the guide to fix the position of insertion instrument 282 relative to the guide.

Wheel 288 may be rotated to rotate shaft 290. Rotating shaft 290 may advance or retract the shaft relative to the body of insertion instrument 282. The end of shaft 290 may be threaded. The threaded end may mate with the threaded opening in the appropriate dynamic interbody device. When shaft 290 is threaded to the appropriate dynamic interbody device, ridges 292 reside in the slots of the dynamic interbody device to place the dynamic interbody device in the desired position for insertion (i.e., neutral axial rotation, neutral lateral bending, and full flexion).

The rotation handle may be attached to the rotator of the first expandable trial. The rotator may be turned to decrease the separation height between the base plate and the movable plate of the expandable trial. The grip of the guide release may be pulled outwards, rotated and released so that the end of the guide release is withdrawn from the passageway of the guide. The first expandable trial may be removed from the guide. The first dynamic interbody device may be placed through the passageway and between the vertebrae. The grip of the guide release may be pulled outwards, rotated and released so that the spring of the guide release tries to force the end of the guide release into the passageway of the guide. The insertion instrument may be driven downwards until the end of the guide release snaps into the guide recess of the insertion instrument. If needed, a mallet or other impact instrument may be used against the insertion instrument to drive the dynamic interbody device between the vertebrae.

Figure 50:
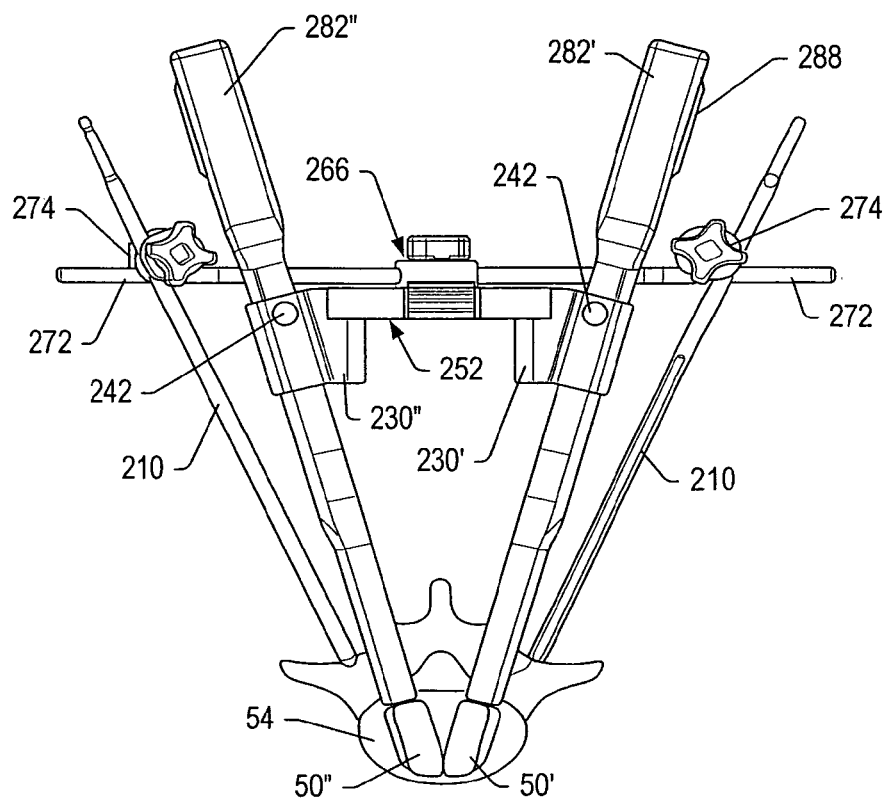
FIG. 50 depicts a perspective view of the lower vertebra with insertion instruments placing the dynamic interbody devices at a desired position.

The second expandable trial may be removed from the guide. The second dynamic interbody device may be inserted between the vertebrae. FIG. 50 depicts instrument inserters 282 and dynamic interbody devices 50', 50" positioned against lower vertebrae 54. Imaging techniques may be used to determine that the dynamic interbody devices are properly interconnected and positioned in the disc space. When the dynamic interbody devices are properly interconnected and positioned, wheels 288 of insertion instruments 282', 282" may be rotated to disconnect the insertion instruments from dynamic interbody devices 50', 50". Grips 242 of guides 230 may be pulled outwards to retract the ends of the guide releases from the passageways of the guides, and insertion instruments 282', 282" may be removed from the guides. Rod connectors 274 may be removed from taps 210 and bars 272. Insertion bridge 252, with bar assembly 266 and guides 230, may be removed.

Taps 210 may be removed from the vertebrae and bone fasteners of dynamic posterior stabilization systems may be inserted in the openings where the taps where positioned. Elongated members may be coupled to the bone fasteners to form dynamic posterior stabilization systems on each side of the vertebrae.

In some embodiments, another technique may be used to insert dynamic interbody devices between vertebrae. An insertion structure may be formed before positioning an expandable trial or expandable trials between the vertebrae. Taps may be inserted in each of the pedicles. FIG. 36 depicts taps 210 positioned in lower vertebra 54, with the handle removed from the taps. Taps 210 may be positioned at any desired angle into lower vertebra 54 and the upper vertebra.

After a discectomy, one or more trials may be positioned in and removed from the disc space on a first side and a second side of the vertebrae. The trials may have the same length and width profile as the first member of the dynamic interbody device to be placed in the disc space or the same length and width profile as the third member of the dynamic interbody device to be placed in the disc space. The lengths and widths of the dynamic interbody devices to be placed in the disc space may be determined based on the trials.

Figure 51:
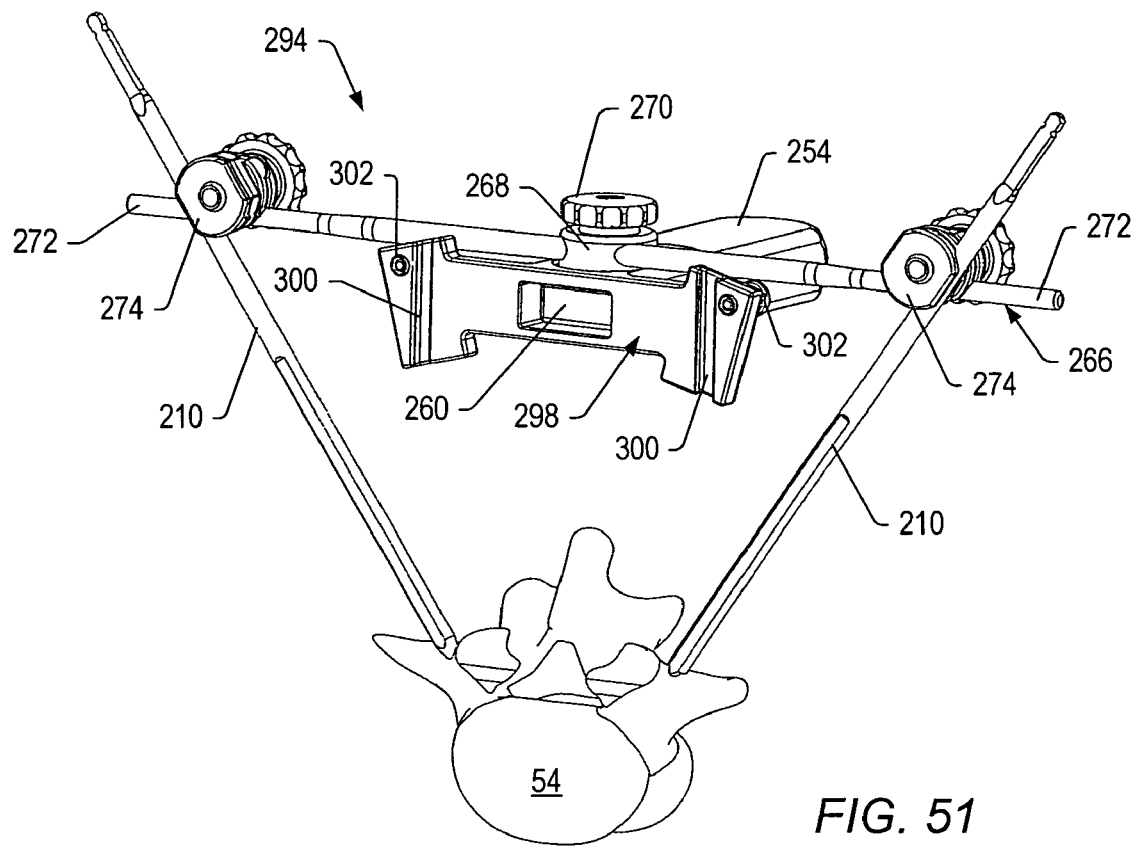
FIG. 51 depicts a perspective representation of an embodiment of a support frame coupled to taps positioned in the lower vertebra.

During some insertion procedures, the position of lower vertebra 54 is used as the basis for establishing the insertion angles for the dynamic interbody devices. A support frame may be coupled to taps 210. FIG. 51 depicts support frame 294 coupled to taps 210. Support frame 294 may include rod connectors 274, bar assembly 266, and bridge assembly 298. Bar assembly 266 may include a shaft with a threaded end, hub 268, knob 270, and rods 272. Rods 272 may be directly connected to hub 268 so that rotation of the rods independent of the hub is inhibited.

Rod connectors 274 may be used to couple bar assembly 266 to taps 210. Tap connectors 274 have sufficient freedom of movement to allow bar assembly 266 to be positioned at a desired height above the vertebrae with a horizontal orientation and with the vertical center line of the bridge assembly positioned substantially in line with the vertical center line of the end plate of lower vertebra 54. Hub 268 may be rotated in a recess in the handle of bridge assembly 298 to allow the front face of the bridge assembly to be oriented substantially parallel to the end plate of lower vertebra 54. Hub 268 may be moved forward or backward in the recess to adjust the offset distance of the front face of bridge assembly 298 from the end plate of lower vertebra 54.

Bridge assembly 298 may include handle 254, slide 260, guide slots 300, and guide releases 302. Handle 254 may be used to move bridge assembly 298. Slide 260 may be positioned in a hollow portion of handle 254. Hub 268 of bar assembly 266 may be positioned in a recess in handle 254. The threaded end of the shaft of bar assembly 266 may be threaded into a threaded opening of slide 260. When knob 270 of bar assembly 266 is loose, the bar assembly may be adjusted back and forth in the recess of handle to change the offset position of the front face of bridge assembly 298 relative to lower vertebra 54. Also, the orientation of the front face of bridge assembly 298 relative to the end plate of the lower vertebra may be changed by rotating handle 254 relative to hub 268. Knob 270 may be tightened to fix the position of bar assembly 266 relative to the handle 254. When bridge assembly 298 is properly positioned, the front face of the bridge assembly may be substantially parallel to the endplate of bottom vertebra 54, and guide slots 300 are substantially vertical and equidistant from the vertical centerline of lower vertebra 54.

Protrusions of instrument guides may be positioned in guide slots 300. Guide releases 302 may include a spring or other bias member that extends an end of the guide release beyond the front face of the bridge assembly. The end of the guide release may extend into an opening of an instrument guide to couple bridge assembly 298 to the instrument guide. A grip may be pulled away from bridge assembly 298 to retract the end of guide release 300 and allow the instrument guide to be removed from the bridge assembly.

A first guide and a second guide may be placed in guide slots 300 of bridge assembly 298. The first guide may be a mirror image of the second guide. When the guides are fully inserted in the guide slots of bridge assembly 298, guide releases 302 inhibit movement of the guides. During some procedures, guides are positioned in guide slots 278 before the support frame is coupled to the taps.

Figure 52:
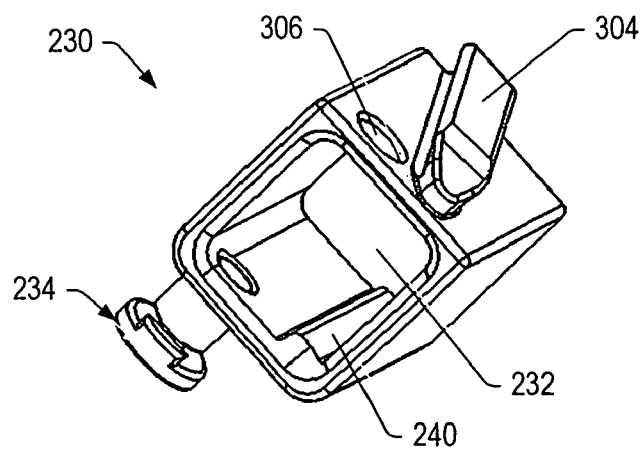
FIG. 52 depicts a perspective view of an embodiment of a first guide for a bridge assembly.

FIG. 52 depicts a perspective view of first instrument guide 230' used on a first side of the bridge assembly. First instrument guide 230' may include protrusion 304, opening 306, passageway 232, key 240, and guide release 234. Protrusion 304 may be placed in a guide slot guide slot of the bridge assembly. Protrusion 304 may be angled relative to passageway 232 so that the passageway is at a desired angle relative to vertical (and the lower vertebra) when the protrusion is positioned in the guide slot of the bridge assembly. In some embodiments, the angle of passageway 232 of the first guide 230' and the angle of the passageway of the second guide are directed inwards toward the vertical center line of the lower vertebra at about 15° relative to vertical. When protrusion 304 is inserted in the guide slot of the bridge assembly, the end of the bridge assembly guide release extends into opening 306 to inhibit undesired movement of first guide 230'.

A trial or inserter may be placed through passageway 232 of first guide 230' that is positioned in the bridge assembly. Passageway 232 may include key 240. Key 240 may fit in a keyway of an appropriate trial or inserter used with the first guide 230'. When the appropriate trial or inserter is positioned in first guide 230', a spring or other bias member of guide release 234 may extend an end of the trial release into an opening in the trial or inserter to inhibit movement and allow a user to know that the trial or inserter is fully inserted.

Figure 53:
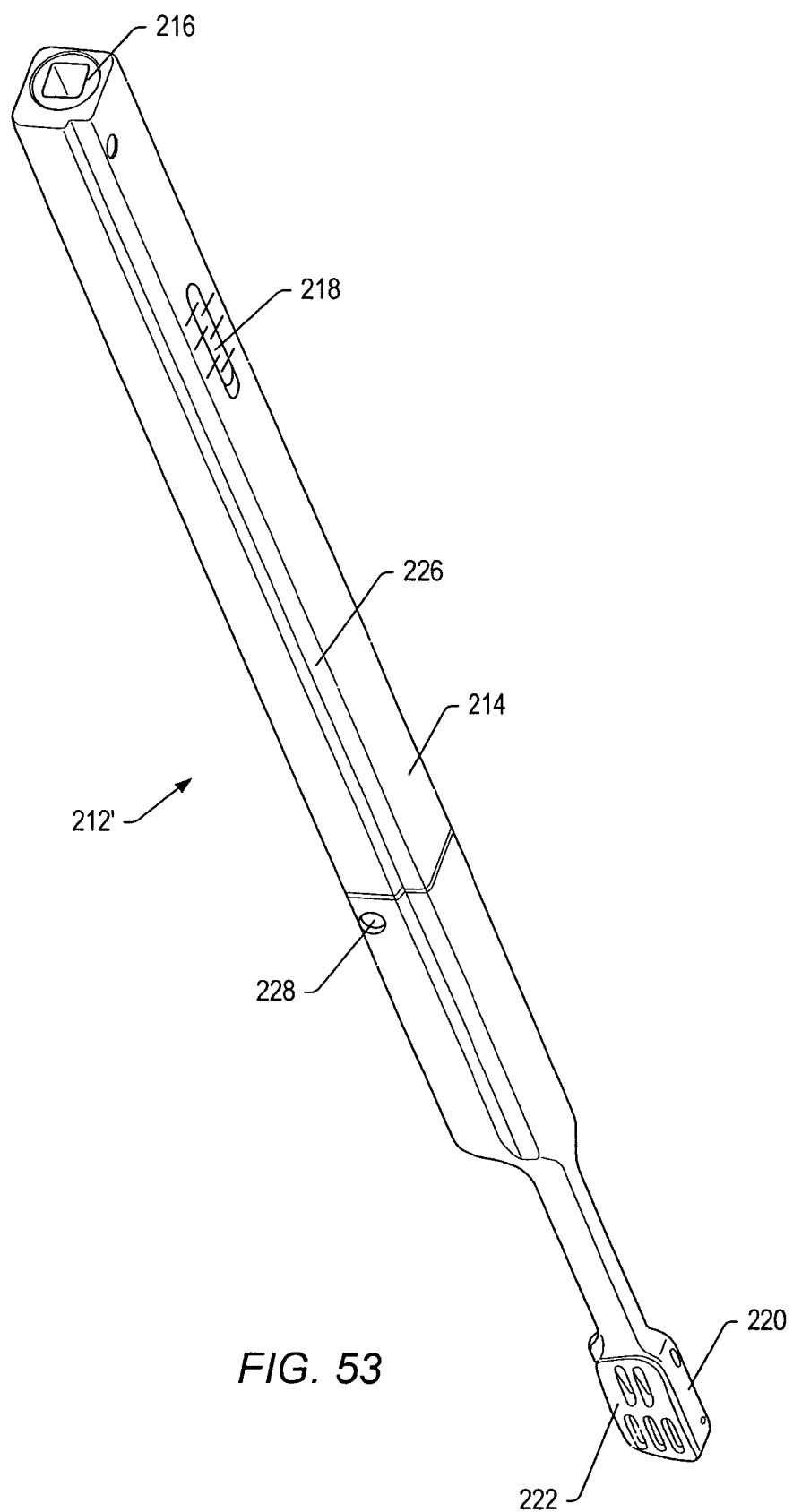
FIG. 53 depicts a perspective view of an embodiment of an expandable trial.

FIG. 53 depicts an embodiment of first expandable trial 212' that may be used to determine the appropriate height of a dynamic interbody device to be positioned between vertebrae. First expandable trial 212' may be used in conjunction with the first guide. A second expandable trial, which may be a mirror image of first expandable trial 212', may be used in conjunction with the second instrument guide. Expandable trial 212' may include body 214, keyway 226, guide recess 228, rotator 216, scale 218, base plate 220 and movable plate 222. Keyway 226 may extend along a portion of body 214. When expandable trial 212' is inserted into the first guide, the key of the guide is positioned in keyway 226. Keyway 226 only allows the use of expandable trial 212' with the appropriate guide. When expandable trial 212' is fully inserted in the first guide, an end of the guide release of the guide may extend into guide opening 228 to inhibit further insertion of the expandable trial.

Rotator 216 may be located near a first end of expandable trial 212'. A tool may be positioned in rotator 216. Turning the tool may advance a shaft in the upper part of body 214. Torque needed to turn the tool and advance the shaft may be offset by counter-torque applied to the handle of the bridge assembly. The amount of advancement of the shaft may be indicated on scale 218. Scale 218 may indicate height corresponding to height between the upper portion of movable plate 222 and the lower portion of base plate 220.

Turning rotator 216 extends the shaft against an actuator located in the lower part of body 214. The actuator may engage a linkage mechanism coupled to base plate 220 and movable plate 222. The actuator may push and move a linkage pin. The linkage pin is coupled to lifting arms. When the linkage pin is moved, the linkage arms raise movable plate 222 from base plate 220. FIG. 38 depicts an end portion of expandable trial with movable plate 222 lifted above base plate 220.

Before insertion through passages of the guides, the movable plates of the expandable trials may be adjusted relative to the base plates so that the movable plates and base plates can be inserted into the disc space between the vertebrae. The expandable trials may be inserted in the appropriate insertion guides so that the movable plates and base plates of the expandable trials extend into the disc space between the vertebrae. The base plates may be abutted against the end plate of the lower vertebra by loosening the knob of the bridge assembly and moving the base plates against the lower vertebra. The knob may be tightened to inhibit additional movement of the expandable trials relative to the lower vertebrae.

Figure 54:
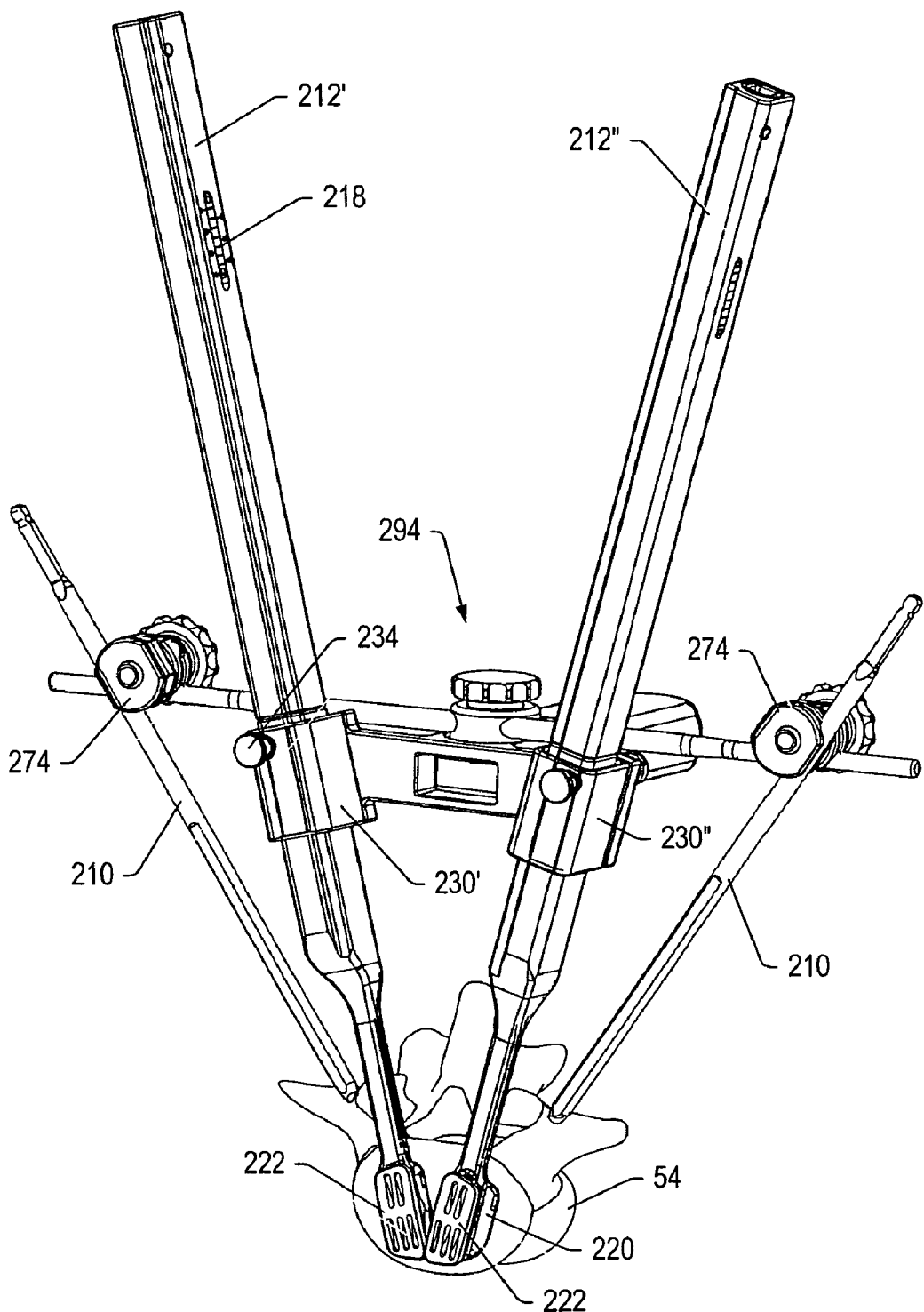
FIG. 54 depicts a representation of expandable trials positioned against the lower vertebra during the dynamic interbody device insertion procedure.

FIG. 54 depicts expandable trials 212', 212" positioned in guides 230', 230". The rotators of expandable trials 212', 212" may be turned in a first direction to lift movable plates 222 above the base plates 220. The tool used to turn the rotators may include a torque gauge. The rotators may be turned until a desired amount of torque is applied. When the desired amount of torque is applied, the height indicated on scales 218 of expandable trials may correspond to the heights of dynamic interbody devices to be implanted between the vertebrae.

The appropriate dynamic interbody devices may be selected from the insertion kit. Each dynamic interbody device may be coupled to an appropriate inserter. The rotator of first expandable trial 212' may be turned in the direction opposite to the direction that lifts movable plate 222 from base plate 220. The grip of guide release 234 of first guide 230' may be pulled and expandable trial 212' may be removed from the first guide. The vertebrae may be prepared to receive the first dynamic interbody device. For example, a channel may be formed in a vertebra to accept a keel of the dynamic interbody device. The first dynamic interbody device may be inserted through first guide 230' and into the disc space. The same procedure may be followed to insert the second dynamic interbody device into the disc space.

The portions of the inserters that fit in the inserter openings of the dynamic interbody devices may be retracted from the inserter openings. The portions of the inserter that reside in the curved slots of the second members and third members of the dynamic interbody devices may be rotated to remove the portions from the curved slots. The inserters may be removed from the guides 230', 230". Tap connectors 274 may be released and removed from taps 210. Support frame 294 and instrument guides 230', 230" may be removed from the patient.

Taps 210 may be removed from the vertebrae and bone fasteners of dynamic posterior stabilization systems may be inserted in the openings where the taps where positioned. Elongated members may be coupled to the bone fasteners to form dynamic posterior stabilization systems on each side of the vertebrae.

In this patent, certain U.S. patents, and U.S. patent applications have been incorporated by reference. The text of such U.S. patents and U.S. patent applications is, however, only incorporated by reference to the extent that no conflict exists between such text and the other statements and drawings set forth herein. In the event of such conflict, then any such conflicting text in such incorporated by reference U.S. patents and U.S. patent applications is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of inserting a first dynamic interbody device and a second dynamic interbody device in a disc space between a first vertebra and a second vertebra, comprising:
    placing taps into the first vertebra;
    attaching a bridge assembly to the taps and positioning a face of the bridge assembly at a desired position relative to the first vertebra;
    attaching a first guide and a second guide to the bridge assembly;
    placing an end of a first expandable trial through the first guide and in the disc space between the first vertebra and the second vertebra;
    placing an end of a second expandable trial through the second guide and in the disc space between the first vertebra and the second vertebra;
    adjusting the separation distance between a movable plate and a base plate of the first expandable trial and adjusting the separation distance between a movable plate and a base plate of the second expandable trial;
    attaching the first dynamic interbody device to a first inserter and attaching the second dynamic interbody device to a second inserter;
    removing the first expandable trial from the disc space and the first guide;
    placing the first dynamic interbody device through the first guide and into the disc space;
    removing the second expandable trial from the disc space and the second guide;
    placing the second dynamic interbody device through the second guide and into the disc space; and
    releasing the first dynamic interbody device and the second dynamic interbody device from the first and second inserters.

2. The method of claim 1, further comprising removing the bridge assembly from the taps.

3. The method of claim 1, further comprising coupling at least one dynamic posterior stabilization system to the first vertebra and the second vertebra.

4. The method of claim 1, further comprising forming grooves in the first vertebra to accommodate keels of the first dynamic interbody device and the second dynamic interbody device.

5. The method of claim 1, wherein placing the second dynamic interbody device couples the second dynamic interbody device to the first dynamic interbody device.

6. The method of claim 1, using an imaging technique to assess the position of the first dynamic interbody device and the second dynamic interbody device after the dynamic interbody devices are placed between the first vertebra and the second vertebra.

7. The method of claim 1, further comprising using a scale on the first expandable trial to determine the height of the first dynamic interbody device.

8. The method of claim 1, further comprising placing a keel guide through a passage in the first guide; forming a channel in the first vertebra for a keel of the first dynamic interbody device.

9. The method of claim 1, further comprising placing a keel guide through a passage in the second guide; forming a channel in the first vertebra for a keel of the second dynamic interbody device.

10. The method of claim 1, further comprising:
    placing a keel guide through a passage in the first guide;
    forming a channel in the first vertebra for a keel of the first dynamic interbody device;
    placing a keel guide through a passage in the second guide; and
    forming a channel in the first vertebra for a keel of the second dynamic interbody device.

11. A method of inserting a first dynamic interbody device and a second dynamic interbody device in a disc space between a first vertebra and a second vertebra, comprising:

inserting a first expandable trial and a second expandable trial in the disc space between the first vertebra and the second vertebra;

coupling a first guide to the first expandable trial and a second guide to the second expandable trial;

attaching a bridge assembly to the first guide and the second guide;

adjusting the separation distance between a movable plate and a base plate of the first expandable trial and adjusting the separation distance between a movable plate and a base plate of the second expandable trial;

attaching the first dynamic interbody device to a first inserter and attaching the second dynamic interbody device to a second inserter;

removing the first expandable trial from the disc space and the first guide;

placing the first dynamic interbody device through the first guide and into the disc space;

removing the second expandable trial from the disc space and the second guide;

placing the second dynamic interbody device through the second guide and into the disc space; and releasing the first dynamic interbody device and the second dynamic interbody device from the first and second inserters.

12. The method of claim 11, further comprising removing the bridge assembly from the first guide and the second guide.

13. The method of claim 11, further comprising coupling at least one dynamic posterior stabilization system to the first vertebra and the second vertebra.

14. The method of claim 11, further comprising placing a keel guide through a passage in the first guide; forming a channel in the first vertebra for a keel of the first dynamic interbody device.

15. The method of claim 11, further comprising placing a keel guide through a passage in the second guide; forming a channel in the first vertebra for a keel of the second dynamic interbody device.

16. The method of claim 11, wherein placing the second dynamic interbody device couples the second dynamic interbody device to the first dynamic interbody device.

17. The method of claim 11, further comprising using a scale on the first expandable trial to determine the height of the first dynamic interbody device.

18. The method of claim 11, further comprising using an imaging technique to assess the position of the first dynamic interbody device and the second dynamic interbody device after the dynamic interbody devices are placed between the first vertebra and the second vertebra.

19. The method of claim 11, further comprising forming grooves in the first vertebra to accommodate keels of the first dynamic interbody device and the second dynamic interbody device.

20. The method of claim 11, further comprising:
placing a keel guide through a passage in the first guide;
forming a channel in the first vertebra for a keel of the first dynamic interbody device;
placing a keel guide through a passage in the second guide; and
forming a channel in the first vertebra for a keel of the second dynamic interbody device.

21. A method of inserting a first dynamic interbody device and a second dynamic interbody device in a disc space between a first vertebra and a second vertebra, comprising:
placing a first expandable trial into a first guide of a bridge assembly;
placing an end of the first expandable trial into the disc space between the first vertebra and the second vertebra;
placing a second expandable trial into a second guide of the bridge assembly;
placing an end of the second expandable trial into the disc space between the first vertebra and the second vertebra;
adjusting the separation distance between a movable plate and a base plate of the first expandable trial such that the movable plate and the base plate of the first expandable trial engage endplates of the first and second vertebra;
adjusting the separation distance between a movable plate and a base plate of the second expandable trial such that the movable plate and the base plate of the second expandable trial engage endplates of the first and second vertebra;
attaching the first dynamic interbody device to a first inserter;
attaching the second dynamic interbody device to a second inserter;
removing the first expandable trial from the disc space and the first guide;
placing the first dynamic interbody device into the first guide and into the disc space;
removing the second expandable trial from the disc space and the second guide;
placing the second dynamic interbody device into the second guide and into the disc space; and
releasing the first dynamic interbody device and the second dynamic interbody device from the first and second inserters.

* * * * *